US011771761B2

(12) United States Patent
Talaat et al.

(10) Patent No.: US 11,771,761 B2
(45) Date of Patent: Oct. 3, 2023

(54) ADJUVANT FOR ANIMAL AND HUMAN VACCINES

(71) Applicant: Wisconsin Alumni Research Foundation, Madison, WI (US)

(72) Inventors: Adel M. Talaat, Madison, WI (US); Shaswath Chandrasekar, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 330 days.

(21) Appl. No.: 16/900,070

(22) Filed: Jun. 12, 2020

(65) Prior Publication Data

US 2020/0390883 A1 Dec. 17, 2020

Related U.S. Application Data

(60) Provisional application No. 62/860,640, filed on Jun. 12, 2019.

(51) Int. Cl.
*A61K 39/39* (2006.01)
*A61K 39/215* (2006.01)
*A61K 39/00* (2006.01)
*B82Y 5/00* (2011.01)

(52) U.S. Cl.
CPC ............ *A61K 39/39* (2013.01); *A61K 39/215* (2013.01); *A61K 2039/55577* (2013.01); *A61K 2039/55583* (2013.01); *B82Y 5/00* (2013.01)

(58) Field of Classification Search
CPC .......... A61K 2039/55577; A61K 2039/55555; A61K 2039/53; A61K 39/04; A61K 2039/55583; A61K 39/12; A61K 38/162; A61K 39/215; A61K 39/39; A61K 47/36; C07K 14/35; C07K 14/195; C07K 14/005; C07K 14/165; C12N 1/36; C12N 15/86; C12N 1/20; C12N 1/205; C12N 15/1031; C12N 15/1136; C12N 15/74; C12N 15/88; C12N 2710/24134; C12N 2710/24143; C12N 2770/20022; C12N 2770/20034; C12N 7/00; C12N 1/00; C12N 11/00; C12N 15/00; A61P 31/06; A61P 37/04; A61P 31/14; G01N 33/5695; G01N 2333/30; G01N 33/56933; C12R 2001/32; B82Y 5/00; C12Q 1/689; C12Q 2600/156; C12Q 2600/158
See application file for complete search history.

(56) References Cited

U.S. PATENT DOCUMENTS

| | | | |
|---|---|---|---|
| 9,220,764 | B2 | 12/2015 | Talaat |
| 9,663,758 | B2 | 5/2017 | Talaat |
| 2009/0169636 | A1 | 7/2009 | O'Hagan |
| 2018/0147272 | A1 | 5/2018 | Talaat |

FOREIGN PATENT DOCUMENTS

| | | |
|---|---|---|
| WO | WO2004092329 | * 10/2004 |

OTHER PUBLICATIONS

Zhang P, et al. 2017. Astragalus polysaccharides enhance the immune response to avian infectious bronchitis virus vaccination in chickens. Microb Pathog 111:81-85.
Alpar, H. O., et al. "Quil-A-Chitosan: A novel mucosal adjuvant." (2003). MVADS Conference. Dublin, Ireland. Jun. 4-6, 2003.
Barhate, G., et al. "Quillaja saponaria extract as mucosal adjuvant with chitosan functionalized gold nanoparticles for mucosal vaccine delivery: stability and immunoefficiency studies." International journal of pharmaceutics 441.1-2 (2013): 636-642.
Behzadi S, et al. 2017. Cellular uptake of nanoparticles: journey inside the cell. Chem Soc Rev 46:4218-4244.
Berge, S. M., et al. "Pharmaceutical salts." Journal of pharmaceutical sciences 66.1 (1977): 1-19.
Borges O, et al. 2005. Preparation of coated nanoparticles for a new mucosal vaccine delivery system. Int J Pharm 299:155-66.
Britton P, et al. 2012. Modification of the avian coronavirus infectious bronchitis virus for vaccine development. Bioengineered Bugs 3:114-119.
Cavanagh D, et al. 1997. Relationship between sequence variation in the S1 spike protein of infectious bronchitis virus and the extent of cross-protection in vivo. Avian Pathology 26:63-74.
Chhabra R, et al. 2015. Immune Responses to Virulent and Vaccine Strains of Infectious Bronchitis Viruses in Chickens. Viral Immunol 28:478-88.
Chhabra R, et al. 2015. Mucosal, Cellular, and Humoral Immune Responses Induced by Different Live Infectious Bronchitis Virus Vaccination Regimes and Protection Conferred against Infectious Bronchitis Virus Q1 Strain. Clin Vaccine Immunol 22:1050-9.
Collisson EW, et al. 2000. Cytotoxic T lymphocytes are critical in the control of infectious bronchitis virus in poultry. Dev Comp Immunol 24:187-200.
De Wit JJ, et al. 2014. Factors influencing the outcome of infectious bronchitis vaccination and challenge experiments. Avian Pathol 43:485-97.
Dolz R, et al. 2012. New insights on infectious bronchitis virus pathogenesis: Characterization of Italy 02 serotype in chicks and adult hens. Veterinary Microbiology 156:256-264.
Fraga AP, et al. 2013. Emergence of a New Genotype of Avian Infectious Bronchitis Virus in Brazil. Avian Diseases 57:225-232.
Ganapathy K, et al. 2005. A comparison of methods of inducing lachrymation and tear collection in chickens for detection of virus-specific immuoglobulins after infection with infectious bronchitis virus. Avian Pathol 34:248-51.

(Continued)

*Primary Examiner* — Bao Q Li
(74) *Attorney, Agent, or Firm* — QUARLES & BRADY LLP

(57) ABSTRACT

Quil-A chitosan spherical nanostructure complexes as well as methods of making and using such complexes are disclosed herein. Also provided are Quil-A chitosan spherical nanostrucutres loaded with one or more RNA, DNA, or protein payload molecules as well as methods of making and using such loaded complexes.

11 Claims, 38 Drawing Sheets

Specification includes a Sequence Listing.

(56) References Cited

OTHER PUBLICATIONS

Garg, R. et al. "A novel combination adjuvant platform for human and animal vaccines." Vaccine 35.35 (2017): 4486-4489.
Guo Z, et al. 2010. Priming with a DNA vaccine and boosting with an inactivated vaccine enhance the immune response against infectious bronchitis virus. J Virol Methods 167:84-9.
Hamers C, et al. 2007. DNA vaccination against pseudorabies virus and bovine respiratory syncytial virus infections of young animals in the face of maternally derived immunity. J Comp Pathol 137 Suppl 1:S35-41.
Harush-Frenkel O, et al. 2007. Targeting of nanoparticles to the clathrin-mediated endocytic pathway. Biochem Biophys Res Commun 353:26-32.
Ho Ni, et al. 2018. Adjuvants Enhancing Cross-Presentation by Dendritic Cells: The Key to More Effective Vaccines? Front Immunol 9:2874.
Hoven, V. P., et al. "Surface-charged chitosan: Preparation and protein adsorption." Carbohydrate Polymers 68.1 (2007): 44-53.
International Searching Authority. International Search Report and Written Opinion for application PCT/US2020/037438, dated Nov. 4, 2020. 11 pages.
Jackwood MW, et al. 2009. Infectious bronchitis virus field vaccination coverage and persistence of Arkansas-type viruses in commercial broilers. Avian Dis 53:175-83.
Jazayeri SD, et al. 2019. Recent advances in delivery of veterinary DNA vaccines against avian pathogens. Vet Res 50:78.
Kapczynski DR, et al. 2003. Protection of chickens from infectious bronchitis by in ovo and intramuscular vaccination with a DNA vaccine expressing the S1 glycoprotein. Avian Dis 47:272-85.
Kingstad-Bakke, B. A., et al. "Effective mosaic-based nanovaccines against avian influenza in poultry." Vaccine 37.35 (2019): 5051-5058.
Lai, RPJ, et al. "Mixed adjuvant formulations reveal a new combination that elicit antibody response comparable to Freund's adjuvants." PloS one 7.4 (2012): e35083.
Levast, B., et al. "Vaccine potentiation by combination adjuvants." Vaccines 2.2 (2014): 297-322.
Liu MA. 2003. DNA vaccines: a review. J Intern Med 253:402-10.
Marangon S, et al. 2007. The use of vaccination in poultry production. Rev Sci Tech 26:265-74.
McKinley ET, et al. 2008. Avian coronavirus infectious bronchitis attenuated live vaccines undergo selection of subpopulations and mutations following vaccination. Vaccine 26:1274-84.
Mockett AP, et al. 1987. Maternally-derived antibody to infectious bronchitis virus: Its detection in chick trachea and serum and its role in protection. Avian Pathol 16:407-16.
Mohammed MA, et al. 2017. An Overview of Chitosan Nanoparticles and Its Application in Non-Parenteral Drug Delivery. Pharmaceutics 9.
Mutwiri, G., et al. "Combination adjuvants: the next generation of adjuvants?." Expert review of vaccines 10.1 (2011): 95-107.
Orr-Burks N, et al. 2014. Immunoglobulin A as an early humoral responder after mucosal avian coronavirus vaccination. Avian Dis 58:279-86.
Oyewumi Mo, et al. 2010. Nano-microparticles as immune adjuvants: correlating particle sizes and the resultant immune responses. Expert Rev Vaccines 9:1095-107.
Rajput ZI, et al. 2007. Adjuvant effects of saponins on animal immune responses. J Zhejiang Univ Sci B 8:153-61.
Riteau N, et al. 2016. Chitosan: An Adjuvant with an Unanticipated Sting. Immunity 44:522-524.
Roy K, et al. 1999. Oral gene delivery with chitosan-DNA nanoparticles generates immunologic protection in a murine model of peanut allergy. Nat Med 5:387-91.
Seo SH, et al. 2000. Adoptive transfer of infectious bronchitis virus primed alphabeta T cells bearing CD8 antigen protects chicks from acute infection. Virology 269:183-9.
Shirvani E, et al. 2018. A Recombinant Newcastle Disease Virus (NDV) Expressing S Protein of Infectious Bronchitis Virus (IBV) Protects Chickens against IBV and NDV. Sci Rep 8:11951.
Sogias IA, et al. 2008. Why is chitosan mucoadhesive? Biomacromolecules 9:1837-42.
Tan B, et al. 2009. Coadministration of chicken GM-CSF with a DNA vaccine expressing infectious bronchitis virus (IBV) S1 glycoprotein enhances the specific immune response and protects against IBV infection. Arch Virol 154:1117-24.
Tan L, et al. 2016. Infectious bronchitis virus poly-epitope-based vaccine protects chickens from acute infection. Vaccine 34:5209-5216.
Tang M, et al. 2008. Enhancement of the immunogenicity of an infectious bronchitis virus DNA vaccine by a bicistronic plasmid encoding nucleocapsid protein and interleukin-2. J Virol Methods 149:42-8.
Tian L, et al. 2008. The immunoreactivity of a chimeric multi-epitope DNA vaccine against IBV in chickens. Biochem Biophys Res Commun 377:221-5.
Wack, A., et al. "Combination adjuvants for the induction of potent, long-lasting antibody and T-cell responses to influenza vaccine in mice." Vaccine 26.4 (2008): 552-561.
Wolff JA, et al. 1990. Direct gene transfer into mouse muscle in vivo. Science 247:1465-8.
Yan F, et al. 2013. Protection of chickens against infectious bronchitis virus with a multivalent DNA vaccine and boosting with an inactivated vaccine. J Vet Sci 14:53-60.
Yang T, et al. 2009. Multivalent DNA vaccine enhanced protection efficacy against infectious bronchitis virus in chickens. J Vet Med Sci 71:1585-90.
Zhang F, et al. 2016. Intranasal Immunization of Mice to Avoid Interference of Maternal Antibody against H5N1 Infection. PLoS One 11:e0157041.
Bande et al., "Synthesis and Characterization of Chitosan-Saponin Nanoparticle for Application in Plasmid DNA Delivery," Journal of Nanomaterials, vol. 2015, Article ID 371529, 8 pages., Hindawi Publishing Corporation, http://dx.doi.org/10.1155/2015/371529, (2015).
Kamstrup et al., "Preparation and characterization of quillaja saponin with less heterogeneity than Quil-A," Vaccine 18, (2000) pp. 2244-2249.
Moreno et al., "Preparation and Characterization of an Oral Vaccine Formulation Using Electrosprayed Chitosan Microparticles," AAPS PharmSciTech, vol. 19, No. 8, (2018), DOI: 10.1208/12249-018-1190-1.
Ren et al., "Construction and immunogenicity of a DNA vaccine coexpressing GP3 and GP5 of genotype-I porcine reproductive and respiratory syndrome virus," BMC Veterinary Research, (2014), 10:128.

* cited by examiner

TEM images (Chitosan-DNA complex 100 ug/ml)

| Construct # | Quil-A conc (%) | Chitosan conc (%) |
|---|---|---|
| 1 | 0.001 | 0.02 |
| 2 | 0.00025 | |
| 3 | 0.0000625 | |
| 4 | 0.000015625 | |

| Groups (n=7) BL6 mice |
|---|
| Adjuplex (control) |
| QAC conc. 1 |
| QAC conc. 2 |
| Chitosan |
| Quil A |

-All with 30μg OVA protein for T cell responses
-All with 30μg DQ-OVA protein for innate cell processing

| Groups | Vaccine construct (N=6) | Dosage |
|---|---|---|
| Group-1 | Neg control | - |
| Group-2 | Inactivated whole virus | 30 ug |
| Group-3 | Chitosan- IBV whole virus | 30 ug |
| Group-4 | QAC- IBV whole virus | 30 ug |

A)

B)

A)

B)

A)

B)

pCMV-SARS CoV-2 Truncated Spike
7850 bp

ADJUVANT FOR ANIMAL AND HUMAN VACCINES

CROSS-REFERENCE TO RELATED APPLICATIONS

This application claims priority to U.S. Provisional Application No. 62/860,640, filed Jun. 12, 2019, which is incorporated herein by reference in its entirety.

STATEMENT REGARDING FEDERALLY SPONSORED RESEARCH

This invention was made with government support under 2016-67021-25042 awarded by the USDA/NIFA. The government has certain rights in the invention.

REFERENCE TO A SEQUENCE LISTING SUBMITTED VIA EFS-WEB

The content of the ASCII text file of the sequence listing named "960296_04039_ST25.txt" which is 78,561 bytes in size was created on Apr. 11, 2022 and electronically submitted via EFS-Web is incorporated herein by reference in its entirety.

BACKGROUND

Vaccines have been hailed as one of the greatest achievements in public health during the past century. Vaccines have been a key factor for fighting infectious diseases that afflict humans and animals, with corresponding increases in human average life expectancy. The global eradication of Smallpox virus in humans and Rinderpest virus in animals, and the near eradication or successful prevention of other viral or bacterial infections, for example meningitis in children due to *Hemophilus influenze* Type B, offer compelling examples.

Adjuvants play a key role in the successful use of vaccines in human and animal medicines. However, only a handful of such adjuvants are approved for human and animal use. Needed in the art are additional vaccine adjuvant compositions for the improvement of human and animal medicines.

SUMMARY OF THE INVENTION

In a first aspect, provided herein is a composition comprising disaggregated spherical nanostructures comprising Quil-A and chitosan. The disaggregated spherical nanostructures may additionally comprising a payload molecule.

In some embodiments, the payload molecule is selected from the group consisting of a DNA molecule, an RNA molecule, a polynucleotide, a protein, a polypeptide, a virus, a microbe, an attenuated virus, an attenuated microbe, a small molecule, an antibody, or a mixture thereof. In some embodiments, the payload molecule is negatively charged. In some embodiments, the payload is functionalized. In some embodiments, the payload molecule is an antigen specific for *Mycobacterium avium* subspecies paratuberculosis, *Mycobacterium bovis, Mycobacterium tuberculosis*, or *Mycobacterium avium* subspecies *avium*.

In some embodiments, the chitosan is functionalized by treatment with 5-formyl-2-furan sulfonic acid and sodium borohydride such that the chitosan surface is negatively charged.

In some embodiments, the spherical nanostructures are between about 5 nm and about 100 nm in diameter in the absence of a payload molecule.

In a second aspect, provided herein is a vaccine formulation comprising an antigen, the disaggregated spherical nanostructures comprising Quil-A and chitosan described herein as an adjuvant, and a pharmaceutically acceptable carrier.

In a third aspect, provided herein is a vaccine formulation comprising an antigen specific for *Mycobacterium avium* subspecies paratuberculosis, *Mycobacterium bovis, Mycobacterium tuberculosis*, or *Mycobacterium avium* subspecies *avium* and the disaggregated spherical nanostructures comprising Quil-A and chitosan described herein.

In a forth aspect, provided herein is a method of forming a composition comprising Quil-A chitosan spherical nanostructures, comprising the steps of heating a first solution comprising Quil-A at about 55° C. for about 30 minutes; heating a second solution comprising chitosan at about 55° C. for about 30 minutes; mixing equal volumes of the first and second solution dropwise to form a combined solution; vortex mixing the combined solution for about 30 seconds to form a combined, vortexed solution; and incubating the combined vortexed solution whereby a composition comprising Quil-A chitosan spherical nanostructures is formed.

In some embodiments, the combined vortexed solution is incubated at room temperature for about 1 hour. In some embodiments, the first solution additionally comprises a DNA antigen. In some embodiments, the combined vortexed solution is incubated at about 37 C with shaking at about 110 rpm for about 1 hour. In some embodiments, the first solution additionally comprises a protein antigen.

In some embodiments, the first solution comprises about 0.002% Quil-A and the second solution comprises about 0.04% chitosan. In some embodiments, the first solution and the second solution each have a pH between 5.5 and 7.0.

In a fifth aspect, provided herein is a composition comprising Quil-A chitosan spherical nanostructures produced by the methods described herein. In some embodiments the composition additionally comprises an antigen payload molecule.

In a sixth aspect, provided herein is a method of immunizing a subject against an antigen comprising the step of administering to the subject a vaccine formulation comprising a composition comprising Quil-A chitosan spherical nanostructures produced by the methods described herein and an antigen payload molecule. In some embodiments, the subject is selected from the group consisting of a human, a mouse, a rat, a cow, a horse, a pig, a goat, a sheep, a cat, a dog, or a bird.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF DRAWINGS

The patent or patent application file contains at least one drawing in color. Copies of this patent or patent application publication with color drawings will be provided by the Office upon request and payment of the necessary fee.

DETAILED DESCRIPTION OF THE DISCLOSURE

In General

Figure 1:
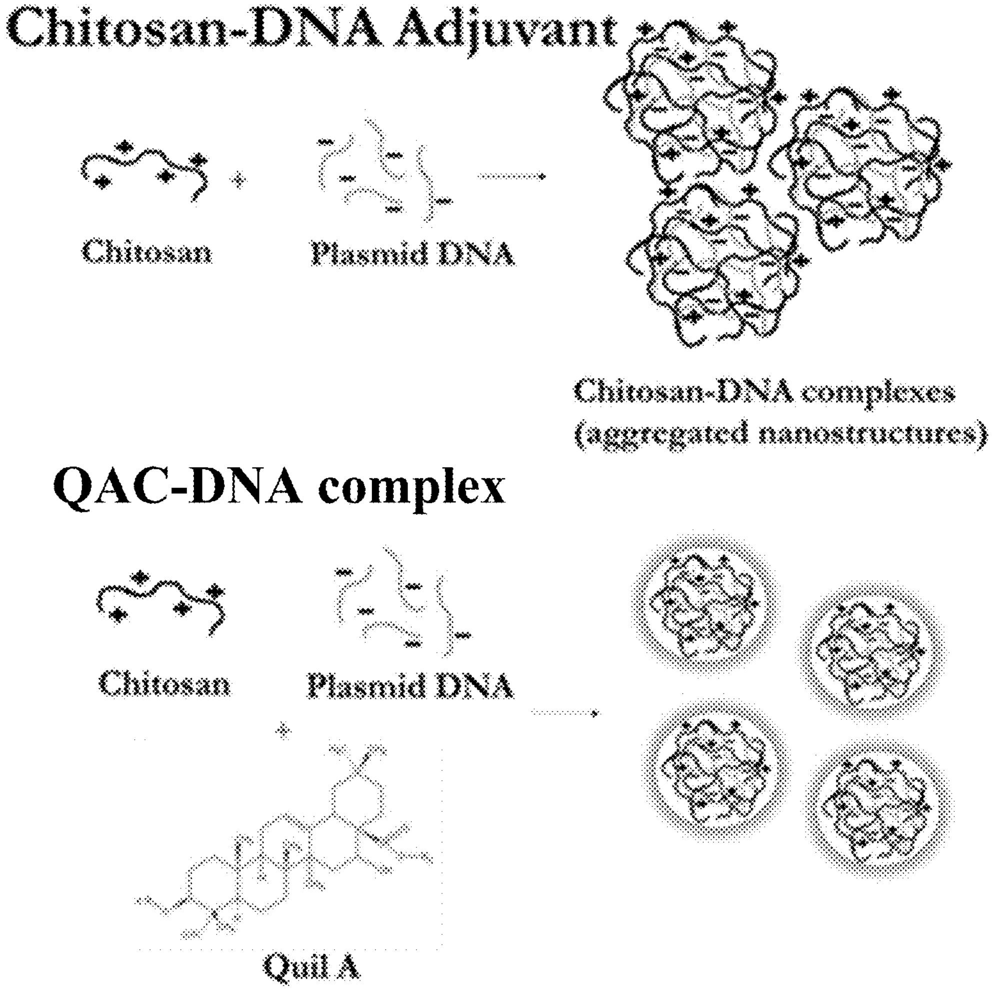
FIG. 1 shows the formation of adjuvant nanostructures using Quil-A and chitosan with a DNA immunogen.
Figure 2:
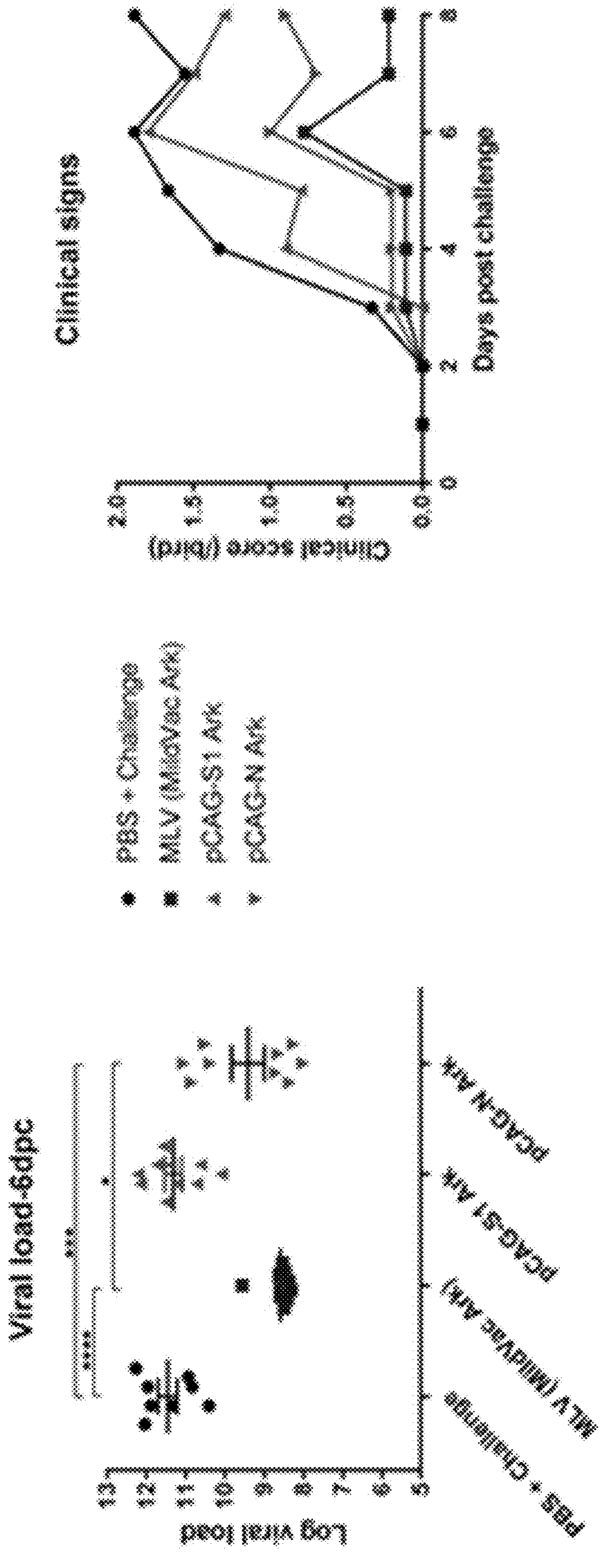
FIG. 2 shows parenteral immunization with naked DNA constructs. Partial protection was observed with naked DNA vaccines for parenteral administration. A partial reduction in viral burden and clinical signs of severity were observed with the naked IBV N vaccine construct, higher levels of circulating IBV specific IgY was observed in naked IBV N vaccinated groups vs spike subunit 1 glycoprotein (51), and mucosal IgA was not detected.
Figure 2:
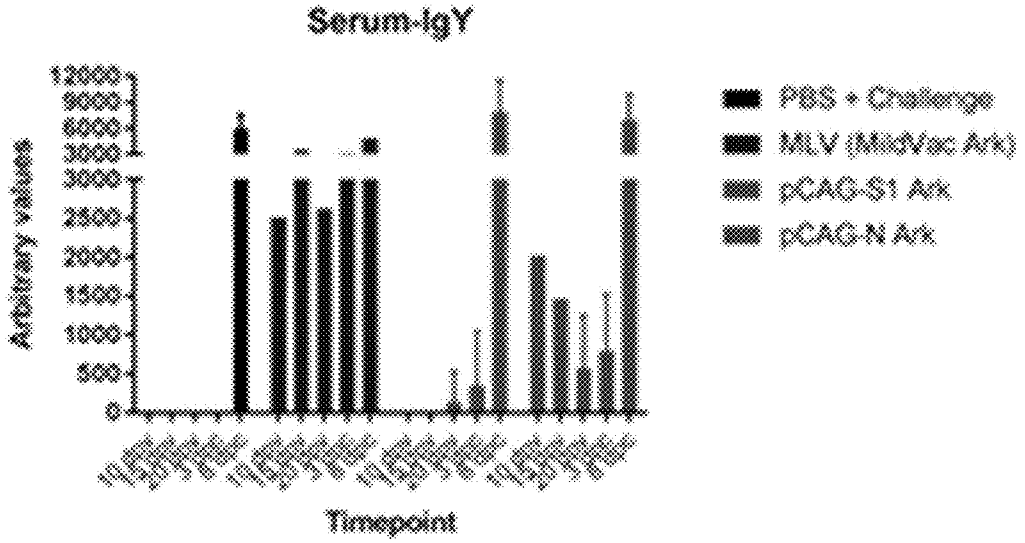
Figure 2:
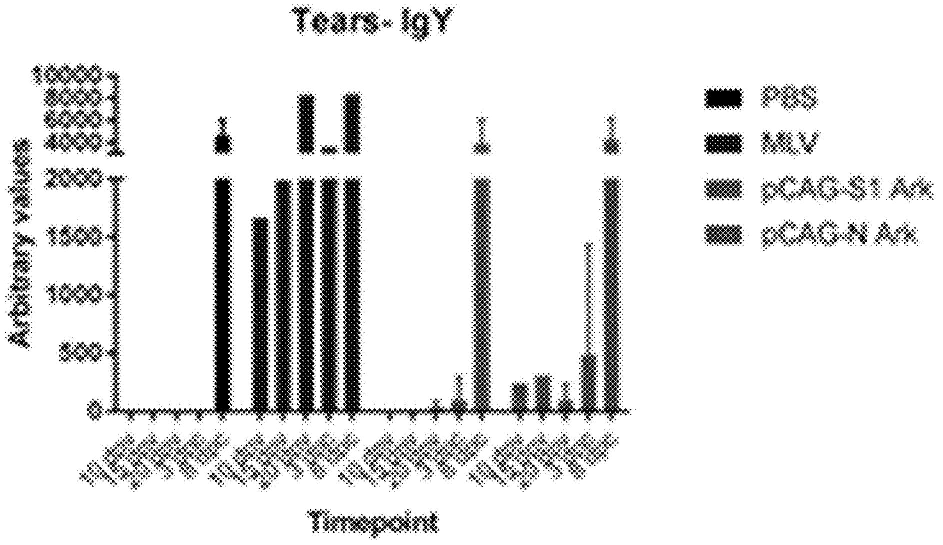

The present disclosure broadly relates to a Quil-A chitosan complex as well as methods of making and using such a complex.

In some embodiments, the present disclosure describes an adjuvant for use in a vaccine. The adjuvant is a Quil-A chitosan complex (QAC complex), which stimulates an immune response when administered in a vaccine composition.

In some embodiments, Quil-A and chitosan are combined to form a nanostructure complex which may be used as an adjuvant in a vaccine composition. The QAC complex may be loaded with a payload molecule, such as the antigen or immunogen with which the QAC complex stimulates an immune response. The QAC complex may be formulated into a vaccine composition with a pharmaceutically acceptable carrier.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" means within 5% of a stated concentration range, density, temperature, or time frame.

As used herein the specification, "a" or "an" may mean one or more, unless clearly indicated otherwise. As used herein in the claims, when used in conjunction with the word "comprising," the words "a" or "an" may mean one or more than one.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "therapeutically effective amount," as used herein, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with wild-type strain. The protective immunity conferred by a vaccine may be evaluated by measuring, e.g., reduction in clinical signs such as mortality, morbidity, temperature number, overall physical condition, and overall health and performance of the subject. The amount of a vaccine that is therapeutically effective may vary depending on the particular virus used, or the condition of the subject, and may be determined by a physician.

The term "protected," as used herein, refers to immunization of a patient against a disease. The immunization may be caused by administering a vaccine comprising an antigen. Specifically, in the present invention, the immunized patient is protected from a fungal, bacterial, or viral infection.

The term "vaccine," as used herein, refers to a composition that includes an antigen. Vaccine may also include a biological preparation that improves immunity to a particular disease. A vaccine may typically contain an agent, referred to as an antigen, that resembles a disease-causing microorganism, and the agent may often be made from weakened or killed forms of the microbe, its toxins or one of its surface proteins. The antigen may stimulate the body's immune system to recognize the agent as foreign, destroy it, and "remember" it, so that the immune system can more easily recognize and destroy any of these microorganisms that it later encounters.

Vaccines may be prophylactic, e.g., to prevent or ameliorate the effects of a future infection by any natural or "wild" pathogen, or therapeutic, e.g., to treat the disease. Administration of the vaccine to a subject results in an immune response, generally against one or more specific diseases. The amount of a vaccine that is therapeutically effective may vary depending on the particular virus used, or the condition of the patient, and may be determined by a physician. The vaccine may be introduced directly into the subject by the subcutaneous, oral, oronasal, or intranasal routes of administration.

A vaccine of the present invention will include a suitable antigen to stimulate an immune response in a subject or patient. It is envisioned that vaccines of the present invention are not limited to a specific antigen or disease target, except where specifically specified. In some embodiments, the vaccine of the present invention provides immunity against a fungus, a parasite, a bacteria, a microbe, or a virus.

In some embodiments, the vaccine of the present disclosure provides immunity against bacteria. In one embodiment of the invention, the vaccine comprises an antigen for a *Mycobacterium* species, such as, but not limited to, *Mycobacterium avium* subspecies paratuberculosis, *Mycobacterium bovis, Mycobacterium tuberculosis*, and *Mycobacterium avium* subspecies *avium*. A non-limiting example of an antigen of the present disclosure are the compositions described in U.S. Patent Publication No. 2018/0147272 ("Vaccine Candidates Against Johne's Disease"), U.S. Pat. No. 9,663,758 ("Global Gene Regulators (GGR) as vaccine candidates against paratuberculosis"), and U.S. Pat. No. 9,220,764 ("Immunogenic compositions against tuberculosis").

In some embodiments, the vaccine of the present disclosure provides immunity against a virus. In some embodiments, the vaccine comprises an antigen for infectious bronchitis virus. In some embodiments, the vaccine comprises an antigen for Severe Acute Respirator Syndrome Coronavirus 2 (SARS-CoV-2).

Vaccine Administration

The term "administration," as used herein, refers to the introduction of a substance, such as a vaccine, into a subject's body. The administration, e.g., parenteral administration, may include subcutaneous administration, intramuscular administration, transcutaneous administration, intradermal administration, intraperitoneal administration, intraocular administration, intranasal administration and intravenous administration.

The vaccine or the composition according to the invention may be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, the vaccine may be applied by topical application as a drop, spray, gel or ointment to the mucosal epithelium of the eye, nose, mouth, anus, or vagina, or onto the epidermis of the outer skin at any part of the body.

Other possible routes of application are by spray, aerosol, or powder application through inhalation via the respiratory tract. In this last case, the particle size that is used will determine how deep the particles will penetrate into the respiratory tract.

Alternatively, application may be via the alimentary route, by combining with the food, feed or drinking water e.g. as a powder, a liquid, or tablet, or by administration directly into the mouth as a: liquid, a gel, a tablet, or a capsule, or to the anus as a suppository.

The term "immune status" or "immunocompetence," as used herein, refers to the ability of the body to produce a normal immune response following exposure to an antigen. Immunocompetence is the opposite of immunodeficiency or immuno-incompetent or immuno-compromised.

The present disclosure is generally applied to mammals, including but not limited to humans, cows, horses, sheep, pigs, goats, rabbits, dogs, cats, mice and rats. In some embodiments, the present disclosure can be applied to birds. In certain embodiments, non-human mammals, such as mice and rats, may also be used for the purpose of demonstration. One may use the present invention for veterinary purpose. For example, one may wish to treat commercially important farm animals, such as cows, horses, pigs, rabbits, goats, sheep, and birds, such as chickens. One may also wish to treat companion animals, such as cats and dogs.

Adjuvants

Figure 12:
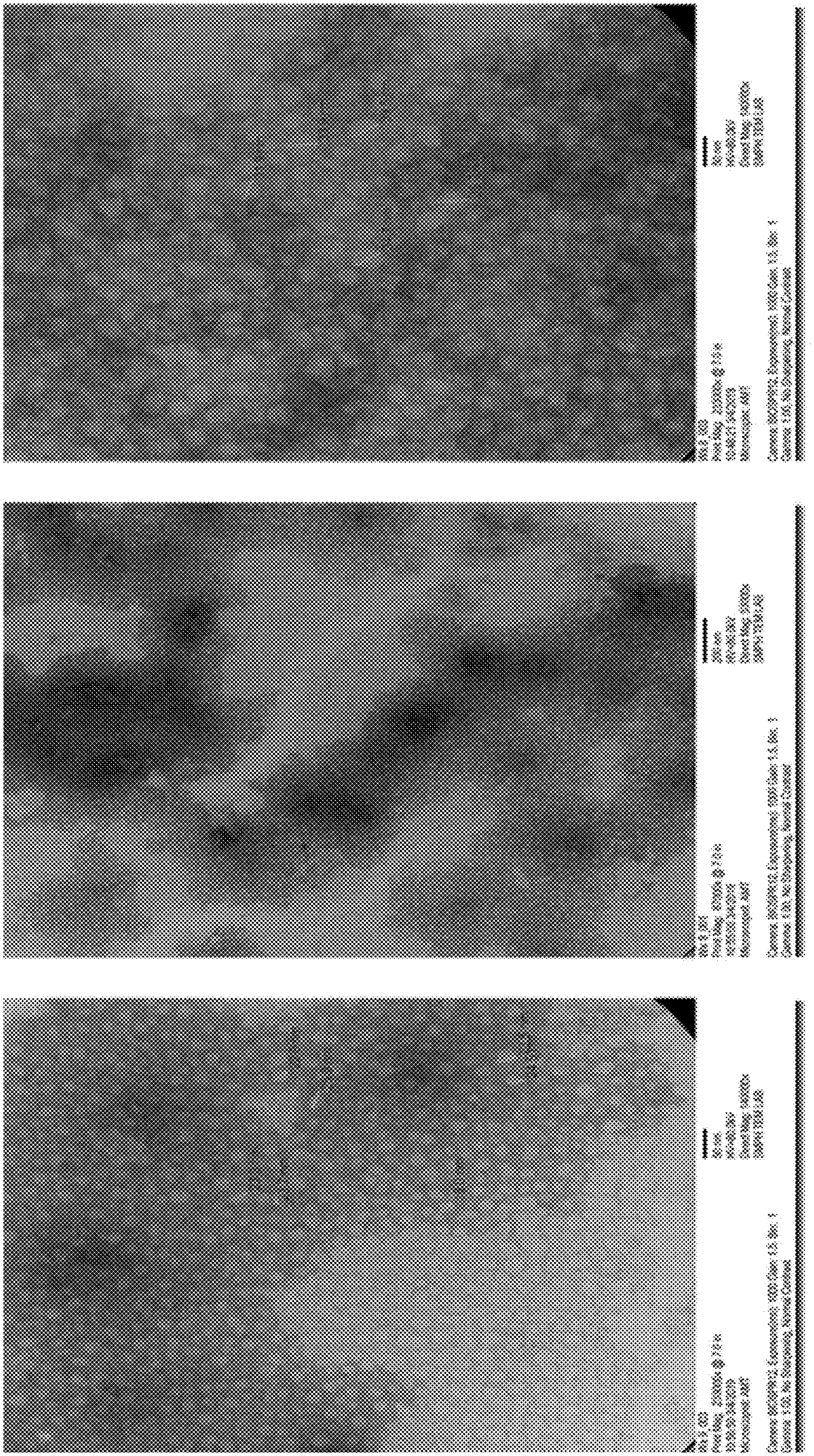
FIG. 12 shows images of QAC nanostructures at varying ratios of Quil-A:chitosan (0.001:0.02-0.01).

As used herein "Quil-A chitosan complex" or "QAC complex" refers to a composition of Quil-A and chitosan which forms distinct disaggregated spherical nanostructures. FIG. 12 shows an example of these disaggregated spherical nanostructures. As used herein, "disaggregated," refers to the formation of discrete observable particles as opposed to aggregated non-discrete assemblies with non-distinct boundaries. The QAC complex nanostructures are less 100 nm in diameter when measured in the absence of any payload molecules. For example, between about 5 nm and about 100 nm, between about 10 nm and about 95 nm, between about 15 nm an about 90 nm, between about 20 nm and about 90 nm, or between about 25 nm and about 85 nm. The QAC complex may be loaded with one or more payload molecules. The payload-QAC complex may be between about 20 nm and about 1000 nm in diameter. The specific size of the payload-QAC complex will vary depending on the size and amount of payload in the nanostructure.

In one embodiment, the QAC complex is formed by mixing a first solution of Quil-A into a second solution of chitosan to form a final mixed solution including the QAC complex. In the final mixed solution, the Quil-A and the chitosan are typically present at a ratio of between about 1:15 to about 1:100, between about 1:15 and about 1:75, between about 1:15 and about 1:50, between about 1:15 and about 1:25, between about 1:17 and about 1:25, or between about 1:18 and about 1:25. In some embodiments, the Quil-A and the chitosan are present at a ratio of about 1:20 (e.g., 1:15, 1:16, 1:17, 1:18, 1:19, 1:20, 1:21, 1:22, 1:23, 1:24, or 1:25) in the final mixed solution. In some embodiments, in the final solution Quil-A is at a concentration of 0.001% and chitosan is at a concentration of between about 0.02% and about 0.1%. In some embodiments, in the final solution Quil-A is at a concentration between about 0.00001% and about 0.5%. In some embodiments, in the final solution the chitosan is at a concertation between about 0.00015% and about 7.5%.

In some embodiments, the Quil-A solution and the chitosan solution are mixed drop-wise. In some embodiments, the Quil-A solution and the chitosan solution are mixed by vortex mixing for about 15-90 seconds (15 seconds, 20 seconds, 25 seconds, 30 seconds, 35 seconds, 40 seconds, 45 seconds, 50 seconds, 60 seconds, 70 seconds, 80 seconds or 90 seconds). In some embodiments, the Quil-A solution and the chitosan solution are mixed drop-wise followed by vortex mixing for about 15-90 seconds (15 seconds, 20 seconds, 25 seconds, 30 seconds, 35 seconds, 40 seconds, 45 seconds, 50 seconds, 60 seconds, 70 seconds, 80 seconds or 90 seconds).

The Quil-A solution and the chitosan solution may be heated prior to mixing. In some embodiments, the Quil-A solution and the chitosan solution are heated to a temperature between about 20° C. and about 60° C. (e.g., 20° C., 25° C., 30° C., 35° C., 40° C., 45° C., 50° C., 55° C., or 60° C.) for between about 20 to about 40 minutes (20 minutes, 25 minutes, 30 minutes, 35 minutes, or 40 minutes) prior to mixing. In some embodiments, after mixing the final solution is incubated at room temperature for about 1 hour to promote QAC complex formation. In some embodiments, after mixing the final solution is incubated for 1 hour at between about 20° C. and about 45° C. (e.g., 20° C., 21° C., 22° C., 23° C., 24° C., 25° C., 26° C., 27° C., 28° C., 29° C., 30° C., 31, 32° C., 33° C., 34° C., 35° C., 36° C., 37° C., 38° C., 39° C., 40° C., 41° C., 42° C., 43° C., 44° C., or 45° C.) with shaking at between about 90 rpm and about 150 rpm (e.g., 90 rpm, 95 rpm, 100 rpm, 105 rpm, 110 rpm, 115 rpm, 120 rpm, 125 rpm, 130 rpm, 135 rpm, 140 rpm, 145 rpm, or 150 rpm). The pH of the solutions may be between 5.5 and 7.0.

In some embodiments, the Quil-A solution is prepared by creating a stock solution of Quil-A in water and diluting the stock Quil-A solution with a buffered solution. The buffer may be any suitable buffer known in the art to buffer a solution at a pH between 5.5 and 7.0. In some embodiments the buffer is sodium sulfate buffer.

In some embodiments, the chitosan solution is prepared by creating a stock solution of chitosan in acetic acid and diluting the stock acetic acid solution with a buffered solution. The buffer may be any suitable buffer in the art to buffer a solution at a pH between 5.5 and 7.0. In some embodiments the buffer is sodium acetate buffer at pH 5.5.

In some embodiments, a first solution of about 0.002% Quil-A in 50 mM sodium sulfate buffer pH 5.5 and a second solution of about 0.04% chitosan in 5 mM sodium acetate buffer pH5.5 are each heated at 55° C. for about 30 min. Equal volumes of the first and second solution are mixed dropwise then vortex mixed for about 30 s followed by incubation at room temperature for about 1 hour for QAC complex formation.

As used herein "Quil-A" refers to the powdered saponin fraction isolated from extract of the bark of *Quillaja saponaria* trees. Quil-A is commercially available, for example from Desert King sold under the product name Vet-Sap™ (desertking.com/pharmaceutical-applications/#veterinary_adjuvant).

In some embodiments, the Quil-A is replaced with a surfactant or mild detergent. Surfactants and mild detergents may include but are not limited to, polyoxyethylene (20) sorbitan monolaurate (Tween™ 20), polyethylene glycol sorbitan monostearate (Tween™ 60), polyoxyethylenesorbitan tristearate (Tween™ 65), polyoxyethylene (20) sorbitan monooleate (Tween™ 80), polyoxyethylenesorbitan trioleate (Tween™ 85), octyl oligooxyethelene (OPOE), N,N-dimethyldodecylamine (LDAO), and polyethylene glycol p-(1,1,3,3-tetramethylbutyl)-phenyl ether (Triton X-100). In general, when replacing Quil-A with a surfactant or mild detergent, the concentration of the surfactant or milk detergent will vary depending on the strength of the detergent or surfactant such that lower concentrations of stronger detergents and higher concentrations of weaker detergents are used.

As used herein "chitosan" refers to a linear polysaccharide composed of randomly distributed β-linked D-glucosamine and N-acetyl-D-glucosamine. Chitosan can be obtained from the chitin shells of shrimp and other crustaceans by treatment of the shells with an alkaline substance. Chitosan is a non-toxic, naturally occurring cationic polymer that readily complexes with DNA and negatively charged proteins. Chitosan is biocompatible and biodegradable. Compositions incorporating chitosan have sustained release kinetics and are immunomodulary by enhancing the T-cell response. In some embodiments, chitosan is deacetylated chitosan, for example >75% deacetylated chitosan. Deacetylated chitosan (>75%) is available commercially from Sigma (C3646). Higher deacetylation percentages, for example about 90%, will meditate stronger binding with nucleic acids resulting in slower release kinetics from the nanoparticle structures of the Quil-A chitosan complex. In some embodiments, the chitosan is at least 70%, 75%, 80%, 85%, 90%, or 95% deacetylated. In some embodiments, the chitosan is between about 60% and about 90% deacetylated.

The QAC complex may be loaded with one or more payload molecules. The payload molecule may be an antigen of interest for use in a vaccine composition. The payload molecule may be an immunogen for use in a vaccine composition. The payload molecule may be, but is not limited to, a DNA molecule, an RNA molecule, a polynucleotide, a protein, a polypeptide, a virus, a microbe, an attenuated virus, an attenuated microbe, a small molecule, an antibody, or a mixture thereof.

In some embodiments, the payload is a live attenuated microbe. The pathogen of interested may be attenuated or reduced in virulence by any suitable means known in the art including but not limited to repeated passaging through a series of cell cultures, animal embryos (e.g., chicken embryos), or by genetic engineering to produce a mutated strain of the pathogen (e.g., mutant bacteria or mutant fungi).

In some embodiments, the payload is a recombinant protein. In some embodiments, the payload may be a subunit vaccine.

In some embodiments, the payload is an inactivated pathogen. The pathogen of interest may be inactivated by any suitable means known in the art including but not limited to, heat treatment, UV treatment, and chemical treatment (e.g., formaldehyde or glutaraldehyde).

In some embodiments, the payload is a recombinant viral vector. The recombinant viral vector may include, but is not limited to, an adeno viral vector or a poxvirus vector. Recombinant viral vectors may be used to deliver vaccine antigens by encoding immunogenic agents from a pathogen of interest.

In some embodiments, the payload is a recombinant nucleic acid. Recombinant nucleic acids may encode an immunogenic agent from a pathogen of interest such as, but not limited to, bacterial genes and fungal genes. In some embodiments, the payload is a recombinant RNA or DNA molecule encoding an immunogenic or antigenic polypeptide.

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand). The polynucleotides may be cDNA or genomic DNA. Polynucleotides homologous to the polynucleotides described herein are also provided. Those of skill in the art understand the degeneracy of the genetic code and that a variety of polynucleotides can encode the same polypeptide.

In some embodiments, the payload is a polynucleotide construct. As used herein, the term "construct" refers to recombinant polynucleotides including, without limitation, DNA and RNA, which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome editing technologies. Constructs may also include recombinant polynucleotides created using, for example, recombinant DNA methodologies.

The payload constructs provided herein may be prepared by methods available to those of skill in the art. Notably each of the constructs described are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The constructs provided herein may include a promoter operably linked to any one of the polynucleotides described herein. The promoter may be a heterologous promoter or an endogenous promoter associated with the antigenic or immunogenic payload polypeptide.

As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

As used herein, a polynucleotide is "operably connected" or "operably linked" when it is placed into a functional relationship with a second polynucleotide sequence. For instance, a promoter is operably linked to a polynucelotide if the promoter is connected to the polynucelotide such that it may effect transcription of the polynucelotide. In various embodiments, the polynucelotide may be operably linked to at least 1, at least 2, at least 3, at least 4, at least 5, or at least 10 promoters.

Heterolgous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter. Suitable promoters include, without limitation, promoters for Rous sarcoma virus (RSV), human immunodeficiency virus (HIV-1), AmpR promoter, SV40, cytomegalovirus (CMV), SV40 virus, chicken beta actin (CAG), and the like as well as the translational elongation factor EF-1α promoter or ubiquitin promoter. Those of skill in the art are familiar with a wide variety of additional promoters for use in various cell types.

Vectors including any of the constructs or polynucleotides described herein are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons. Vectors may carry genetic elements, such as those that confer resistance to certain drugs or chemicals. In some embodiments, the payload is a vector as described herein.

In some embodiments, the payload is polypeptide antigen specific for Infectious Bronchitis Virus (IBV) or a polynucleotide encoding a polypeptide antigen specific for IBV. IBV is a member of the genus gammacoronavirus, family Coronaviridae, order Nidovirales with a 27.6 Kb single stranded positive sense RNA genome encoding major structural proteins, spike glycoprotein (S), envelope (E), membrane (M) and nucleocapsid (N). In some embodiments, the payload is selected form the group consisting of the IBV S, E, M, and N proteins and fragments thereof. In some embodiments, the payload is a polynucleotide encoding the IBV S, E, M, or N proteins or fragments thereof. In some embodiments, the payload a polypeptide at least 80%, at least 85%, at least 90%, at least 95%, at least 98%, or at least 99% to the IBV nucleocapsid protein of SEQ ID NO:5. In some embodiments, the payload is the IBV nucleocapsid protein of SEQ ID NO:5. In some embodiments, the payload is a polynucleotide encoding a polypeptide at least 80%, at least 85%, at least 90%, at least 95%, at least 98%, or at least 99% to the IBV nucleocapsid protein of SEQ ID NO:5. In some embodiments, the payload is a polynucleotide encoding the IBV nucleocapsid protein of SEQ ID NO:5. In some embodiments, the payload comprises the polynucleotide of SEQ ID NO:6 or a sequence at least 90% identical thereto.

In some embodiments, the payload a polypeptide at least 80%, at least 85%, at least 90%, at least 95%, at least 98%, or at least 99% to the IBV truncated spike protein of SEQ ID NO:7. In some embodiments, the payload is the IBV truncated spike protein of SEQ ID NO:7. In some embodiments, the payload is a polynucleotide encoding a polypeptide at least 80%, at least 85%, at least 90%, at least 95%, at least 98%, or at least 99% to the IBV truncated spike protein of SEQ ID NO:7. In some embodiments, the payload is a polynucleotide encoding the IBV nucleocapsid protein of SEQ ID NO:7. In some embodiments, the payload comprises the polynucleotide of SEQ ID NO:8 or a sequence at least 90% identical thereto.

In some embodiments, the payload is a polypeptide antigen specific for Severe Acute Respiratory Syndrome Coronavirus 2 (SARS-CoV-2). SARS-CoV-2 includes the major structural proteins spike (S), envelope (E), membrane (M), and nucleocapsid (N). In some embodiments, the payload is selected from the group consisting of the SARS-CoV-2 S, E, M, and N proteins and fragments thereof. In some embodiments, the payload is a polynucleotide encoding the SARS-CoV-2 S, E, M, or N protein or fragments thereof. In some embodiments, the payload is a polypeptide at least 80%, at least 85%, at least 90%, at least 95%, at least 98%, or at least 99% to the SARS-CoV-2 nucleocapsid protein of SEQ ID NO:9. In some embodiments, the payload is the SARS-CoV-2 nucleocapsid protein of SEQ ID NO:9. In some embodiments, the payload is a polynucleotide encoding a polypeptide at least 80%, at least 85%, at least 90%, at least 95%, at least 98%, or at least 99% to the SARS-CoV-2 nucleocapsid protein of SEQ ID NO:9. In some embodiments, the payload is polynucleotide encoding the SARS-CoV-2 nucleocapsid protein of SEQ ID NO:9. In some embodiments, the payload comprises the polynucleotide of SEQ ID NO:10 or a sequence at least 90% identical thereto.

In some embodiments, the payload is a polypeptide at least 80%, at least 85%, at least 90%, at least 95%, at least 98%, or at least 99% to the SARS-CoV-2 truncated spike protein of SEQ ID NO:11. In some embodiments, the payload is the SARS-CoV-2 truncated spike protein of SEQ ID NO:11. In some embodiments, the payload is a polynucleotide encoding a polypeptide at least 80%, at least 85%, at least 90%, at least 95%, at least 98%, or at least 99% to the SARS-CoV-2 truncated spike protein of SEQ ID NO:11. In some embodiments, the payload is polynucleotide encoding the SARS-CoV-2 truncated spike protein of SEQ ID NO:11. In some embodiments, the payload comprises the polynucleotide of SEQ ID NO:12 or a sequence at least 90% identical thereto.

In some embodiments, the payload is functionalized prior to loading into the QAC complex. Proteins, DNA molecules, and RNA molecules that are negatively charged at neutral pH are generally readily taken up by QAC particles due to the electrostatic interactions between the negatively charged payload and the positively charged QAC particles. To improve the loading capacity of neutral and positively charged payloads, the payload may be functionalized to alter the surface charge of the payload. For example, chemical modifications such as amination of protein molecules can introduce negatively charged amino groups. Chemical modifications such as carboxylation of protein molecules can increase the number of free carboxylic acid groups on the protein surface to enhance loading of the protein into the QAC complex. The isoelectric point of the protein molecule can be reduced by protein surface modification with malonic acid moieties to increase interaction with the chitosan component of the QAC complex.

In some embodiments, the chitosan is functionalized. Chitosan may be functionalized with negatively charged sulfonate groups by reaction of the amino group of chitosan with 5-formyl-2-furan sulfonic acid (FFSA) followed by treatment using sodium borohydride to form a negatively charged chitosan surface. Use of the negatively charged chitosan in the formation of the QAC complex will generally be favorable for loading of positively charged payload molecules.

In some embodiments, the QAC complex is loaded with a DNA molecule payload. The QAC-DNA loaded complex is formed by mixing a solution of Quil-A and DNA into a solution of chitosan to form a final mixed solution including the QAC-DNA complex. In the final mixed solution, the Quil-A and the chitosan are present at a ratio of between 1:15 to 1:100. In some embodiments, the Quil-A and the chitosan are present at a ratio of about 1:20 (e.g., 1:15, 1:16, 1:17, 1:18, 1:19, 1:20, 1:21, 1:22, 1:23, 1:24, or 1:25) in the final mixed solution. In some embodiments, in the final solution Quil-A is at a concentration of 0.001% and chitosan is at a concentration between about 0.02% and about 0.1%. In some embodiments, the DNA payload in the DNA Quil-A solution is at a concentration between about 10 μg/ml and about 1000 μg/ml.

In some embodiments, the Quil-A DNA solution and the chitosan solution are mixed drop-wise. In some embodiments, the Quil-A DNA solution and the chitosan solution are mixed by vortex mixing for about 15-90 seconds (15 seconds, 20 seconds, 25 seconds, 30 seconds, 35 seconds, 40 seconds, 45 seconds, 50 seconds, 60 seconds, 70 seconds, 80 seconds or 90 seconds). In some embodiments, the Quil-A DNA solution and the chitosan solution are mixed drop-wise followed by vortex mixing for about 15-90 seconds (15 seconds, 20 seconds, 25 seconds, 30 seconds, 35 seconds, 40 seconds, 45 seconds, 50 seconds, 60 seconds, 70 seconds, 80 seconds or 90 seconds). The Quil-A DNA solution and the chitosan solution may be heated prior to mixing. In some embodiments, the Quil-A DNA solution and the chitosan solution are heated to a temperature between about 20° C. and about 60° C. (e.g., 20° C., 25° C., 30° C., 35° C., 40° C., 45° C., 50° C., 55° C., or 60° C.) for between about 20 to about 40 minutes (20 minutes, 25 minutes, 30 minutes, 35 minutes, or 40 minutes) prior to mixing. In some embodiments, after mixing the final solution is incubated at room temperature for about 1 hour to promote QAC complex formation. In some embodiments, after mixing the final solution is incubated for 1 hour at between about 20° C. and about 45° C. (e.g., 20° C., 21° C., 22° C., 23° C., 24° C., 25° C., 26° C., 27° C., 28° C., 29° C., 30° C., 31, 32° C., 33° C., 34° C., 35° C., 36° C., 37° C., 38° C., 39° C., 40° C., 41° C., 42° C., 43° C., 44° C., or 45° C.) with shaking at between about 90 rpm and about 150 rpm (e.g., 90 rpm, 95 rpm, 100 rpm, 105 rpm, 110 rpm, 115 rpm, 120 rpm, 125 rpm, 130 rpm, 135 rpm, 140 rpm, 145 rpm, or 150 rpm). The pH of the solutions may be between 5.5 and 7.0.

In some embodiments, a first solution of about 0.002% Quil-A and between about 1 μg/ml and about 5,000 μg/ml DNA in 50 mM sodium sulfate buffer and a second solution of about 0.04% chitosan in 5 mM sodium acetate buffer pH5.5 are each heated at 55° C. for about 30 min. Equal volumes of the first and second solution are mixed dropwise then vortex mixed for about 30 s followed by incubation at room temperature for about 1 hour to form the QAC DNA loaded complex.

In some embodiments, the QAC complex is loaded with a protein molecule payload. The QAC-protein loaded complex is formed by mixing a solution of Quil-A and protein into a solution of chitosan to form a final mixed solution including the QAC-protein complex. In the final mixed solution, the Quil-A and the chitosan are present at a ratio of between 1:15 to 1:100. In some embodiments, the Quil-A and the chitosan are present at a ratio of about 1:20 (e.g., 1:15, 1:16, 1:17, 1:18, 1:19, 1:20, 1:21, 1:22, 1:23, 1:24, or 1:25) in the final mixed solution. In some embodiments, in the final solution Quil-A is at a concentration of 0.001% and chitosan is at a concentration between about 0.02% and about 0.1%. In some embodiments, the protein payload in the protein Quil-A solution is at a concentration between about 10 μg/ml and about 1000 μg/ml.

In some embodiments, the Quil-A protein solution and the chitosan solution are mixed drop-wise. In some embodiments, the Quil-A protein solution and the chitosan solution are mixed by vortex mixing for about 15-90 seconds (15 seconds, 20 seconds, 25 seconds, 30 seconds, 35 seconds, 40 seconds, 45 seconds, 50 seconds, 60 seconds, 70 seconds, 80 seconds or 90 seconds). In some embodiments, the Quil-A protein solution and the chitosan solution are mixed drop-wise followed by vortex mixing for about 15-90 seconds (15 seconds, 20 seconds, 25 seconds, 30 seconds, 35 seconds, 40 seconds, 45 seconds, 50 seconds, 60 seconds, 70 seconds, 80 seconds or 90 seconds). The Quil-A protein solution and the chitosan solution may be heated prior to mixing. In some embodiments, the Quil-A protein solution and the chitosan solution are heated to a temperature between about 20° C. and about 60° C. (e.g., 20° C., 25° C., 30° C., 35° C., 40° C., 45° C., 50° C., 55° C., or 60° C.) for between about 20 to about 40 minutes (20 minutes, 25 minutes, 30 minutes, 35 minutes, or 40 minutes) prior to mixing. In some embodiments, after mixing the final solution is incubated at room temperature for about 1 hour to promote QAC complex formation. In some embodiments, after mixing the final solution is incubated for 1 hour at between about 20° C. and about 45° C. (e.g., 20° C., 21° C., 22° C., 23° C., 24° C., 25° C., 26° C., 27° C., 28° C., 29° C., 30° C., 31, 32° C., 33° C., 34° C., 35° C., 36° C., 37° C., 38° C., 39° C., 40° C., 41° C., 42° C., 43° C., 44° C., or 45° C.) with shaking at between about 90 rpm and about 150 rpm (e.g., 90 rpm, 95 rpm, 100 rpm, 105 rpm, 110 rpm, 115 rpm, 120 rpm, 125 rpm, 130 rpm, 135 rpm, 140 rpm, 145 rpm, or 150 rpm). The pH of the solutions may be between 5.5 and 7.0.

In some embodiments, a first solution of about 0.002% Quil-A and between about 1 μg/ml and about 5,000 μg/ml protein in 50 mM sodium sulfate buffer and a second solution of about 0.04% chitosan in 5 mM sodium acetate buffer pH5.5 are each heated at 55° C. for about 30 min. Equal volumes of the first and second solution are mixed dropwise then vortex mixed for about 30 s followed by incubation at about 37° C. for about 1 hour with shaking at about 110 rpm to form the QAC protein loaded complex.

A vaccine comprising a QAC complex adjuvant as described herein may also comprise other suitable agents or ingredients. Suitable agents may include a suitable carrier or vehicle for delivery. As used herein, the term “carrier” refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the U.S. Pharmacopeia National Formulary, 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer’s solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

In another embodiment, the present formulation may also comprise other suitable agents such as a stabilizing delivery vehicle, carrier, support or complex-forming species. The coordinate administration methods and combinatorial formulations of the instant invention may optionally incorporate effective carriers, processing agents, or delivery vehicles, to provide improved formulations for delivery of the QAC complex and other biologically active agents and antigens of the composition.

The vaccine formulation may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the vaccine formulation, more preferably about 0.001-1% (w/v). Other excipients, if desired, may be included as part of the final vaccine formulation.

The remainder of the vaccine formulation may be an acceptable diluent, to 100%, including water. The vaccine formulation may also be formulated as part of a water-in-oil, or oil-in-water emulsion.

The vaccine formulation may be separated into vials or other suitable containers. The vaccine formulation herein described may then be packaged in individual or multi-dose ampoules, or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user, and administered to a patient.

The term “lyophilization” or “lyophilized,” as used herein, refers to freezing of a material at low temperature followed by dehydration by sublimation, usually under a high vacuum. Lyophilization is also known as freeze drying. Many techniques of freezing are known in the art of lyophilization such as tray-freezing, shelf-freezing, spray-freezing, shell-freezing and liquid nitrogen immersion. Each technique will result in a different rate of freezing. Shell-freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray-freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray-freezing into liquid, dropping by ~20 μl droplets into liquid $N_2$, spray-freezing into vapor over liquid, or by other techniques known in the art.

The vaccine of the present invention may be either in a solid form or in a liquid form. Preferably, the vaccine of the present invention may be in a liquid form. The liquid form of the vaccine may have a concentration of about 0.5-20 μg/ml Quil-A and about 100-250 μg/ml chitosan. In some embodiments, the liquid form of the vaccine includes 10 μg/ml Quil-A and 200 μg/ml chitosan. The liquid form of the vaccine may have a concentration of about 10-1000 μg/ml DNA payload or 5-500 μg/ml RNA payload.

To vaccinate a patient, a therapeutically effective amount of vaccine comprising the QAC complex adjuvant or a QAC complex loaded with a payload antigen or immunogen may be administered to a patient. The therapeutically effective amount of vaccine may typically be one or more doses, preferably in the range of about 0.01-10 mL, most preferably 0.1-1 mL, containing 1-200 micrograms, most preferably 1-100 micrograms of vaccine formulation/dose. The therapeutically effective amount may also depend on the vaccination species. For example, for smaller animals such as mice, a preferred dosage may be about 0.01-1 mL of a 1-50 microgram solution of antigen. For a human patient, a preferred dosage may be about 0.1-1 mL of a 1-50 microgram solution of antigen. The therapeutically effective amount may also depend on other conditions including characteristics of the patient (age, body weight, gender, health condition, etc.), characteristics of the antigen or pathogen of interest, and others. In one embodiment the vaccine formulation of the present invention comprises the QAC complex adjuvant or a QAC complex loaded with a payload antigen or immunogen with Quil-A at a concentration of 10 μg/ml and chitosan at a concentration of 200 μg/ml.

A vaccine of the present invention may be administered by using any suitable means as disclosed above. Preferably, a vaccine of the present invention may be administered by intranasal delivery, transmucosal administration, subcutaneous or intramuscular administration, e.g., needle injection. In some embodiments, vaccine compositions for protection against a viral infection are formulated for transmucosal delivery. In some embodiments, vaccine compositions for protection against a bacterial infection are formulated for subcutaneous administration.

After vaccination using a vaccine of the present invention comprising the QAC complex adjuvant, a patient may be immunized against at least one type of fungi, bacteria, or virus. In one specific embodiment, a patient after vaccination may be immunized against at least one species of bacteria. In one preferred embodiment, a patient after vaccination may be immunized from *Mycobacterium avium* subspecies paratuberculosis, *Mycobacterium bovis, Mycobacterium tuberculosis*, and *Mycobacterium avium* sub species *avium.*

The instant invention may also include kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains the QAC complex adjuvant or a QAC complex loaded with a payload antigen or immunogen with mucosal or subcutaneous delivery enhancing agents disclosed herein formulated in a pharmaceutical preparation for delivery. In some embodiments, the kit includes a Quil-A solution as described herein and a chitosan solution as described herein for the preparation of QAC complex using a user supplied payload molecule.

As used herein, the term "pharmaceutically acceptable carrier" refers to any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

In one embodiment, the composition may also comprise suitable stabilizing delivery vehicle, carrier, support or complex-forming species, such as those as discussed above. For example, the composition may additionally comprise at least one of a stabilizer, a buffer, or an adjuvant.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates the preparation of loaded Quil-A chitosan complexes.

Infectious Bronchitis (IB) is an acute respiratory illness of domestic fowl caused by Infectious Bronchitis Virus (IBV) (1). IBV is a member of the genus gammacoronavirus, family Coronaviridae, order Nidovirales with a 27.6 Kb single stranded positive sense RNA genome encoding major structural proteins, spike glycoprotein (S), envelope (E), membrane (M) and nucleocapsid (N) (2). D3 associated clinical signs include tracheal rales, frequent sneezing with nasal exudate, lethargy, labored breathing, etc. Uncomplicated IB infections are not lethal and virus with associated symptoms are cleared within 10 days (3). Apart from replicating and causing pathology in the upper respiratory tract, IBV can also affect the oviducts and kidneys depending on the strain of the virus. IBV control is of great economic importance to the poultry industry, infected broilers are subjected to increased condemnation at the slaughterhouses and layers are plagued with a drop in egg quality and production (4-6). High antigenic variation in the spike glycoprotein (S) is a hallmark of different IBV serotypes (6-8). Multiple serotypes co-circulate in birds, which complicates diagnosis and control of IBV. Current commercial modified live virus (MLV) vaccines confer homologous protection but fail to cross-protect against multiple and newly emerging serotypes. Sequence difference even as little as 4% in the 51 subunit of S protein can lead to vaccine failure (9, 10). Unfortunately, MLVs have been shown to persist and transmit in vaccinated birds potentially mediating recombination with virulent circulating serotypes leading to the emergence of new serotypes (11-13). With the emergence of new serotypes like GA98 linked to the excessive use of MLV (14), there is an urgent need to develop a safe and effective vaccine against IBV, the focus of the current study.

The use of plasmid DNA as potential immunogens was described almost 30 years ago (15), however, only 5 DNA-based vaccines have been licensed for veterinary use (16). Nucleic acid based vaccines have significant advantages over MLV as they have a superior safety profile, invoke robust cell mediated immunity (CMI) with potent adjuvants, cost less to produce and are thermostable obviating the need for cold chain (17). DNA-based vaccines encoding IBV 51, M and N genes administered in ovo and intramuscularly have been studied with variable protection levels against IBV (18-26). The use of plasmid DNA vaccines in the field despite having practical advantages and being safe has been limited owing to poor immunogenicity and cellular availability. Nanocarriers increase bioavailability of antigen cargo generating an immediate uptake by immune cells and hence, are potent adjuvants(27). Nanocarriers can protect plasmid DNA and antigen cargo from degradation in vivo facilitating delivery in vaccine hostile mucosal surfaces (28, 29). To provide a safer alternative to current MLVs, we detail the development of nano carriers composed of natural adjuvants, Quil-A and chitosan (QAC) for the delivery of IBV plasmid DNA immunogen. Natural adjuvants (such as Quil-A and chitosan) are inexpensive to produce, making them ideal candidates for animal vaccines. Chitosan is a nontoxic, biodegradable, biocompatible natural polysaccharide. Chitosan is cationic in nature and can readily complex with negatively charged nucleic acids and proteins through electrostatic interactions (30). Chitosan is immunomodulatory, forms stable DNA/protein complexes and has mucoadhesive properties because of which they are widely applied for mucosal routes of administration(31). Quil-A is a potent adjuvant with mild surfactant properties (32) produced from the plant *Quillaja saponaria*, which can form nanoparticle compounds like ISCOMs and those formed with chitosan (QAC) as we detail below.

The sequence similarity of IBV Nucleocapsid (N) protein between diverse serotypes is greater than 90%, for this reason IBV N protein is an ideal immunogen candidate in an effort to develop a cross-protective vaccine. Immunization with N protein elicited a robust cytotoxic T-lymphocyte (CTL) response, an important correlate of protection against IBV (20, 33, 34). Adoptively transferred IBV reactive CD8+ T-cells protect against IBV challenge in naïve chickens (35, 36). In the present study, we evaluated the ability of a stable plasmid DNA construct expressing the IBV N protein complexed with the QAC adjuvant system given intra nasally to protect immunized birds against challenge with virulent strain of IBV. Our results indicate that pQAC-N vaccine elicits a CD8+ T-cell response which protect vaccinated birds against IBV challenge. Levels of protection in pQAC-N vaccinated birds were higher when compared to unadjuvanted or chitosan complexed plasmid DNA vaccine. Our data demonstrate that intra nasal immunization with pQAC-N induced a strong cell mediated immune response that protect vaccinated birds with a significant reduction in clinical signs and viral load to levels seen with commercial MLV vaccinated birds.

Results

Figures 18A, 18B, 18C, 18D:
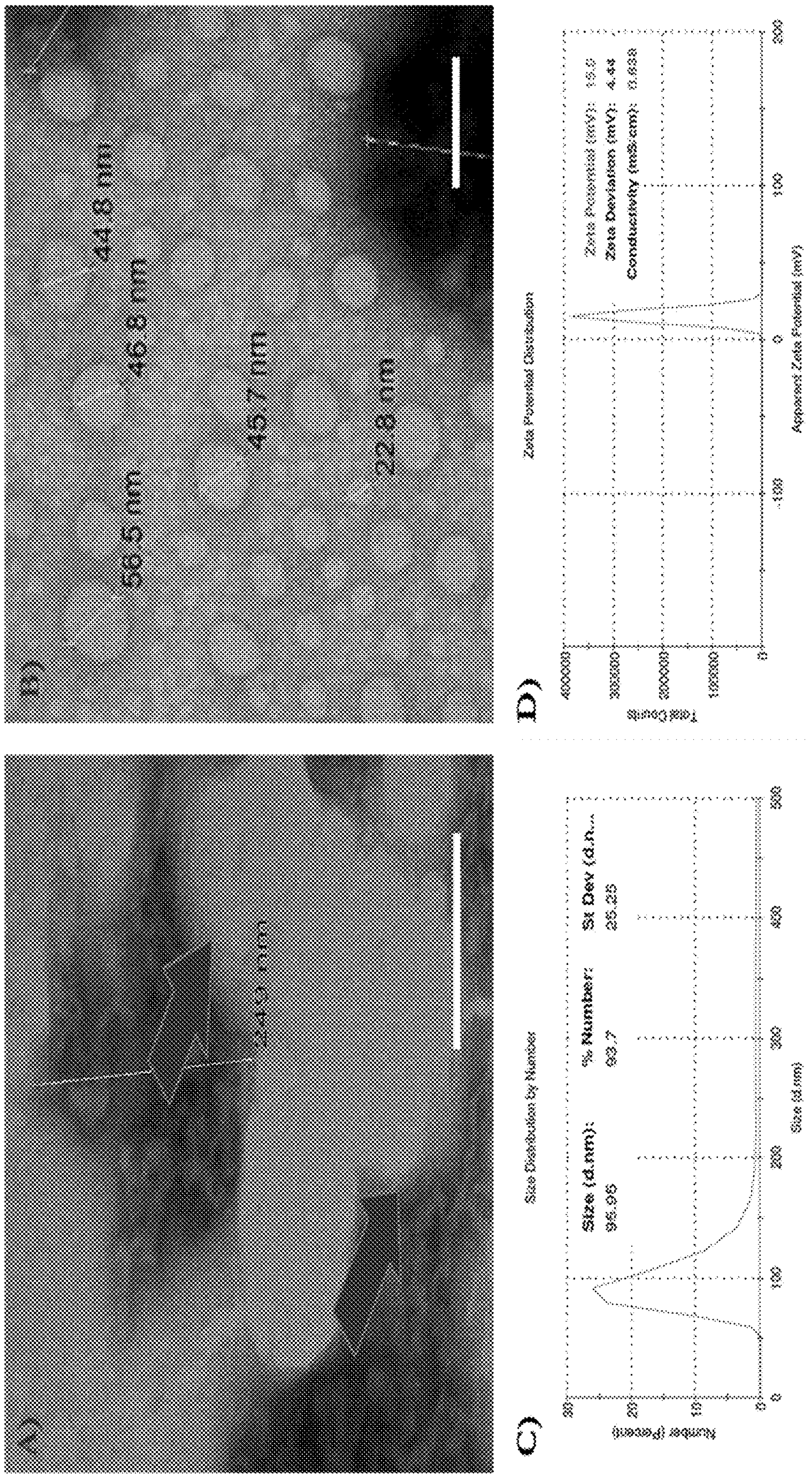
FIGS. 18A-18D show the nano structure of QAC adjuvant system. A) Aggregates of chitosan-pCAG-GFP preparation (arrows) were seen with TEM. B) Nanoparticles of QAC-pCAG-GFP preparation (arrows) with TEM. Scale bar=100 nm. C) Number-based DLS data and (D) Zeta potential on QAC-pCAG-GFP nanoparticles at 25° C. with Zetasizer® software.

Synthesis and characterization of pQAC-N nanovaccine. The green fluorescent protein (GFP) gene was inserted into the pCAG plasmid and was used as a DNA pay load for nanoparticle (NP) characterization. Transmission electron microscopy (TEM) analysis of chitosan-plasmid DNA complexes indicated presence of aggregated structures (FIG. 18A). However, when Quil-A was added to chitosan-DNA complex, defined particles were formed with the disaggregation of chitosan-DNA complexes (FIG. 18B). Size estimations using TEM analysis indicated that QAC-DNA nanoparticles were <100 nm (FIG. 18B). Dynamic light scattering (DLS) was also used to measure the hydrodynamic size and zeta potential of QAC-pDNA particles. As expected, particles were 95±25 nm in size (94%) with a net positive zeta potential of 15±4.44 mV (FIGS. 18C-18D).

Figure 19A:
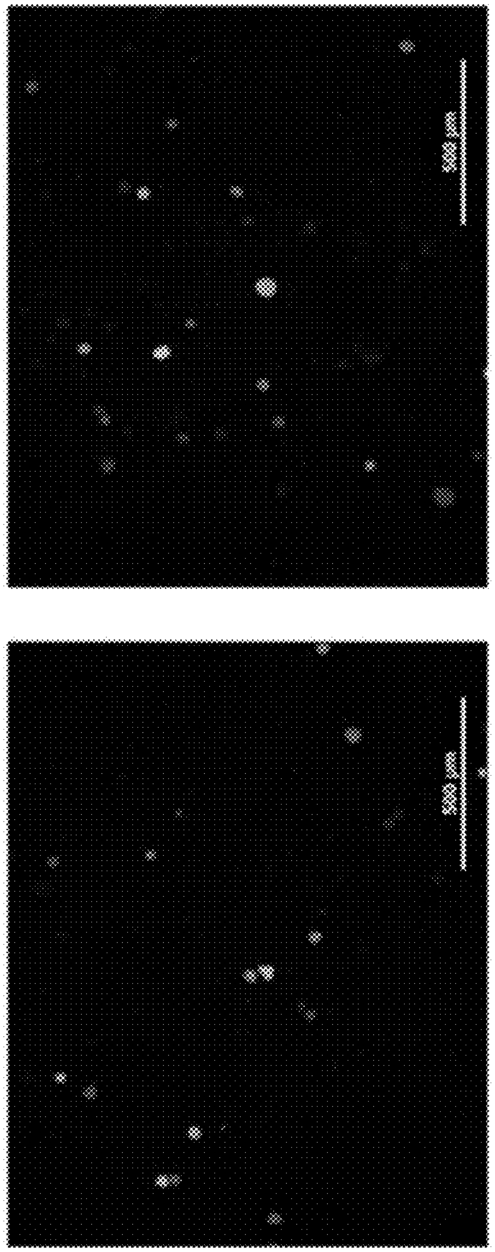
FIGS. 19A-19B show QAC nanoparticle payload delivery and release. (A) GFP+Expi293F cells post addition of QAC-pCAG-GFP (B) Sustained release kinetics observed in vitro.
Figure 19B:
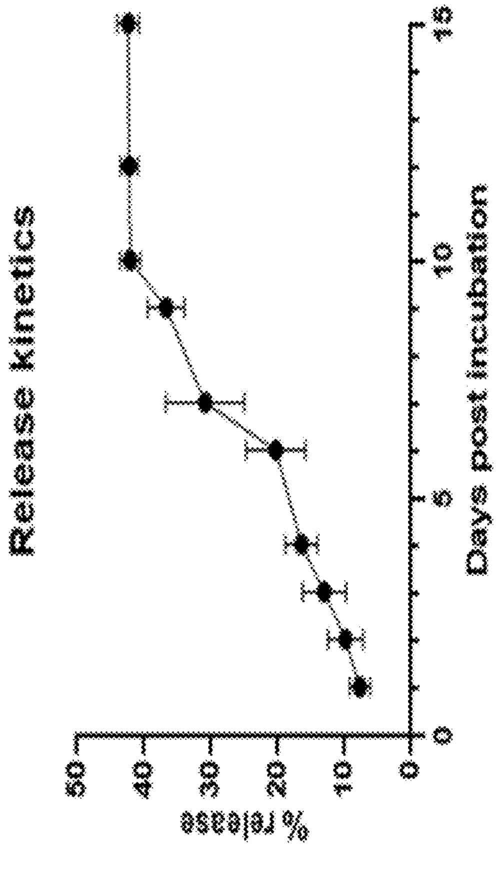

The ability of QAC adjuvant system to deliver plasmid DNA payload was evaluated in vitro to examine its potential for immunization programs. The QAC nanoparticles encapsulating total 5 ug pCAG-GFP construct were added to a suspension of Expi293F cells. After 72 hrs post addition, presence of fluorescent cells was observed using fluorescence microscopy (FIG. 19A), indicating the delivery and expression of the GFP from the construct. The release kinetics of the GFP protein from the pCAG-GFP construct was evaluated in phosphate buffered saline (PBS) at pH 7.4 by quantifying the amount of starting and released plasmid DNA in buffer using spectrophotometry. The analysis showed that almost 42% of plasmid DNA within the nanoparticles was released within 15 days, the end point for our analysis. Overall, a biphasic release kinetics was observed with sustained release of DNA cargo for the first 10 days followed by a plateau over the next 5 days (FIG. 19B). The encapsulation efficiency of DNA (percentage of encapsulated DNA relative to the starting DNA) in QAC nanoparticles ranged from 70-90%.

Figure 20A:
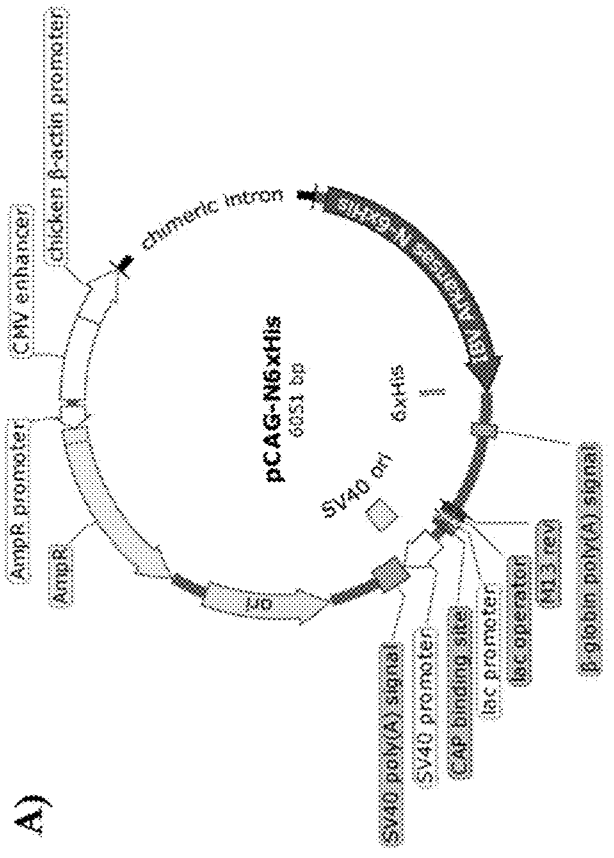
FIGS. 20A-20B show DNA vaccine construct. A) Plasmid map of pCAG-IBV Ark N, 6×His construct (pQAC-N) generated using Snapgene software. B) Western blot analysis with anti 6×His-HRP antibody confirming expression of N6×His from pCAG-N6×His plasmid. Lanes are as follows. Supernatant (lane 2) and pellet (lane 4) from Expi293F cells transfected with control pCAG plasmid, Supernatant (lane 1) and pellet (lane 3) from Expi29F3 cells transfected with pCAG-N6×His plasmid and purified N6×His protein (lane 5).
Figure 20B:
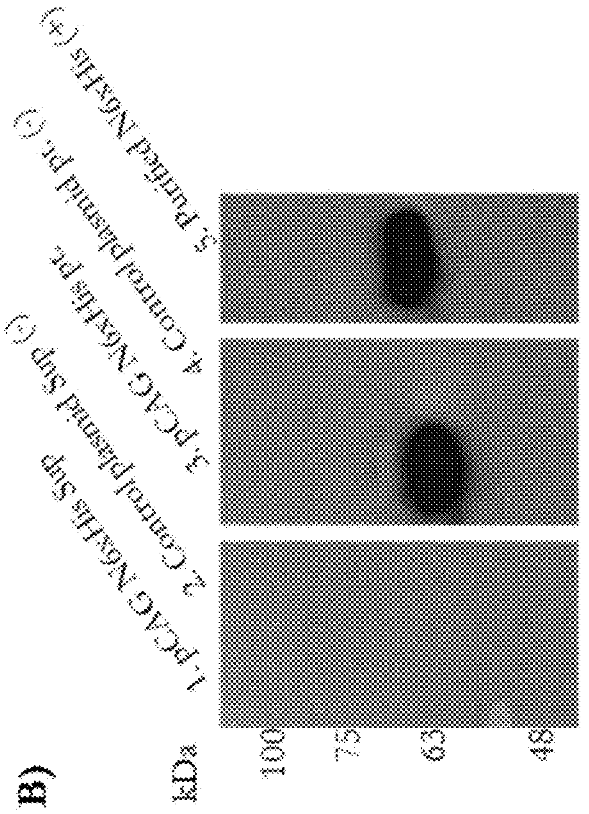

Finally, following successful encapsulation and sustained release of plasmid DNA with QAC, we used the same nanocarrier (QAC) to encapsulate plasmid DNA encoding N protein from IBV-Arkansas strain with a C-terminal 6×His tag, henceforth referred to as pQAC-N. The expression of antigen was confirmed using western blot analysis with an anti-6×His antibody (FIGS. 20A-20B).

Figures 21A, 21B:
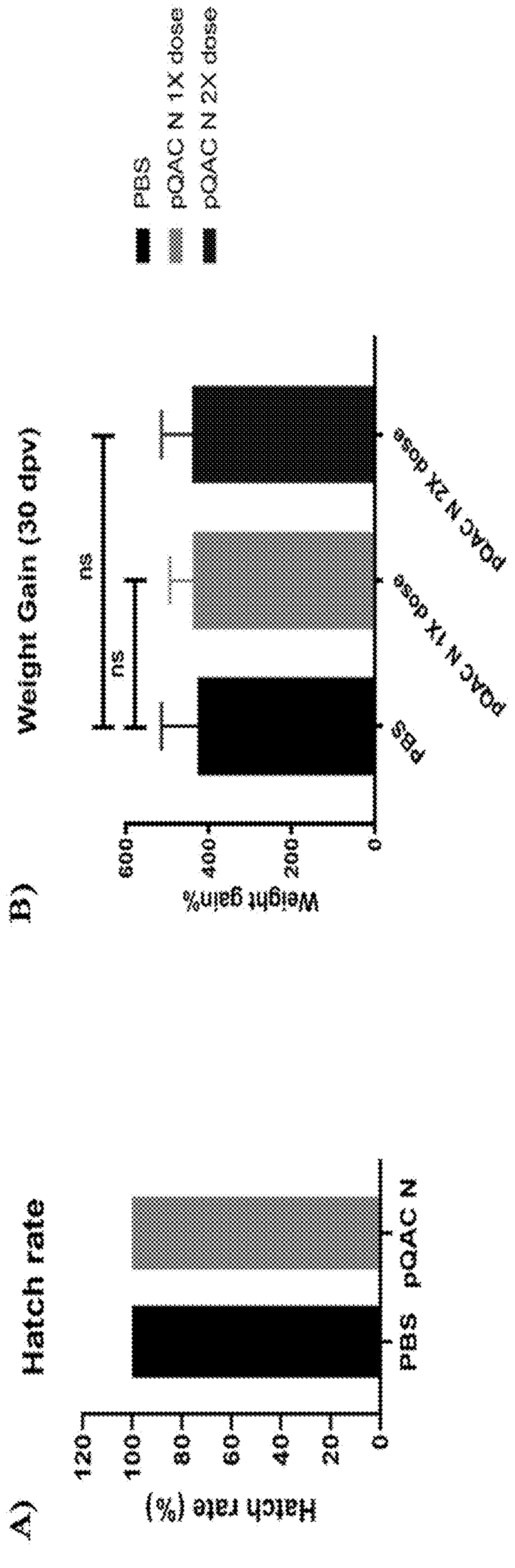
FIGS. 21A-21B show safety of pQAC-N. A) Hatch rate % in ECEs inoculated with pQAC-N vaccine. B) Weight gain of chicks immunized with pQAC N construct after 30 days post vaccination (dpv). Data show means±SD. Significance (*, $P<0.05$) or non-significance (ns) was determined by one-way ANOVA with multiple comparisons.

QAC-based nanovaccine is well tolerated by chickens—In ovo and spray vaccinations (intranasal) are two strategies used in the field for mass vaccinations of poultry flocks. The safety of pQAC-N in chicken hosts was evaluated through two routes of administration, In ovo and intranasal, a proxy for field spray vaccinations. Embryo development and hatch rate of pQAC-N (100 ug) inoculated specific pathogen free (SPF) embryonated chicken eggs (ECE) was similar to ECEs inoculated with PBS (100%, FIG. 21A). In addition, 1-day-old SPF chicks were immunized with pQAC-N construct intra nasally and monitored for general or respiratory distress, depression or in appetence and weight gain over the course of 30 days post vaccination. No signs for respiratory distress were observed in chicks immunized at 1 day of age and weight gain over 30 days was not statistically different from chicks inoculated with PBS (FIG. 21B). Overall, our analysis in chickens and chicken embryos indicated that pQAC-N is well-tolerated.

Figures 22A, 22B:
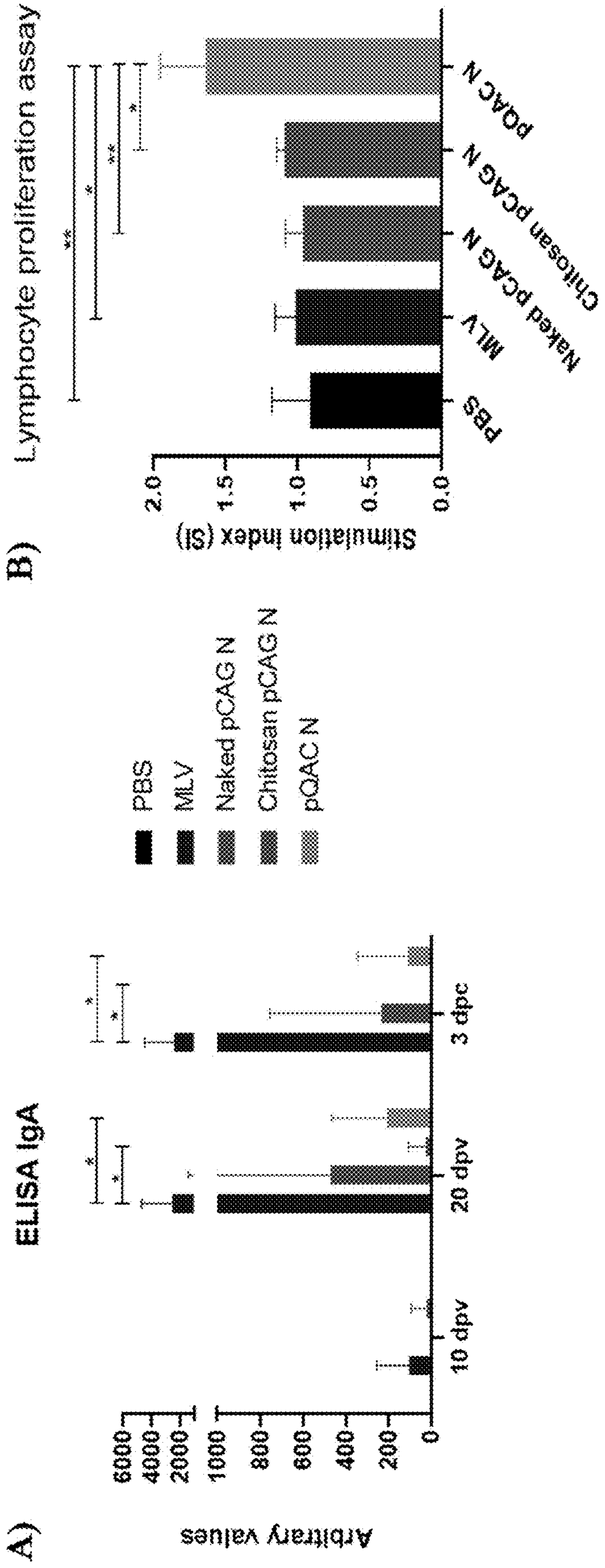
FIGS. 22A-22B show pQAC-N vaccine immunogenicity. Groups of white leghorn SPF chicks were either unvaccinated (PBS) or immunized with MLV (day-1) or naked unadjuvanted pCAG-N or Chitosan complexed pCAG-N or pQAC-N vaccine (100 ug pQAC-N) at day-1 and day-14. (A) IBV specific IgA in tears, significance (*, $P<0.05$) was determined by two-way ANOVA and (B) lymphocyte proliferation assay on PBMCs harvested at day 20 post vaccination, significance (*, $P<0.05$; **, $P<0.01$) or non-significance (ns) was determined by one-way ANOVA with multiple comparisons. Data show means±SD.

Immunization with pQAC-N induces a robust immune response—Harderian glands play a critical role in the control of IBV infection in the upper respiratory tract by secreting IBV specific IgA antibodies into the lachrymal fluid (tears) (34). Accordingly, we examined the ability of pQAC-N vaccine to elicit IBV specific immune responses in birds following intranasal delivery. Lachrymal fluid samples collected at different time points, 10, 20 days post vaccination (DPV, pre-challenge) and 3 days post challenge (DPC) were examined using ELISA plates coated with IBV Arkansas 51 and N proteins. IBV specific IgA titers were detectable in pQAC-N immunized birds at 20 DPV at levels higher than seen in chitosan pCAG-N immunized birds (FIG. 22A). Albeit detectable, IgA levels were not significantly higher than levels seen in other groups, naked (unadjuvanted) and chitosan complexed pCAG-N. IgA levels were 10 folds higher in birds immunized with commercial MLV when compared to other experimental vaccine groups (FIG. 22A), most likely because of the IgA against 51 which was not included in the pQAC-N but present in MLV.

To assess the effect of IBV specific cellular immune responses induced by pQAC-N, we measured the ability of PBMCs from immunized chickens to respond to IBV antigen stimulation. PBMCs were harvested from vaccinated birds at 20 DPV (pre-challenge time point) and processed for antigen specific cell proliferation assay (MTT assay). The stimulation of PBMCs from chickens vaccinated with pQAC-N resulted in significantly higher proliferation ($p<0.05$) than that of PBMCs from other groups including MLV (FIG. 22B), suggesting a better cellular immunity following pQAC-N immunization.

Figures 23A, 23B:
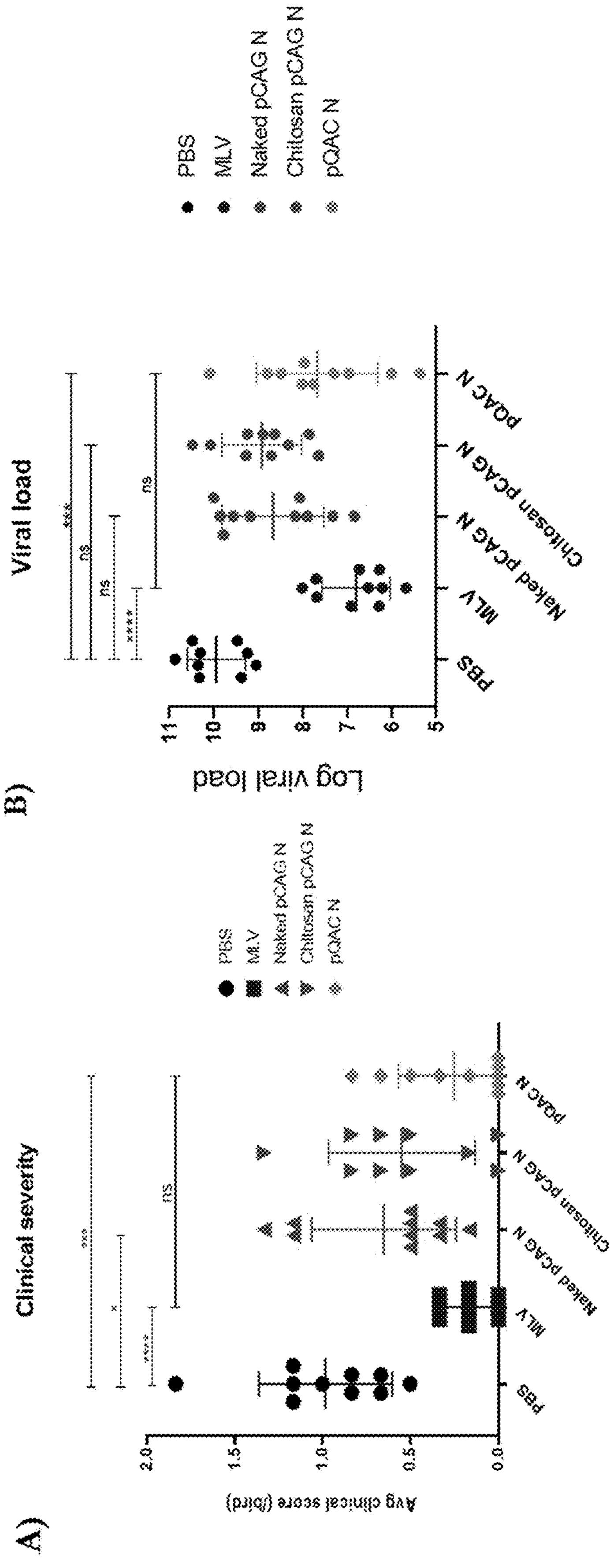
FIGS. 23A-23B show protective efficacy of pQAC-N vaccine. Groups of white leghorn SPF chicks were either unvaccinated (PBS) or immunized with MLV (day-1) or naked pCAG-N or Chitosan pCAG-N or pQAC-N vaccine (100 ug) at day-1 and day-14. (A) Clinical sign severity represented as average score/bird over 8 days post challenge in each group (B) IBV log viral load/10 ul lachrymal fluid at 6 days post challenge. Significance (*, $P<0.05$; , $P<0.01$; *, $P<0.001$; ****, $P<0.0001$) or non-significance (ns) was determined by one-way ANOVA with multiple comparisons. Data show means±SD.

Reduced clinical severity and viral burden in immunized birds—To investigate the protective efficacy of pQAC-N vaccine, all immunized birds were challenged with virulent IBV Arkansas-DPI serotype at 3 weeks post first vaccination (21 DPV) and the clinical severity of bird groups was scored up to 8 DPC (FIG. 23A). Vaccination with naked pCAG-N (unadjuvanted) and chitosan complexed pCAG-N conferred partial protection against clinical signs associated with IBV. On the other hand, pQAC-N and commercial MLV immunized bird groups were relatively asymptomatic with a significant reduction in clinical severity when compared to unvaccinated birds (FIG. 23A).

In addition, we used RT-qPCR to assess the level of viral RNA in lachrymal fluid of all birds at 6 DPC. A significant reduction in viral load (~2.5 logs) was found in the pQAC-N immunized birds when compared to control birds at levels comparable to commercial MLV vaccinated birds (FIG. 23B). A partial reduction in viral load was also observed in naked pCAG-N and chitosan pCAG-N administered birds (FIG. 23B). Overall, reduction in viral load was higher in the pQAC-N than other DNA-based vaccine constructs suggesting an important role played by Quil-A in the induced immunity in chickens.

Figures 24A, 24B, 24C, 24D:
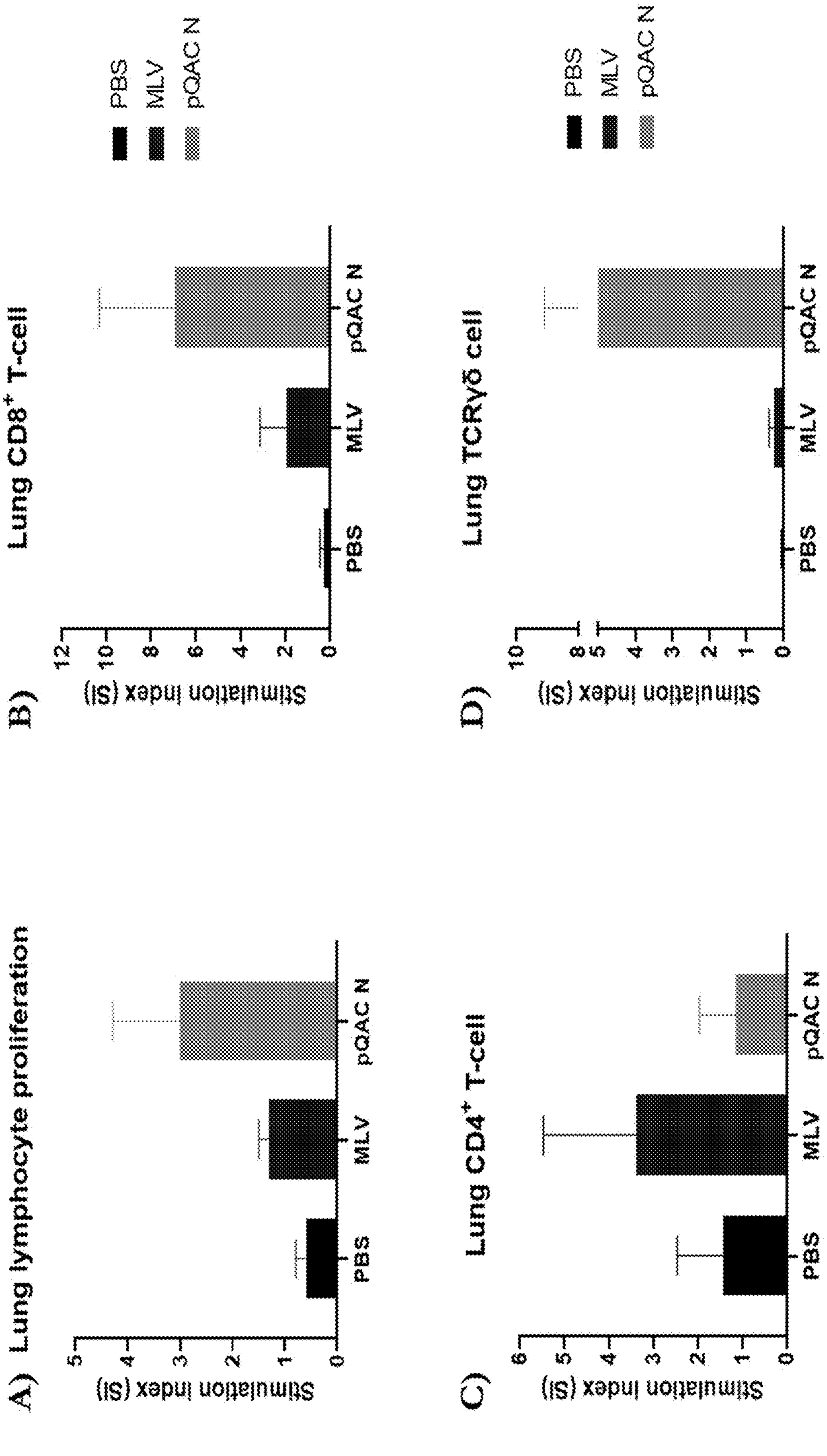
FIGS. 24A-24D show pQAC-N induces a robust T-cell response. (A) Lung cell proliferative capacity measured by CellTrace Violet dye dilution in unvaccinated, MLV and pQAC N vaccinated chickens. Proliferation was measured in (A) total lung cells, (B) CD8α+, (C) CD4+ and (D) TCRγδ+ lung T cells after 4 days in culture post antigen stimulation.

Localized IBV-specific cellular responses in immunized birds—Induction of robust T-cell responses has been identified as relevant correlates of protection against IBV infection in previous studies (34). An antigen specific T cell proliferation assay based on CellTrace™ Violet Cell dye staining of lung cells to trace proliferating T cells was developed. Different T-cell subsets responding to antigen stimulation was identified using flow cytometry assisted T-cell assay. Twenty days after first vaccination, the IBV Ark N protein specific proliferation was measured. The stimulation index (SI), which is the fold increase in stimulated to unstimulated cells calculated. Lung cells from pQAC-N vaccinated birds responded well to antigen stimulation which was higher when compared to negative and MLV control groups (FIG. 24A). An increase in the stimulation of proliferating CD8+ and TCRγδ+ T cells was observed in pQAC-N vaccinated birds in comparison to control birds (FIGS. 24B & 24D), suggesting a potential role for $CD8^+$ and $TCR\gamma\delta^+$ cell in pQAC-N immunity. On the other hand, the CD4+ T-cell proliferation was higher in MLV vaccinated birds (FIG. 24C).

Figures 25A, 25B, 25C:
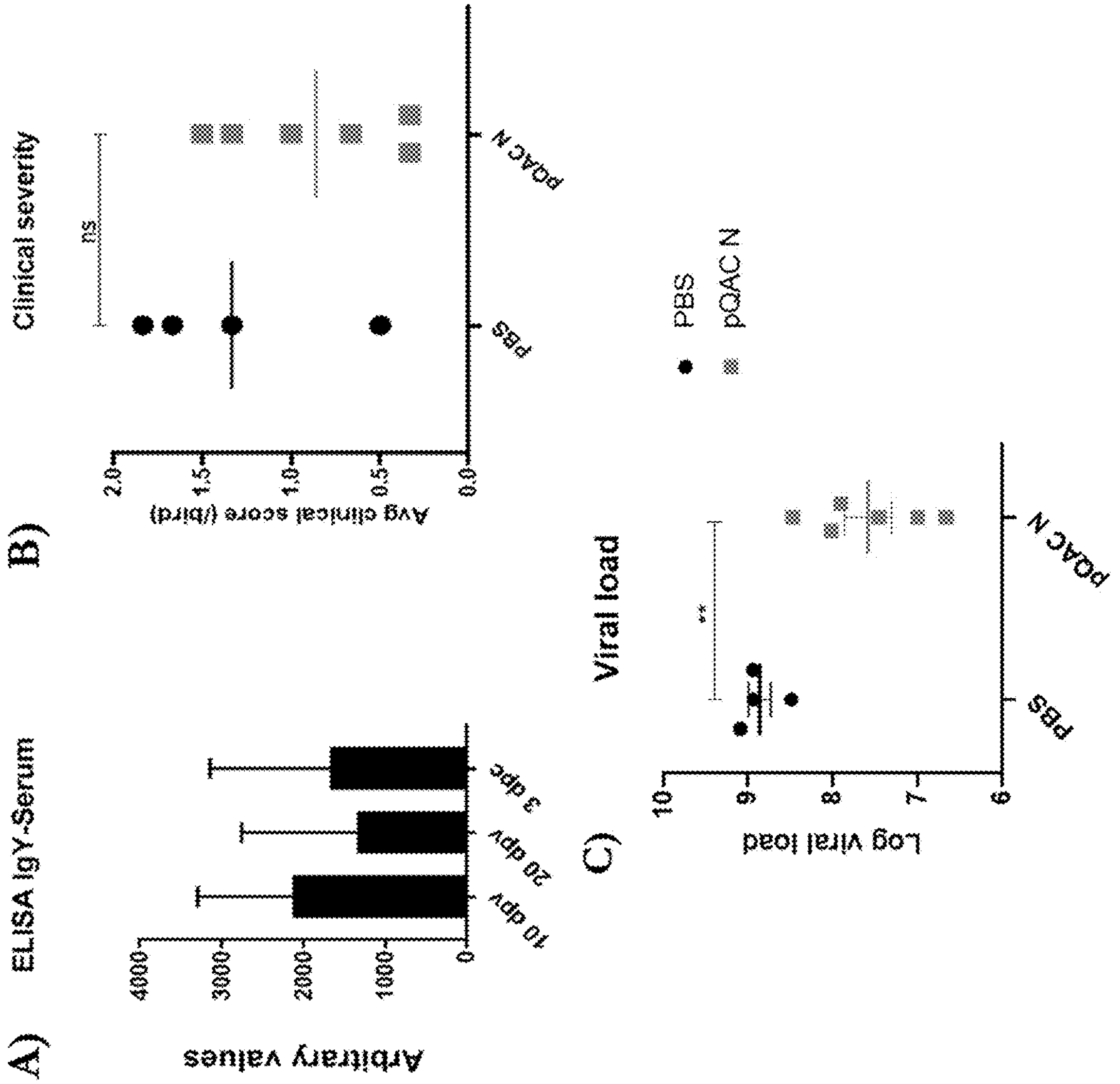
FIGS. 25A-25C show protective efficacy of pQAC-N vaccine in commercial birds. Groups of commercial white leghorn chicks were either unvaccinated (PBS) or immunized with pQAC N vaccine (100 ug) at day-1 and day-14. (A) Serum IgY ELISA titres indicating presence of high levels of MDA (B) Clinical sign severity represented as average score/bird over 8 days post challenge in each group (C) IBV log viral load/10 ul lachrymal fluid at 6 days post challenge. Significance (*, $P<0.05$; **, $P<0.01$) or non-significance (ns) was determined by unpaired t test. Data show means±SD.

Protective efficacy of pQAC-N in the presence of maternally derived antibodies—Maternally derived antibodies (MDA), mainly IgY are transferred from vaccinated hens to progeny via the yolk. Presence of IBV specific MDA has shown to protect against IBV challenge in SPF chickens (37-39). Although effective against IBV infections, MDA can interfere with MLV vaccination and dampen development of active immunity (39). In this pilot study, we investigated the ability of pQAC-N to mediate protection in the presence of interfering MDA. Commercial white leghorn chicks with high levels of circulating IBV specific IgY which persisted till about day-24 of age was used (FIG. 25A). As seen with the SPF chick, pQAC-N immunized commercial birds were also protected against IBV Arkansas DPI challenge with a significant reduction in viral load (FIG. 25C) and clinical severity scores (FIG. 25B) compared to unvaccinated birds, suggesting the ability of the pQAC-N to protect birds without interference by MDA.

Figure 26A:
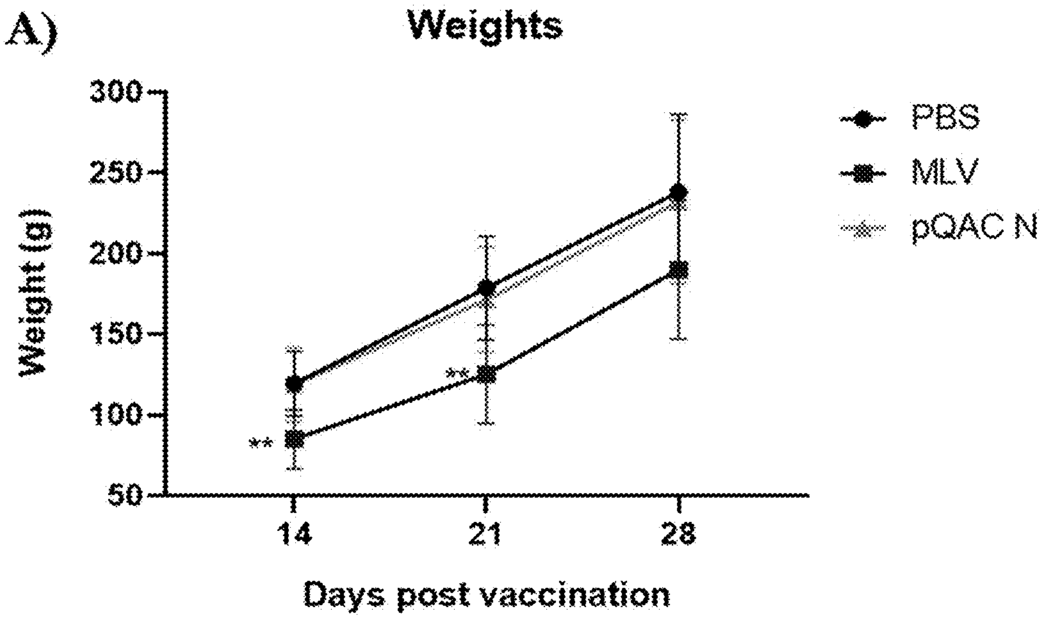
FIGS. 26A-26B show reduced weight gain in MLV vaccinated commercial birds. Groups of commercial white leghorn chicks were either unvaccinated (PBS) or immunized with MLV (day-1) or pQAC N vaccine (100 ug) at day-1 and day-14. (A) Absolute weight of birds in grams at 14, 21 and 28 dpv, significance (**, $P<0.01$) was determined by two-way ANOVA and compared with both PBS and pQAC N groups (B) Percentage weight gain of birds between 14 and 28 dpv. Data show means±SD.
Figure 26B:
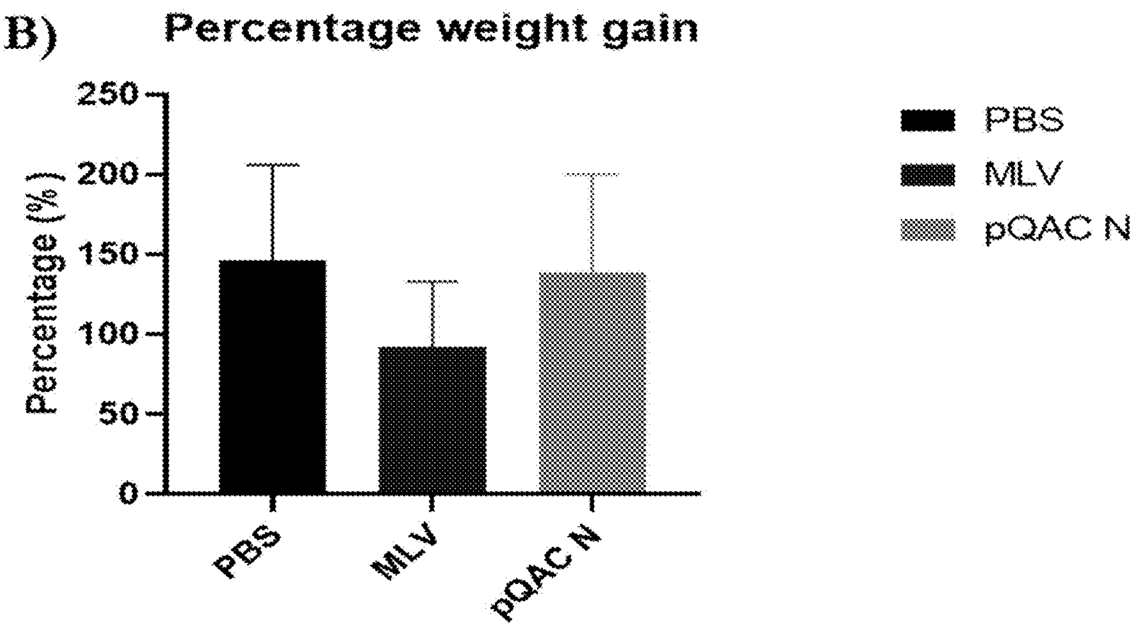
Figures 27A, 27B, 27C, 27D:
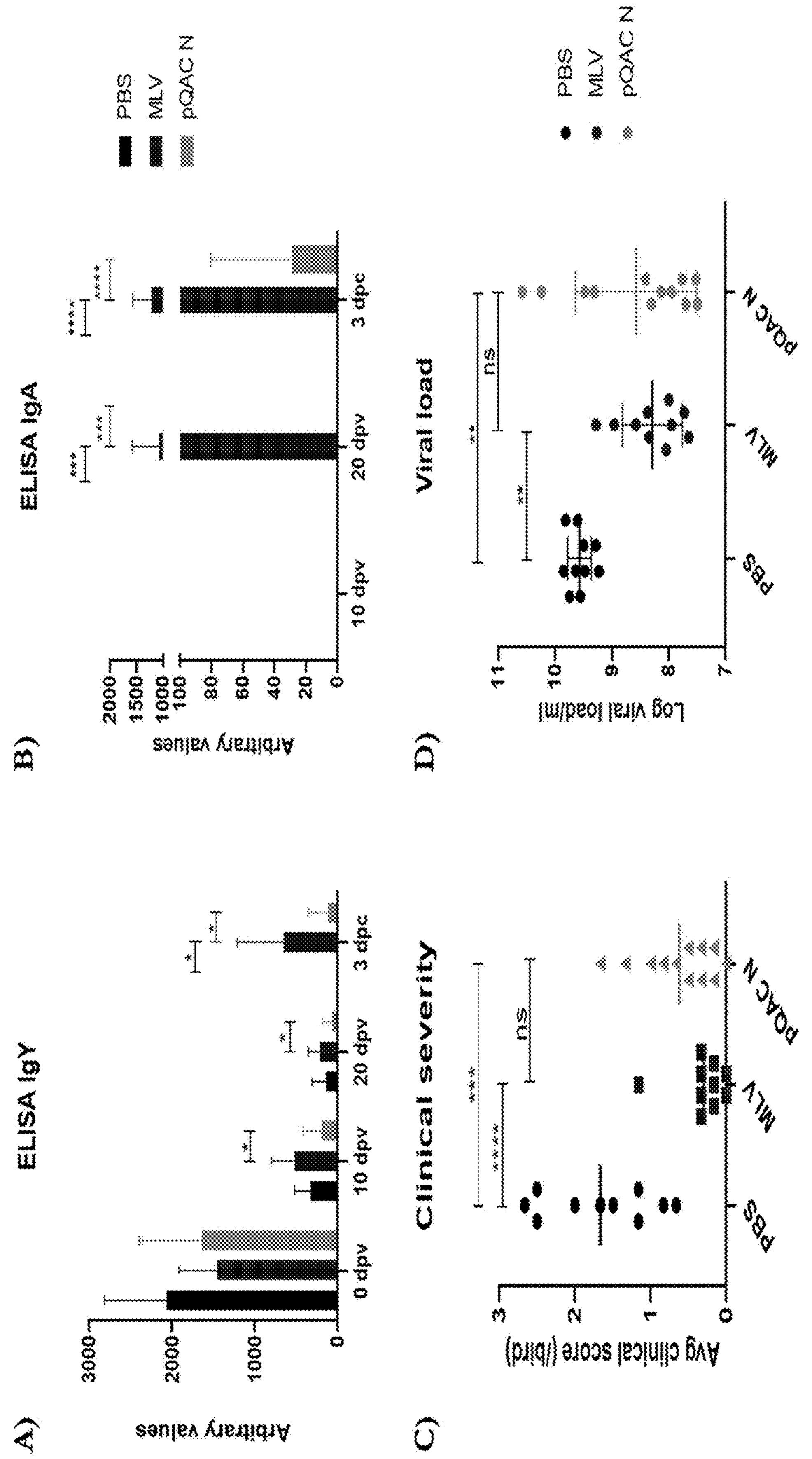
FIGS. 27A-27D show Reduced tracheal viral shedding in pQAC-N vaccinated commercial birds. Groups of commercial white leghorn chicks were either unvaccinated (PBS) or immunized with MLV (day-1) or pQAC N vaccine (100 ug) at day-1 and day-14. IBV specific IgY in serum (A) and IgA in lachrymal fluid (B) significance (*, $P<0.05$; , $P<0.01$; *, $P<0.001$; **, $P<0.0001$) was determined by two-way ANOVA (C) Clinical sign severity represented as average score/bird over 8 days post challenge in each group (D) IBV viral load in tracheal swabs at 6 days post challenge. Significance (*, $P<0.001$; ****, $P<0.0001$) or non-significance (ns) was determined by one-way ANOVA with multiple comparisons. Data show means±SD.
Figure 28:
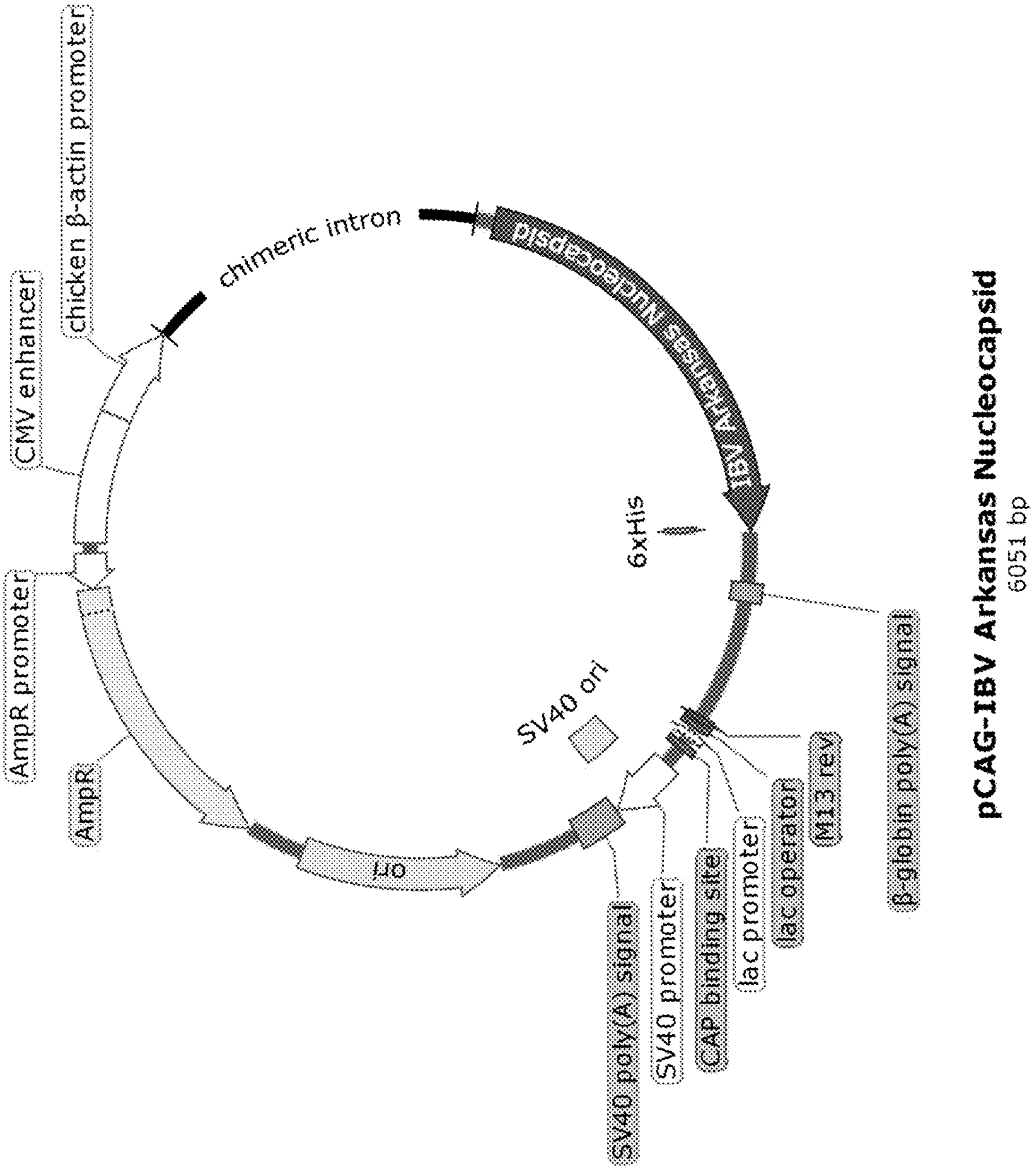
FIG. 28 shows a vector map of the pCAG-IBV Arkansas nucleocapsid plasmid (SEQ ID NO:1).
Figure 29:
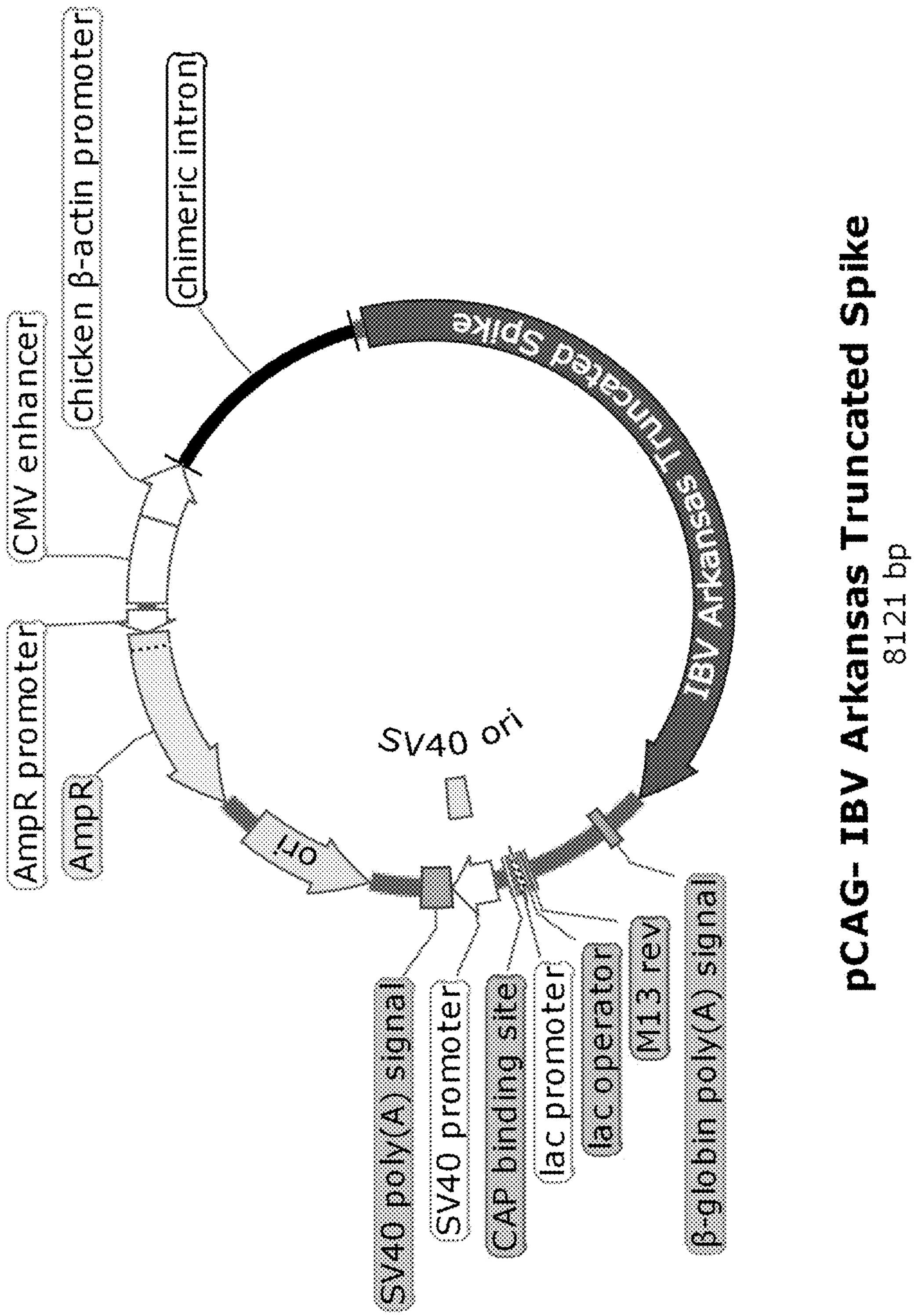
FIG. 29 shows a vector map of the pCAG-IBV Arkansas Truncated Spike plasmid (SEQ ID NO:2).
Figure 30:
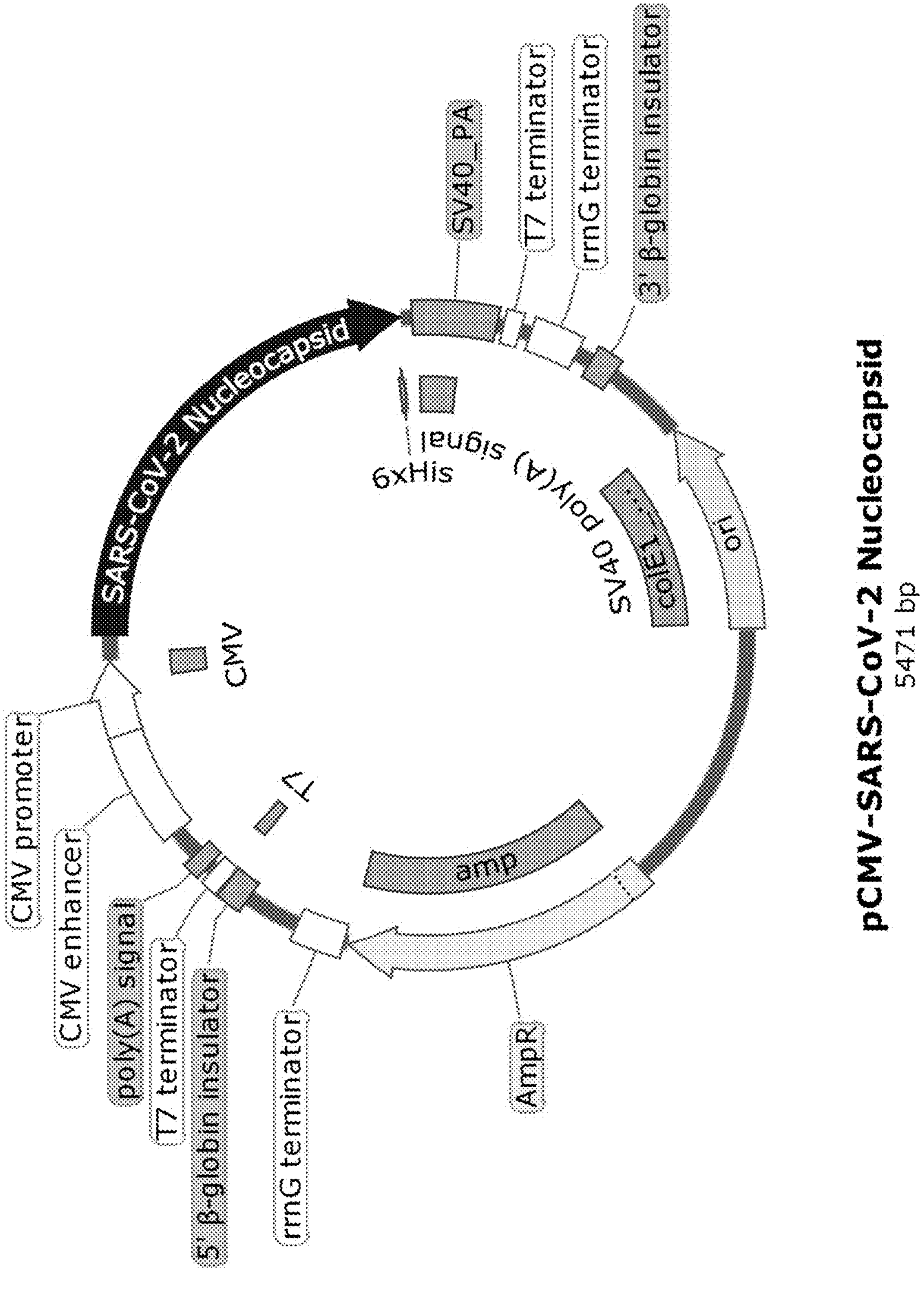
FIG. 30 shows a vector map of the pCMV-SARS-CoV-2 nucleocapsid plasmid (SEQ ID NO:3).
Figure 31:
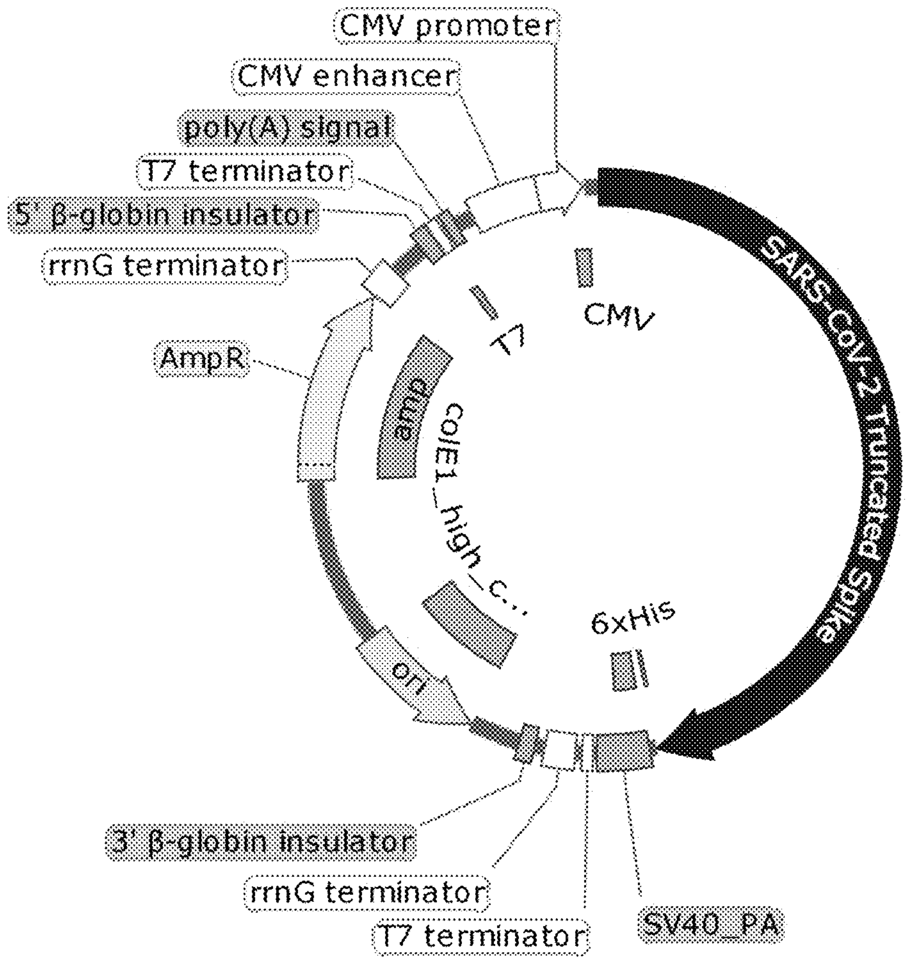
FIG. 31 shows a vector map of the pCMV-SARS-CoV-2 truncated spike plasmid (SEQ ID NO:4).

After the pilot study, the ability of pQAC-N to reduce viral shedding in trachea was evaluated in comparison to MLV vaccinated birds. Similar to the previous trials, pQAC-N vaccinated birds had significantly reduced viral shedding in tracheal swabs and clinical severity post challenge on par with MLV vaccinated birds (FIGS. 27C & 27D). Interestingly, MLV vaccinated birds showed signs of respiratory distress as late as 15 dpv, with one bird dying at 10 dpv which was not observed in the other groups and with SPF birds in the previous trial. Diagnostic analysis including necropsy with bacteriology and virology analysis was performed by the Wisconsin Veterinary Diagnostic Laboratory on the dead bird and on a euthanized control bird. Investigation revealed the presence of *Staphylococcus aureus* and *Escherichia coli* superinfection in the dead MLV vaccinated bird which was not detected in the euthanized control bird. Severe locally extensive pulmonary edema was reported in the lungs of the MLV vaccinated bird which was a result of bacteremia/sepsis, the likely cause of death. MLV vaccinated birds were significantly lighter in weight (FIG. 26A) and had reduced weight gain between 14-28 dpv (FIG. 26B), a potential consequence of bacterial superinfection.

Discussion

Many experimental subunit and plasmid DNA vaccines against IBV have been developed and its efficacy detailed in previous studies. Intra muscularly (I.M) and in ovo administered experimental vaccines without adjuvants or complemented with natural and molecular adjuvants like IL-2 and GM-CSF have been shown to reduce viral shedding, clinical signs and improve protection rates against IBV (18-26). Alternative routes such as in ovo administration of 51 plasmid DNA vaccine has also been shown to elicit a modest immune response (19). Compared to 51 protein, higher protection rates against IBV challenge and increased total T-cells were shown with I.M immunization with plasmid encoding N protein (20, 23, 25). In this study, we detail the development of a safe mucosal vaccine adjuvant (QAC) for intranasal immunization, a highly desired feature of mass vaccinations under field condition. The safety of QAC nanocarrier was examined by two common routes of field immunization, I.N and in ovo. Birds intranasally immunized by a single dose or double doses (at 1 and 14 days of age) did not show any signs of respiratory distress, and weight gain was same as observed with control birds. The in ovo immunization also did not affect embryo development and egg hatch rates. Previously, both Quil-A and chitosan were shown to be biocompatible with no adverse effects reported when administered to animals (30-32, 40). Similarly, our results indicate that the QAC adjuvant is safe, tolerable and biocompatible in chicken hosts.

For vaccine efficacy, our experimental vaccine (pQAC-N) was compared to the current commercial MLV in a challenge model adopted based on recommended guidelines from the food and drug administration with modifications (FDA-9CFR). The superiority of the QAC adjuvant system was shown in a challenge model where birds were challenged immediately at 7 days following vaccine boost with a relatively high dose of IBV Ark-DPI (6.5E9 genome copy no or $10^{6.5}$ $EID_{50}$). Specifically, we demonstrated the ability of QAC adjuvant system to enhance immunogenicity and protective efficacy of pCAG-N plasmid vaccine which otherwise conferred partial protection when administered independently (naked pCAG-N). It is possible that N protein uptake and processing by antigen-presenting cells (APCs) is a key step in the downstream activation of B and T-cells for developing a robust memory immune response (41) that was shown in the pQAC-N immunized birds. Factors that influence APC uptake of antigens includes particle surface charge, size, hydrophobicity and others (42). Soluble viral immunogens by themselves owing to their small size (<20 nm) are poorly taken up by APCs. Particulate adjuvant systems with a size range of 20-200 nm have been shown to promote APC uptake by endocytosis (42). Our findings have shown that QAC-based formulations formed spherical disaggregated particles of optimal size (<100 nm) for efficient APC uptake and processing, as expected when the Quil-A surfactant is added. Delivery systems with net positive surface charge like QAC (positive zeta potential 15±4.4 mV), temporarily disrupt membrane of cells causing membrane flipping and/or fusion at cell surfaces mediating payload delivery or enter cells via clathrin-mediated endocytic pathway, a potential pathway for effective antigen uptake (43). Chitosan DNA particles promote the slow release of packaged DNA and similarly, we observed the sustained release of DNA payload complexed with QAC in vitro (44). Our in vitro analysis indicated that QAC could promote targeted delivery of payload into cells and/or act as antigen depots maintaining a sustained release of payload priming immune cells continually. Overall, encapsulation of plasmid DNA by QAC mediated slow release of immunogen which could help in continuous priming of antigen presenting cells and overcome the need for multiple immunizations.

pQAC-N vaccinated SPF birds had a significantly lower viral burden when compared to unvaccinated birds. Chitosan by itself did not reduce viral shedding observed with naked unadjuvanted pCAG-N construct, suggesting a key role of the nanocarrier size and composition used in our hands. Interestingly, a strong correlation between reduced clinical severity and reduction in viral load was observed. The protective efficacy of pQAC-N was comparable to MLV with similar levels of reduced clinical severity and non-significant reduction in viral load observed between both groups. To our knowledge, with the exception of one study, most experimental IBV DNA vaccines have been tested against serotypes not endemic to US, via I.M route and without a comparable commercial live virus group (20-26). Here we observed that the pQAC-N vaccine when administered I.N was able to protect vaccinated birds against a field-relevant IBV Arkansas-DPI, most likely because of the induced localized immunity as suggested before (34, 45). PBMCs harvested from pQAC-N vaccinated birds responded to antigen stimulation ex vivo with significantly higher proliferation than seen with control and other plasmid DNA vaccine groups. Moreover, the analysis of different immunological parameters indicated that pQAC-N induces strong CMI responses in contrast to MLV, which induced potent antibody responses. The induction of CMI responses could be a hallmark for the pQAC-N nanovaccine. IBV N protein is a highly immunogenic antigen with mapped CTL epitopes in the C-terminal which mediate potent CTL memory responses. IBV specific memory CD8+ T-cell responses restrict IBV replication efficiently and are strong correlates of protection for IBV control (34). It is noteworthy here that birds vaccinated with an experimental IBV N-based vaccines generally have a higher percentage and proliferation of CD3+ CD8+ T-cells, albeit not specific to IBV, a limitation of assaying total T-cell numbers (20, 23, 25).

To decipher QAC-DNA mediated IBV specific immunity, we used flow cytometry assisted lymphocyte proliferation assay to identify and quantify subsets of T-cells responding to IBV antigen. Similar to results with MTT assay, we noticed lung cells from pQAC-N vaccinated birds had higher stimulation ex vivo when compared to the control groups. More reactive CD8+ and TCRγδ+ T-cells were present in pQAC-N vaccinated birds, albeit non-significant. Large variations in recall proliferation within pQAC-N vaccinated group was observed, a phenomenon that has been reported in other published studies investigating chicken immune responses (46). Presented results suggest that vaccination with pQAC-N confers protection against IBV challenge to levels similar to MLV vaccination and that protection might be attributed to an induction of CD8+ and TCRγδ+ memory T cell responses, rather than CD4+ induction observed with MLV vaccination. Further studies to elucidate the exact mechanism of pQAC-N mediated immunity are needed.

Most commercial breeders are immunized with IBV vaccines and transfer IBV specific IgY to their progeny via egg yolk which can interfere with vaccine efficacy. Prior evidence suggests that DNA vaccination could overcome limitations of early vaccinations by priming the immune system even in the presence of interfering MDA (47-49). Our results indicate that pQAC-N can mediate protection in the presence of MDA reducing viral shedding in lachrymal fluid and in the trachea. As observed in the trial with SPF chicks, IBV specific IgA and IgY were detectable in pQAC N vaccinated birds albeit significantly lower than levels in MLV vaccinated birds. Mortality associated with IBV outbreaks in the field is usually low unless compounded by secondary bacterial infections (50). Interestingly, in the latest trial conducted, MLV vaccinated commercial birds had active bacterial superinfection leading to mortality in one bird (~8%), reduced weight gain and presence of respiratory clinical signs which was not seen in pQAC-N vaccinated birds. This observation underscores the inferior safety profile of commercial MLV vaccines.

Although protective, addition of other inexpensive biocompatible adjuvants to generate a complementing humoral response could be used to the current pQAC-N construct. In summary, we detailed the development of a safe plasmid DNA vaccine complimented by a mucosal adjuvant system (QAC) which protects SPF and commercial birds against IBV challenge by eliciting a strong T-cell immune response. We postulate that the QAC nano-adjuvant system can be used as a vaccine adjuvant for the delivery of plasmid DNA and protein immunogens against other respiratory viruses and intracellular pathogens for poultry and other animals.

Materials and Methods

Cells and Viruses—Expi293F cells obtained from ThermoFisher Scientific was used for confirming expression of IBV Ark N6×His protein from vaccine construct. The cells were cultured in Expi293 medium at 37° C., 125 rpm, 8% CO2 atmosphere in plastic flasks with ventilated caps. The virulent IBV Arkansas DPI strain (a kind gift from Dr Ladman and Dr Gelb) was propagated in 9-day old SPF ECEs and allantoic fluid harvested four days after infection. The stock virus titre was determined using RT-qPCR (see below) and also titrated and expressed as 50% embryo infectious dose ($EID_{50}$) (51). IBV S1 gene sequence of Ark DPI challenge isolate is AF006624.

Figure 3:
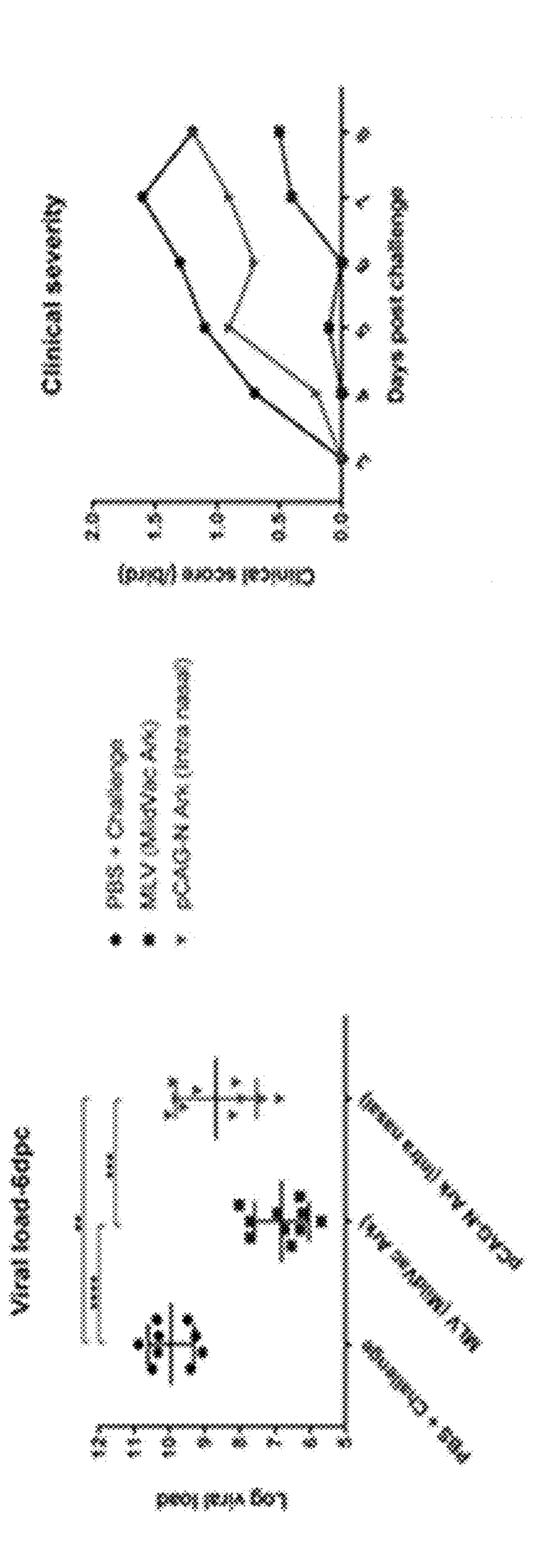
FIG. 3 shows intra nasal immunization with naked DNA constructs. Partial protection was observed with naked DNA vaccines for intra nasal administration. Partial reduction in viral burden and clinical signs of severity were observed with the naked IBV N vaccine construct, IBV specific mucosal IgA was detected in naked DNA vaccinated birds, and no appreciable circulating IgY responses were detected in birds vaccinated intra nasally.
Figure 3:
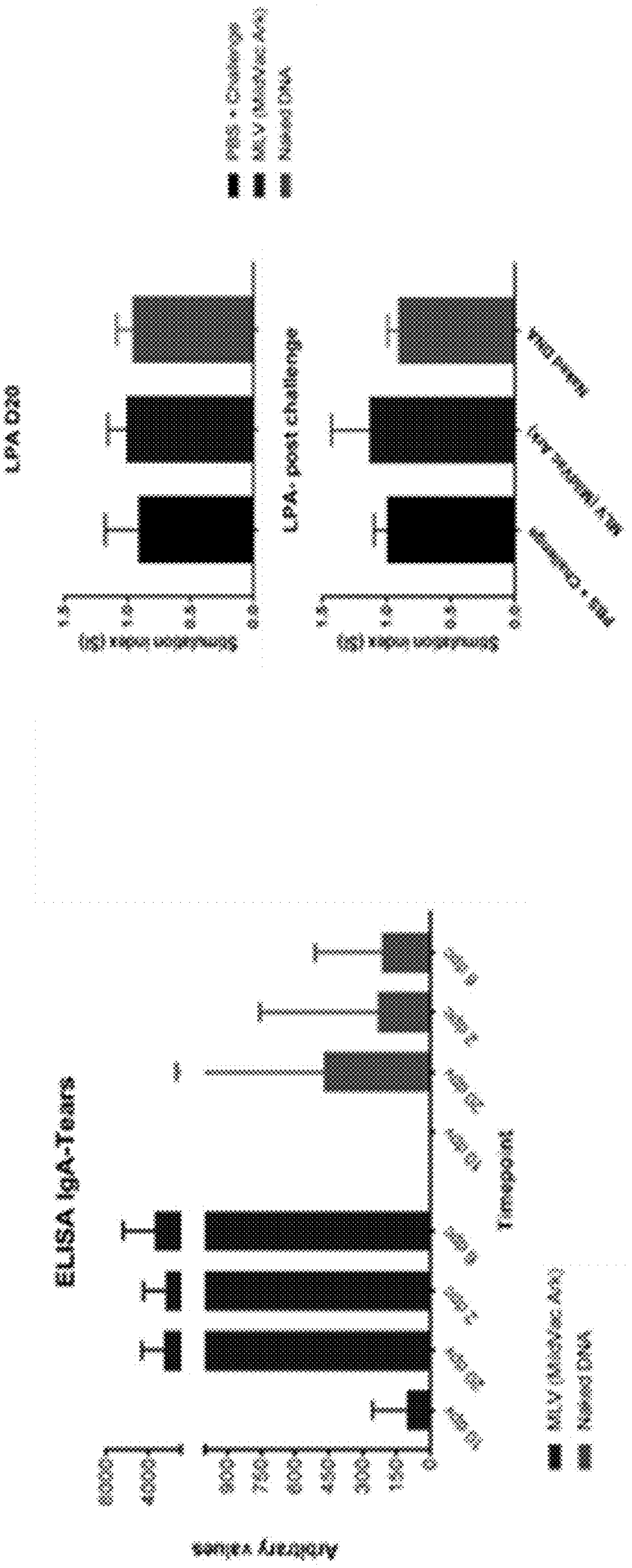
Figure 4:
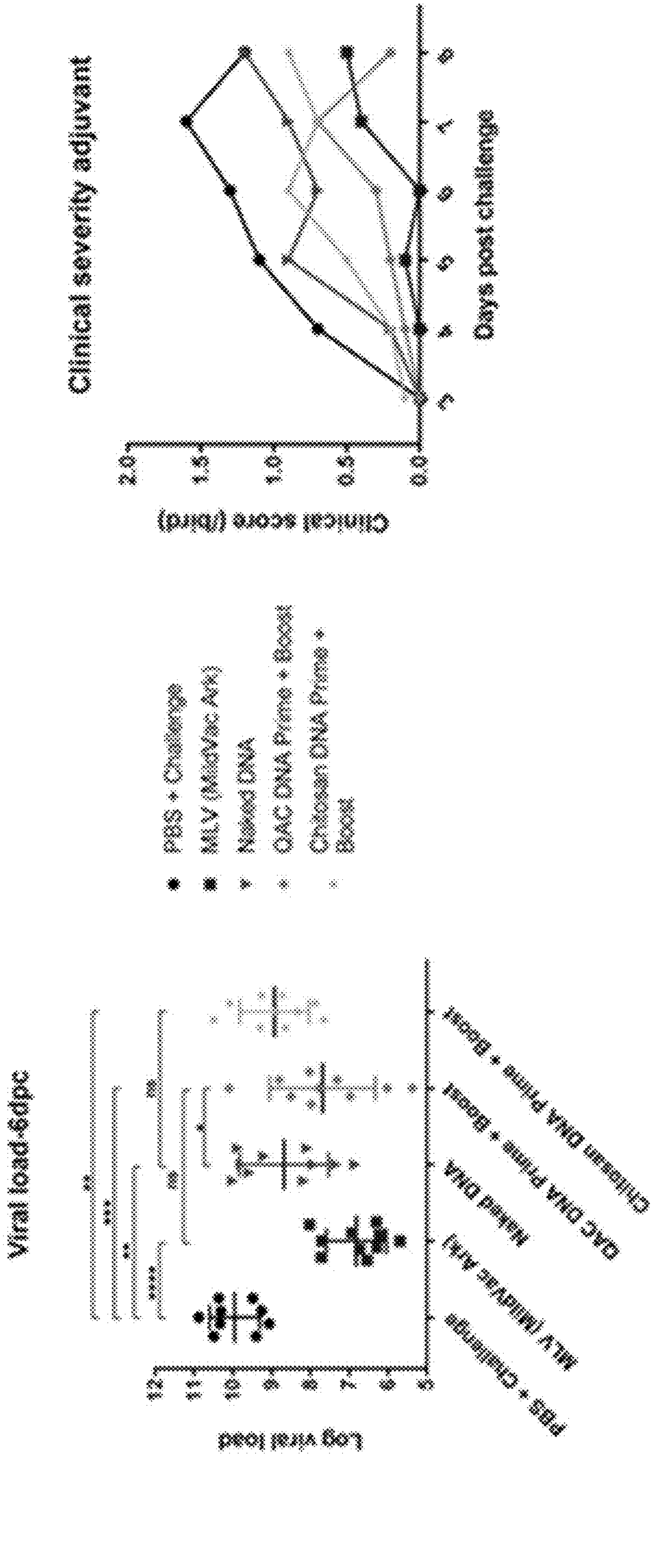
FIG. 4 shows immunization with adjuvanted DNA constructs. Partial reduction in viral burden and clinical signs of severity observed were with chitosan adjuvanted DNA constructs compared with the naked DNA construct. Chitosan alone does not boost protection. More robust induction of mucosal IBV-specific IgA were observed with QAC adjuvanted DNA constructs. Higher reduction in viral burden and clinical severity were observed with QAC adjuvanted DNA construct with levels comparable to commercial vaccines. Significant proliferation of T-lymphocytes in response to antigen observed with birds vaccinated with QAC adjuvanted DNA construct. DNA constructs are more immunogenic and protective when adjuvanted with QAC. This demonstrated that the QAC complex adjuvant boosts protection and immunogenicity compared to that observed with naked DNA vaccines alone without adjuvant.
Figure 4:
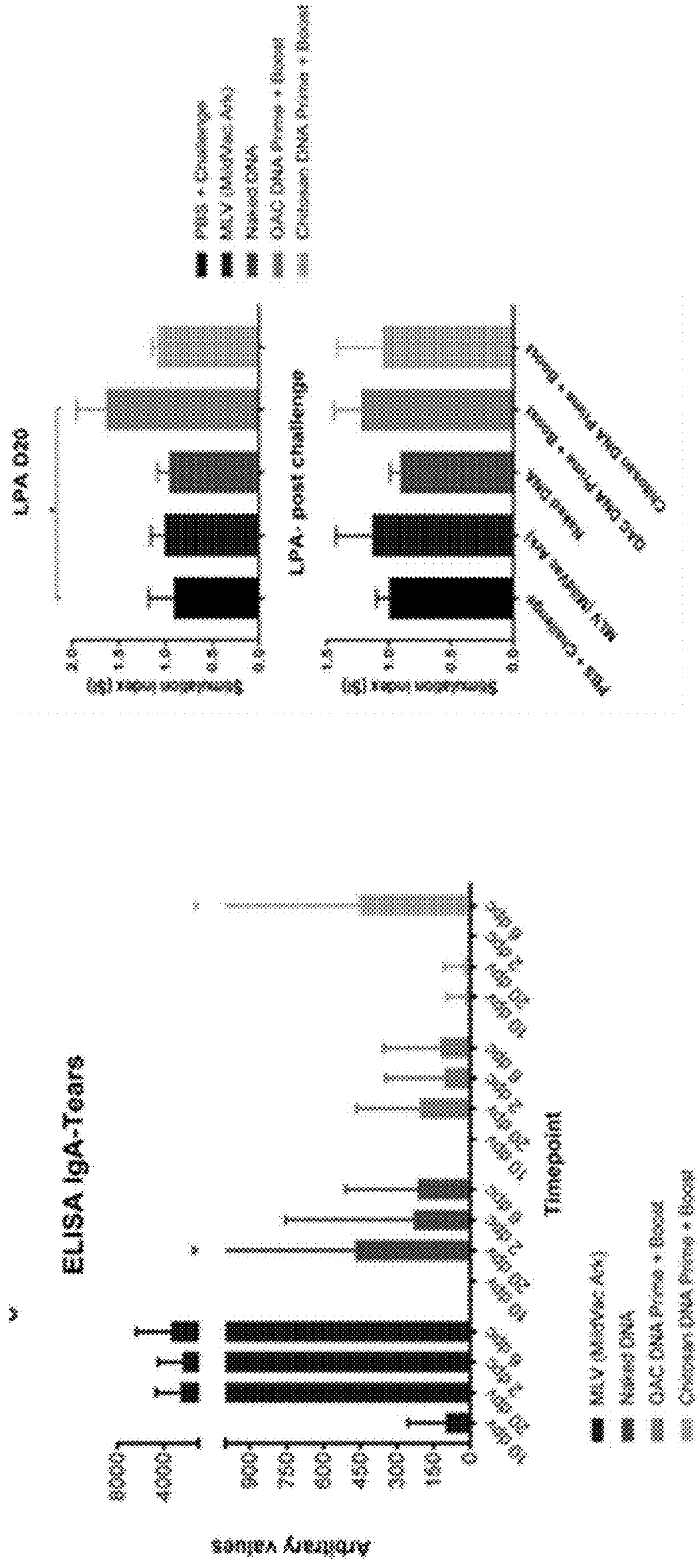
Figure 5:
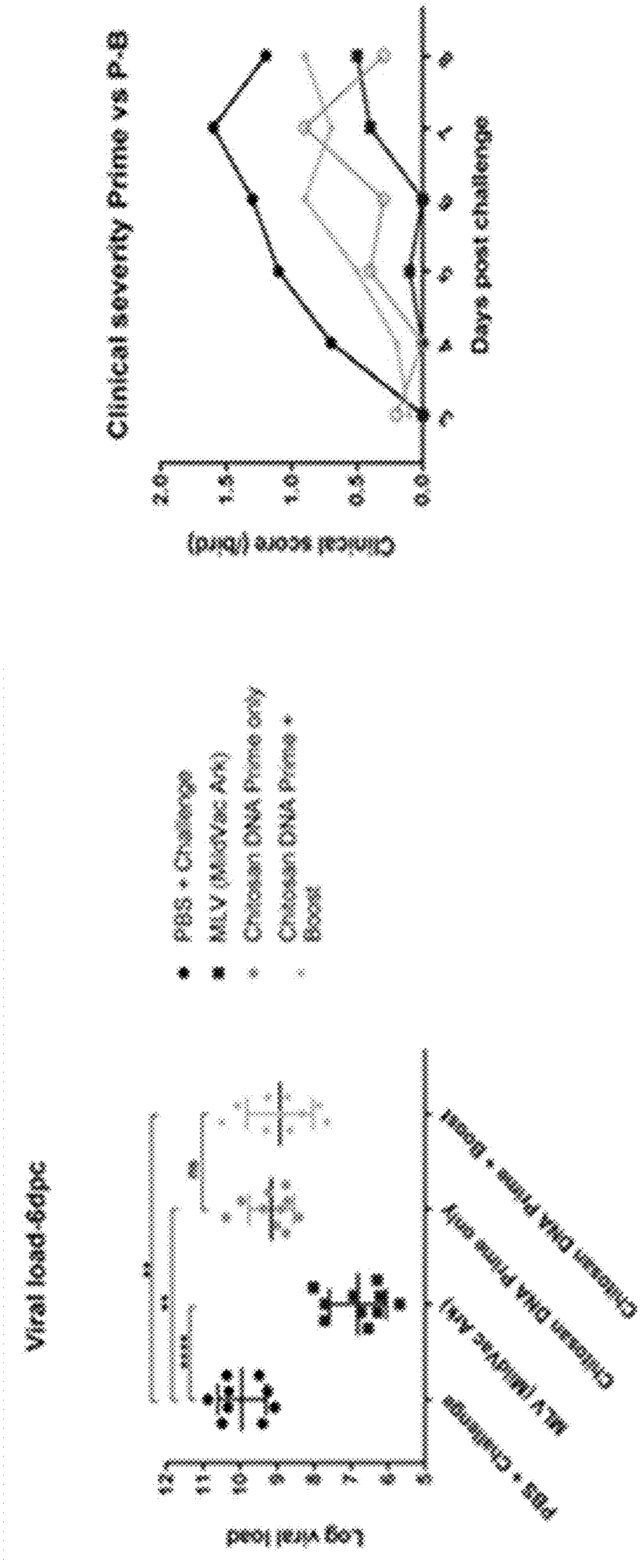
FIG. 5 shows a comparison of the prime (single dose of adjuvanted vaccine as day 1) and prime-boost (two doses of the adjuvanted vaccine 2 weeks apart at day 1 and day 14) strategies. No difference in reduction of viral burden and clinical severity, antibody and cell-mediated responses were observed between birds immunized with prime or prime-boost strategy.
Figure 5:
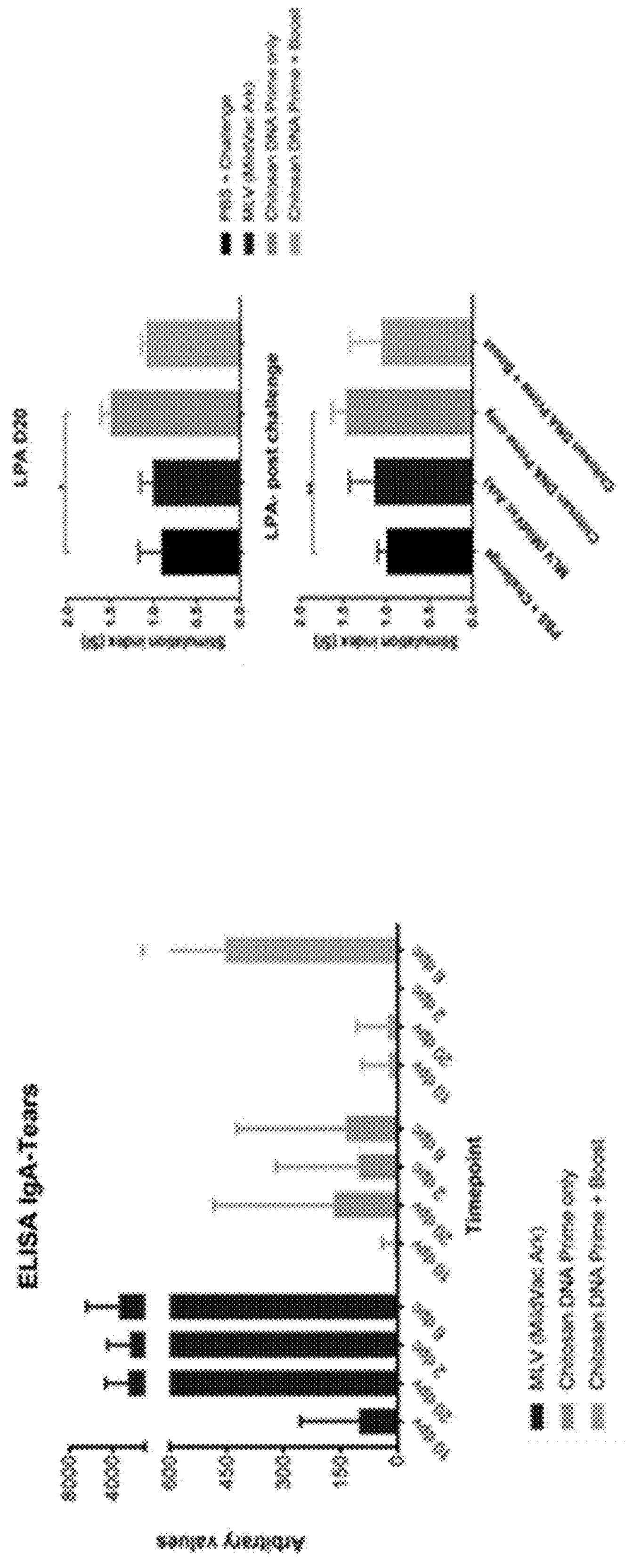
Figure 6:
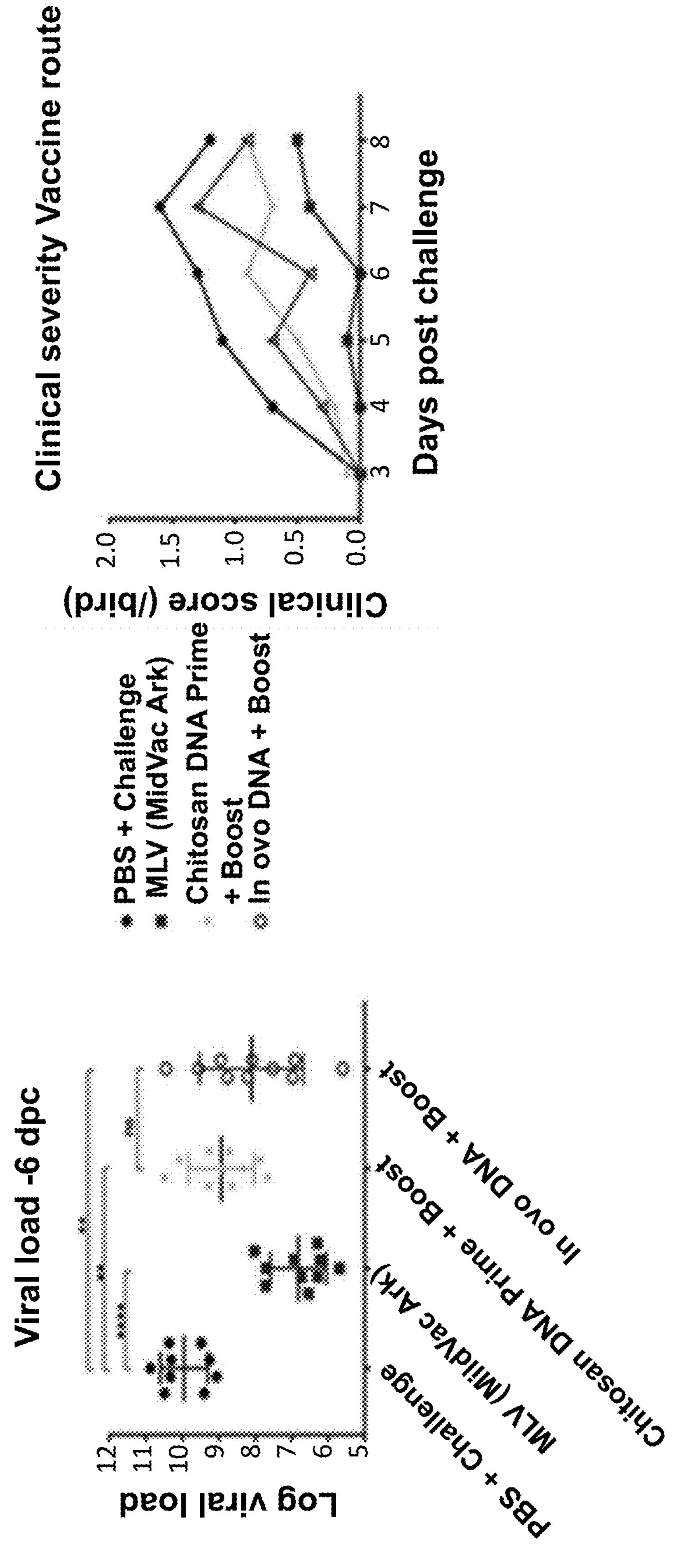
FIG. 6 shows data comparing intra nasal and in ovo vaccination administration routes. Higher reduction in viral load was observed with birds vaccinated via the in ovo route, but the difference was not statistically significant. Higher antibody levels and cellular response was observed post vaccination and post challenge with in ovo group when compared to the intra nasal group. In ovo vaccination route might be a better route for vaccination because similar level of protection was observed (vs intra nasal) but this route is more easily scalable for large scale applications and can overcome interference by maternal derived antibodies (MDA) in commercial birds.
Figure 6:
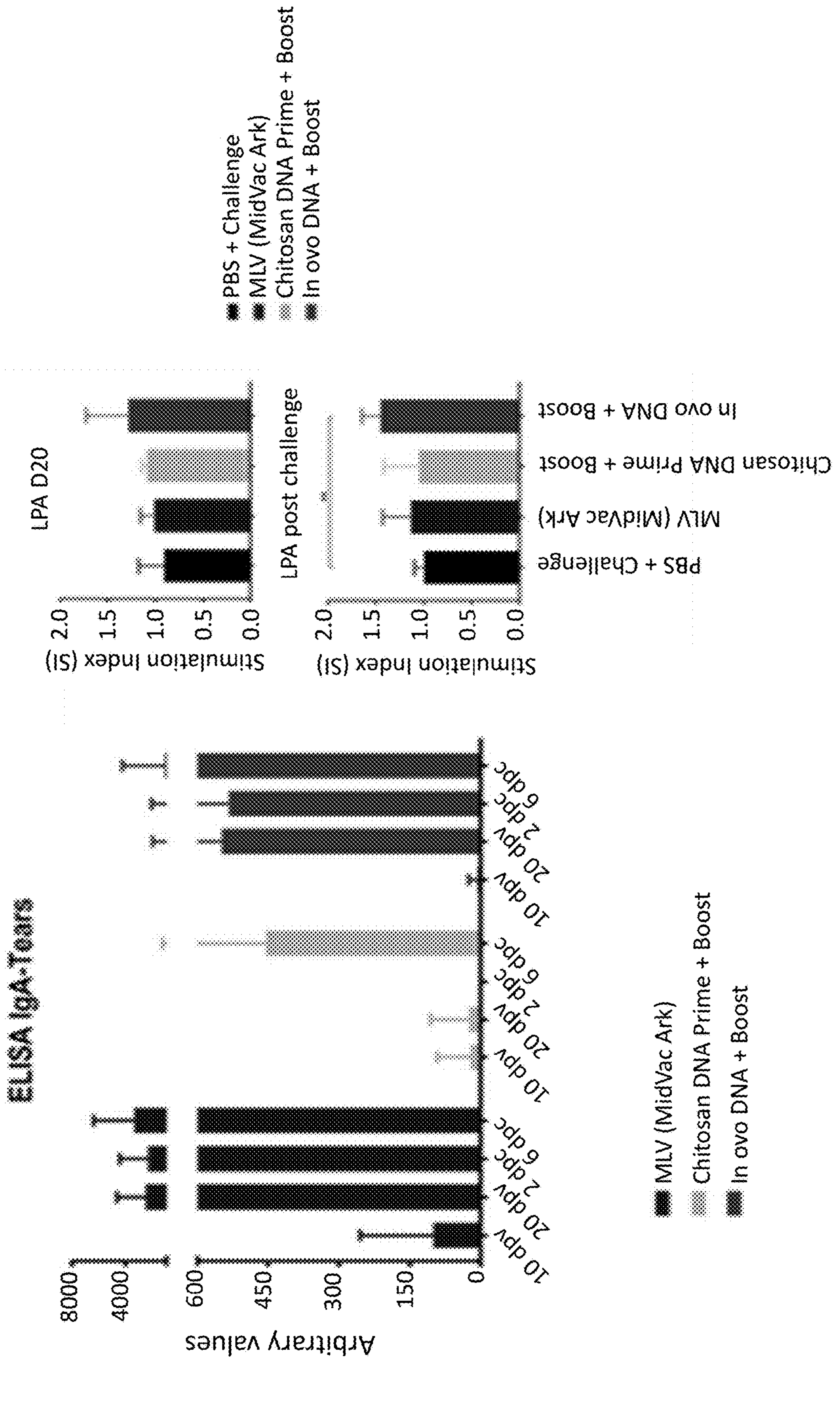
Figure 7:
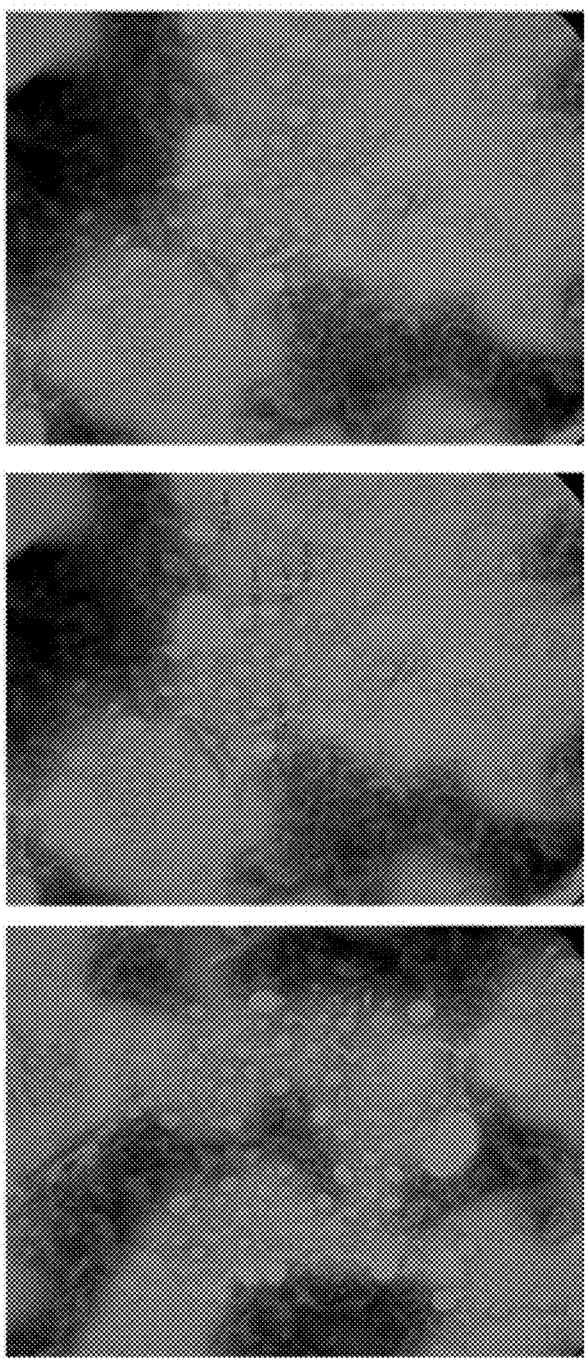
FIG. 7 shows TEM images of chitosan-DNA complexes and DLS size measurement of chitosan-DNA complexes.
Figure 7:
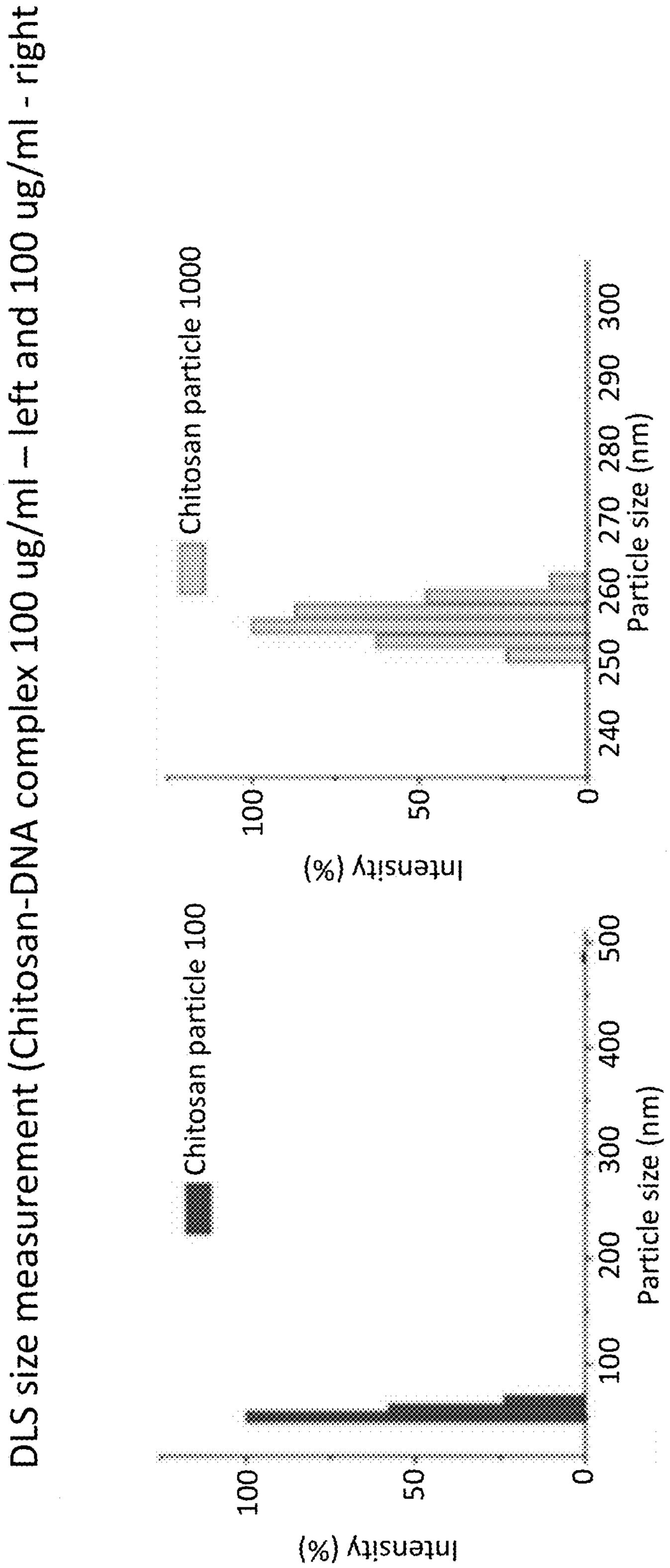
Figure 8:
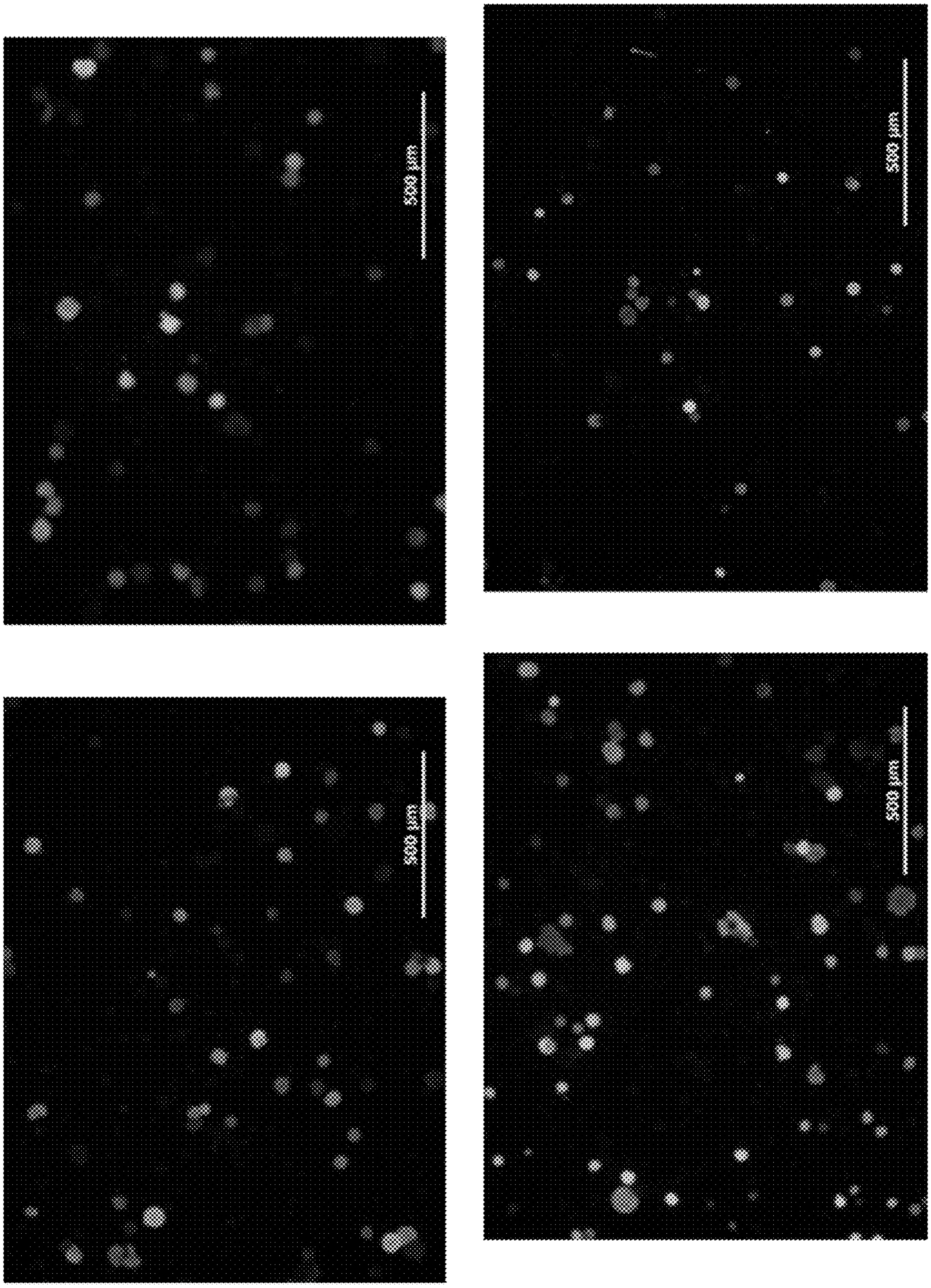
FIG. 8 shows cells transfected with chitosan-pCAG-GFP complex.
Figure 9:
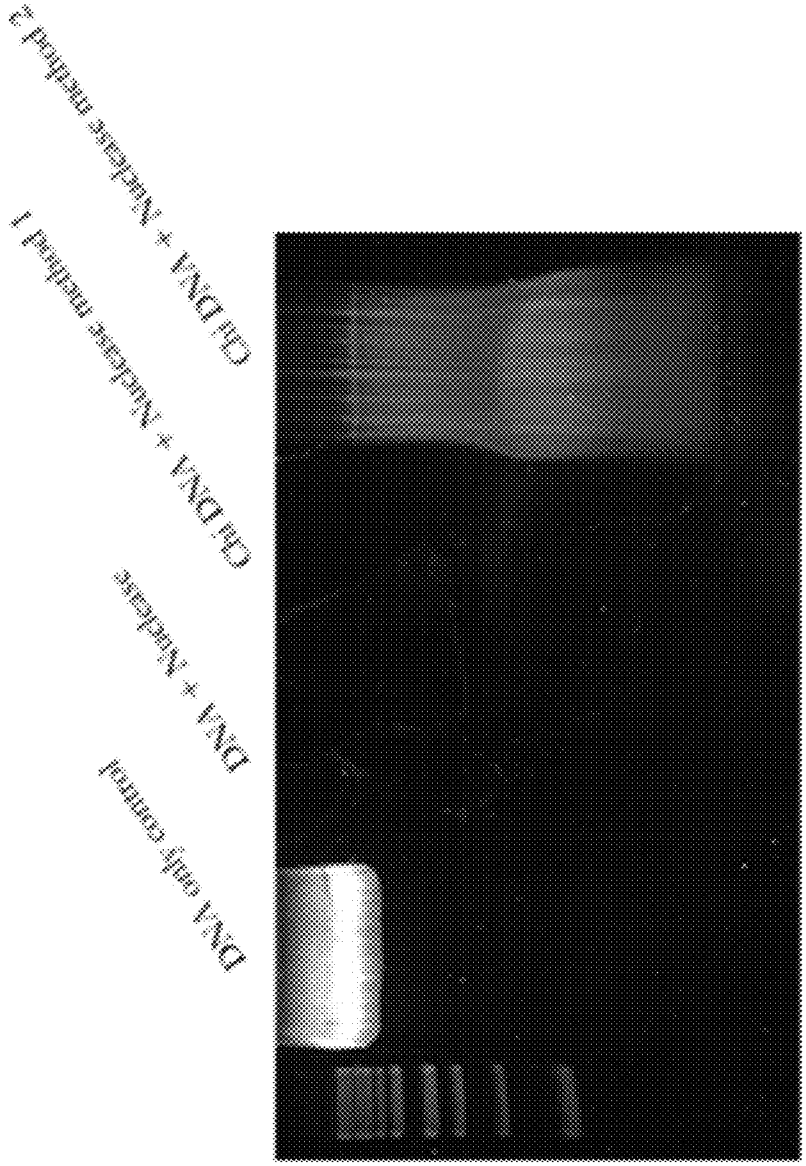
FIG. 9 shows the results of a nuclease protection assay. DNA encapsulated in a chitosan-DNA complex was partially protected when treated with 5×DNase I.
Figure 10:
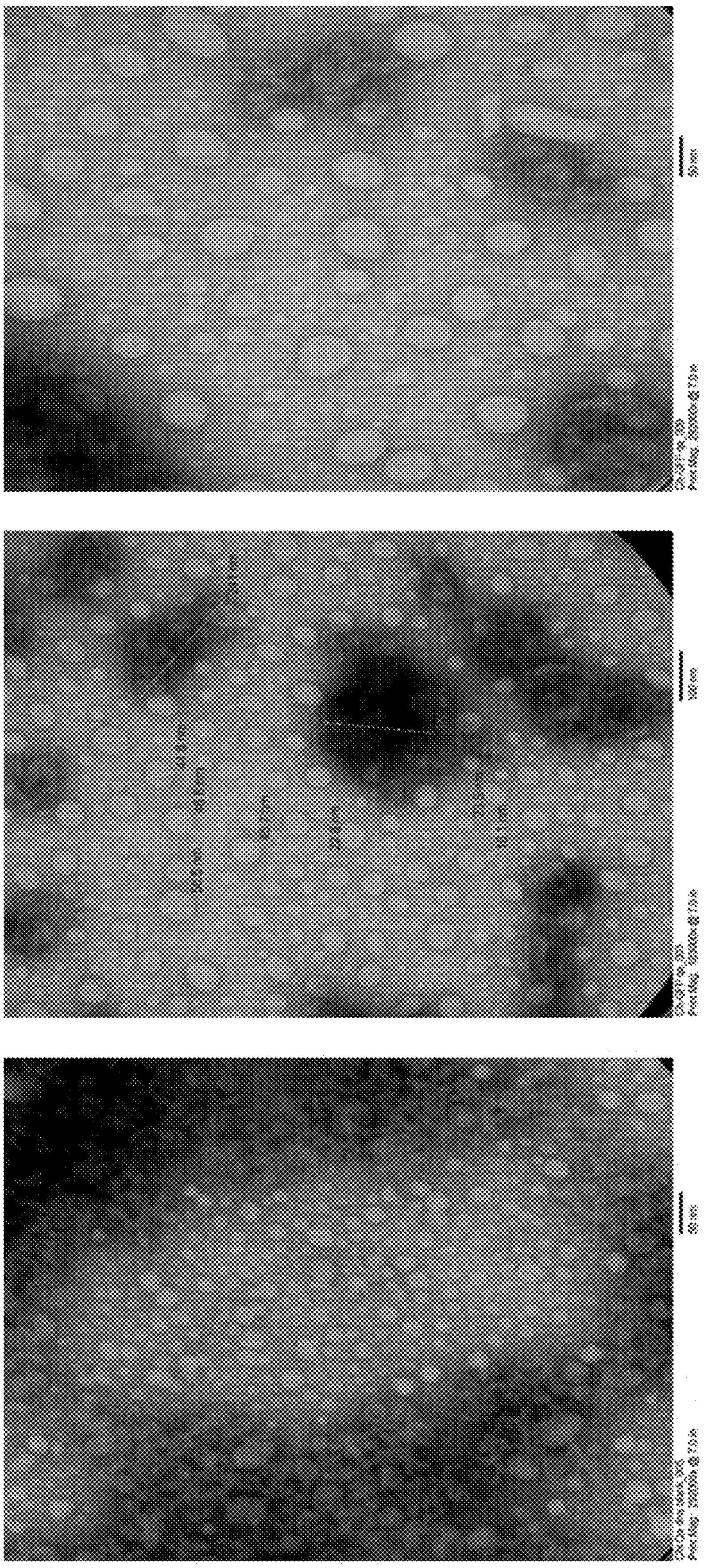
FIG. 10 shows TEM images of empty QAC particles (left) and QAC particles with encapsulated DNA (middle and right, 30-60 nm).
Figure 11:
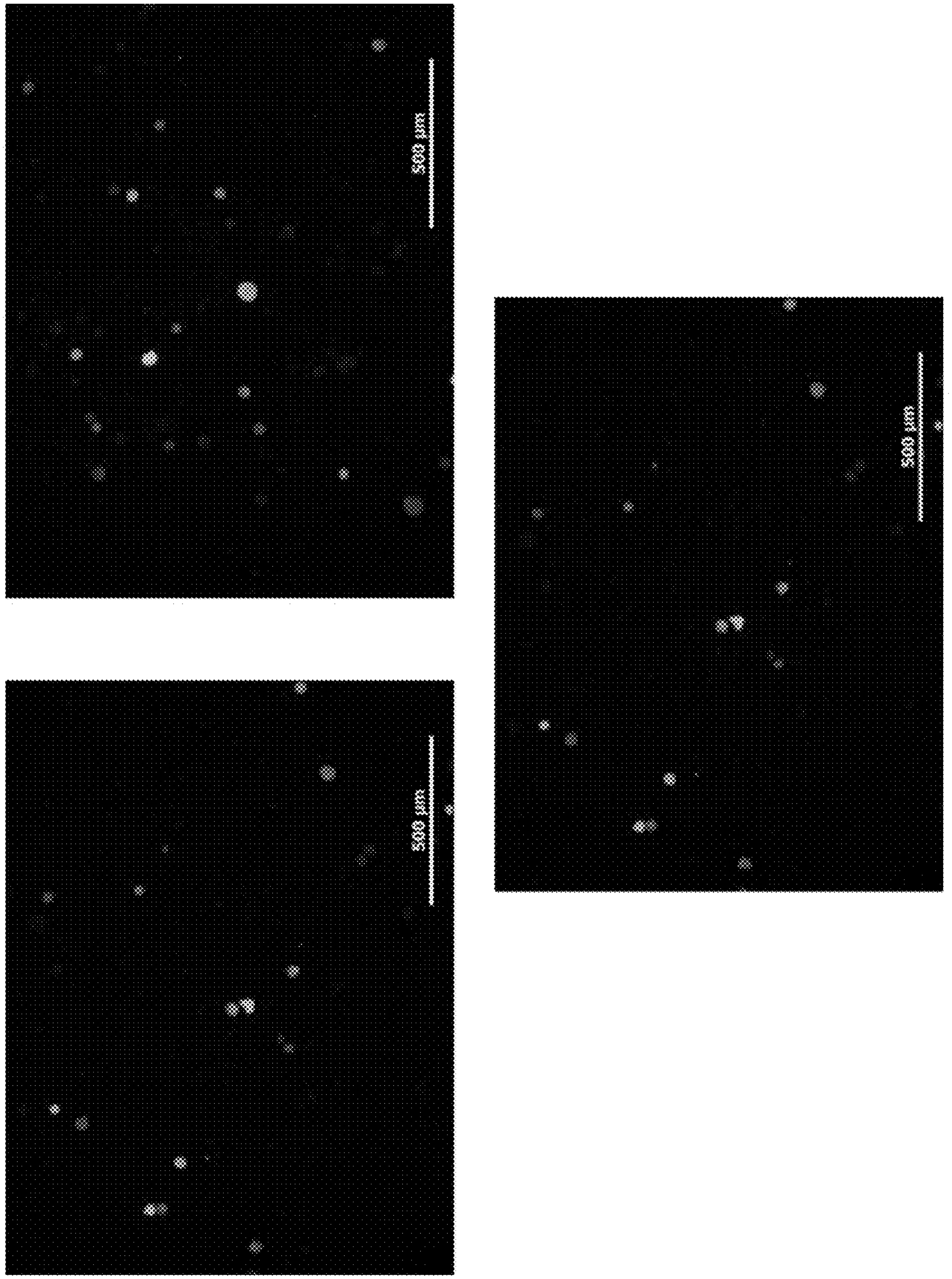
FIG. 11 shows cells transfected with QAC-pCAG-GFP complex (100 ug/ml).

Preparation of plasmids—Arkansas Nucleocapsid (N6× His) and S1 gene (S1 6×His) was amplified from reverse transcribed cDNA synthesized from IBV Arkansas 99 (ATCC VR-841) with a C-terminus 6×His tag. The forward primer ((5'-ATCACTGAATTCACCATGGCAAGCGG-TAAAGCAG-3') SEQ ID NO: 13) and reverse primer ((5'-ATCACTGCGGCCGCTTAGTGGTGATGGTGATG-ATGACCTCCTCCAAGTTCATTCTCTCCTAGAGCTG-C-3') SEQ ID NO: 14) were employed for amplifying N6×His. The forward primer ((5'-ATCACTGAATTCAC-CATGTTGGTGAAGTCACTGTTTCTAGTG-3') SEQ ID NO: 15) and reverse primer ((5'-ATCACTGCGGCC-GCTCAGTGGTGATGGTGATGATGCCCTCCGCCGG-AGGATCCAGTT CCATTAGTGATCTTAATGTAAAA-CTGGTTTTC') SEQ ID NO: 16) were employed for amplifying S1 6×His. Amplified gene fragments were cloned into EcoRI and NotI restriction sites of pCAG-GFP plasmid, a gift from Connie Cepko (addgene plasmid #11150, FIG. 3A). To confirm insertion of genes in the correct orientation, DNA sequencing was performed at the UW-Madison Biotechnology Center with an ABI Prism 3730XL DNA analyzer using BigDye terminators (Applied Biosystems, CA). To confirm expression of N6×His and S1 6×His protein, Expi293F cells seeded in 6-well format was transfected with an optimized ratio of DNA (4 ug): TransIT PRO transfection reagent (2 ul) according to manufacturer's instructions (Mirus Bio, WI, USA). Three days post transfection, cells were harvested for western blot analysis. Cell fractions were boiled in Laemmli sample buffer (BioRad, Hercules, Calif., USA) and resolved on a 4-20% SDS-PAGE gel by electrophoresis using a Mini-PROTEAN 3 system (BIO-RAD, CA). Polyacrylamide gels were electroblotted onto nitrocellulose membranes using a Turboblot® system. Membranes were blocked in 5% (W/V) skim milk and probed with polyclonal anti-6×His HRP antibody (ThermoFisher Scientific, MAI-21315-HRP). Membranes were developed using a solid phase 3,30,5,50-tetramethylbenzidine (TMB) substrate system.

Characterization of nanoparticles—Quil-A (VET-SAP, Desert King) stock solution of 0.2% was made in nuclease free water. Chitosan stock solution (>75% deacetylated, Sigma) of 0.4% in 1% glacial acetic acid was prepared and diluted to 0.04% in 5 mM sodium acetate buffer, pH 5.5. Both components was heated separately for 30 mins in a 55 C water bath. Equal volume of Quil-A-plasmid DNA solution was added drop by drop to the chitosan solution and the mixture was vortexed for 30 s. The solution was left at room temperature for 1 hour to promote QAC-DNA particle formation. Plasmid DNA was diluted to 100 ug/ml in 50 mM sodium sulphate buffer and Quil-A was added to a final concentration of 0.002%. Size distribution and zeta potential of QAC-NPs in aqueous dispersion was measured by dynamic light scattering (DLS) on a Malvern zetasizer instrument at 25° C. For size distribution, 50 ul of QAC-NPs in solution was placed in a low volume cuvette and analyzed directly. For zeta potential measurement, approximately 1 mL of the QAC-NPs in solution was placed in a disposable capillary zeta potential cell available from the Zetasizer Nano series. TEM experiments were performed at the Medical school Electron Microscopy facility of the University of Wisconsin-Madison using a Philips CM120 transmission electron microscope (FEI, Eindhoven, the Netherlands) at 80 kV. The size and morphology of vaccine preparations was reexamined via negative staining using the drop method. QAC NPs loaded with 1 mg total DNA was resuspended in 600 μL of 0.05 M phosphate buffered saline (PBS, pH 7.4) at 37° C. At each time point, suspensions were removed and centrifuged at 14,000 rcf for 20 min. The supernatant was removed and replaced with PBS and returned to incubation. Supernatant samples were quantified for released DNA from the QAC using a NanoDrop™ Spectrophotometer and compared to the total DNA used. QAC-GFP DNA (5 ug) was added to $3\times10^7$ Expi293F cells seeded into a 6 well plate. 72 hours post addition the presence of GFP+ cells was identified using an upright fluorescence microscope. Background fluorescence was normalized using GFP-Expi293F control cells.

Figure 13:
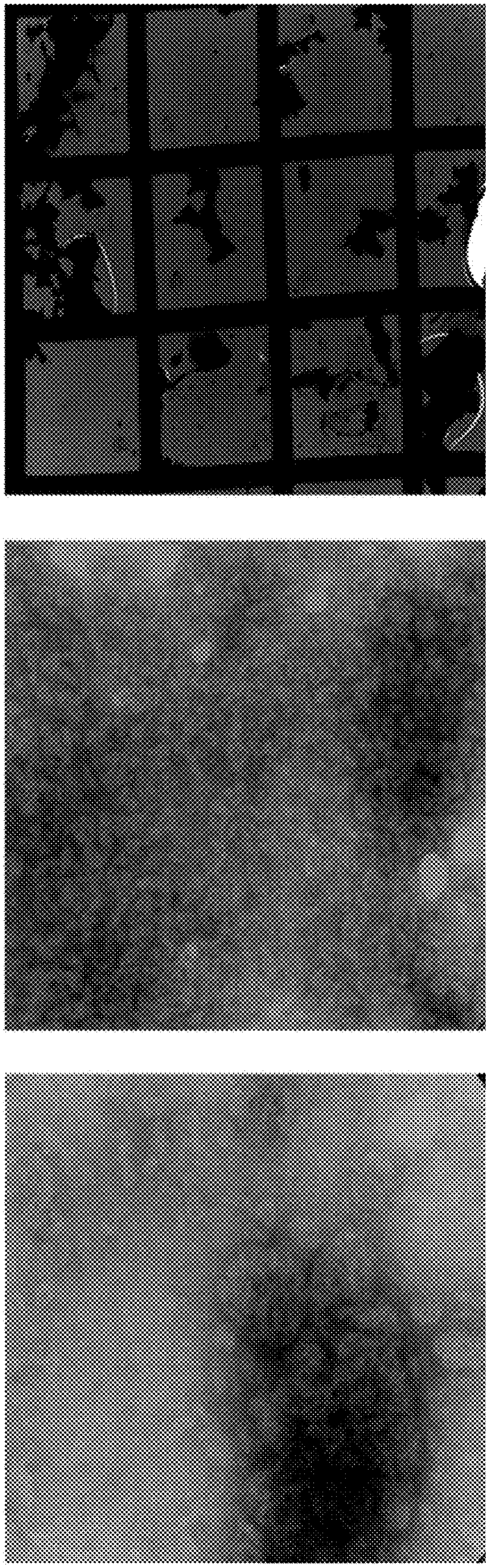
FIG. 13 shows images of other structures formed by varying the ratio of Quil-A:chitosan in QAC complexes.
Figure 13:
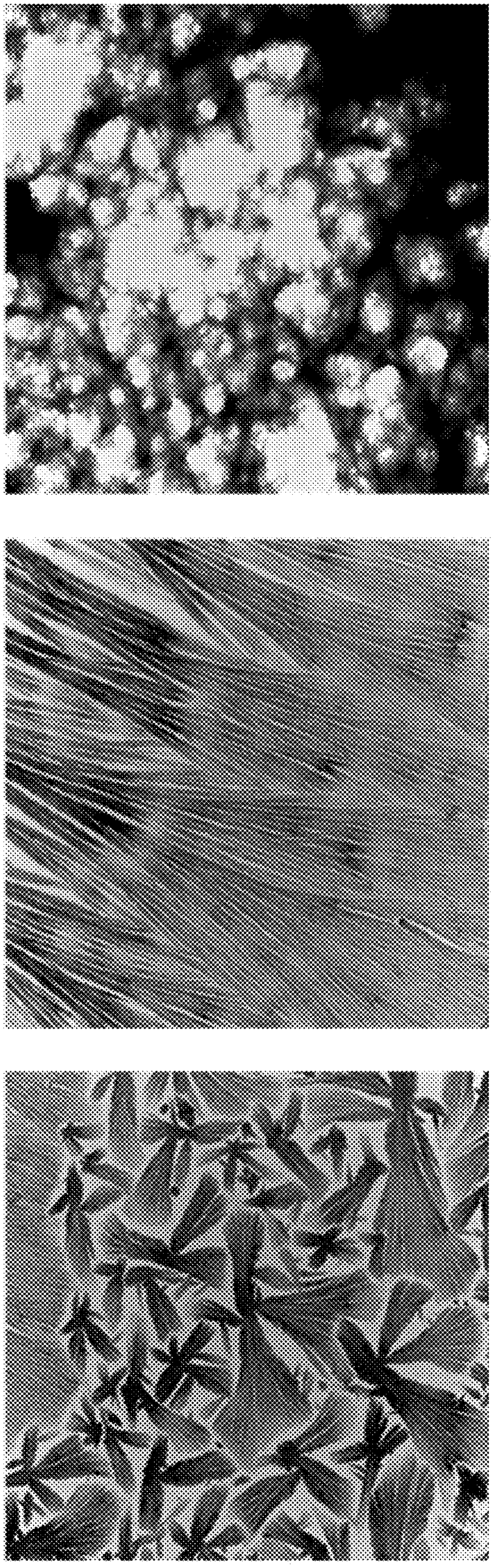
Figure 14:
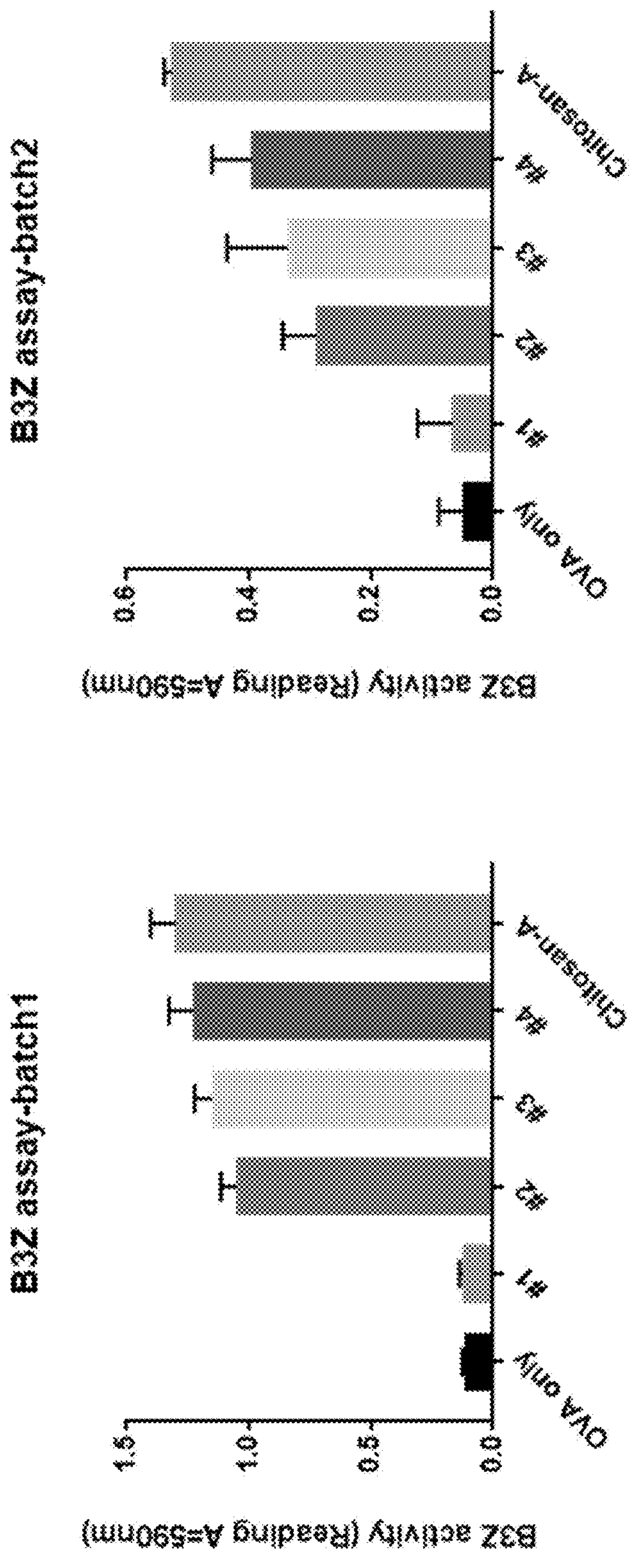
FIG. 14 shows the results of an in vitro antigen cross presentation assay (B3Z assay) using the QAC complex. QAC complex in vitro antigen cross presentation assay (B3Z assay)-Antigen cross presentation is important for effective immune responses to viral infections. Dendritic cells are professional antigen presenting cells and are unique in their ability to cross-present exogenous antigens on MHC class I molecules and activate antigen specific cytotoxic T cells. We tested the ability of Quil-A:Chitosan (QAC) particles encapsulating ovalbumin (OVA) protein to efficiently cross present by dendritic cells (DCs) in an in vitro system using soluble OVA. Ag cross-presentation of OVA257-264 was detected using the CD8 T cell hybridoma cell line B3Z that expresses β-galactosidase under control of the IL-2 promoter. Our preliminary results indicate that QAC can efficiently mediate cross presentation as seen across multiple Quil-A:Chitosan ratios. However, Quil-A is toxic to cells in vitro which could potentially explain a drop in absorbance values with increasing Quil-A concentrations. Adjuvants in vivo have been shown to work by inducing basal local cell damage releasing damage-associated pattern molecules (DAMPs). These DAMPs can further recruit immune cells enhancing antigen and presentation leading to a robust immune response.

Nanoparticle characterization—The QAC complex forms distinct nanoparticles. Various ratios of Quil-A and chitosan were tested as recited in Table 1 and Table 2 below. Also see FIGS. 12 and 13.

TABLE 1

| Quil-A conc (%) | Chitosan conc (%) | Comments |
|---|---|---|
| 0.00004 | 0.02 | Aggregated structure |
| 0.0002 | | Aggregated structure |
| 0.001 | | Distinct nanostructure |
| 0.005 | | Aggregated structure - thick sheets |
| 0.025 | | Aggregated structure - thick sheets |

TABLE 2

| Quil-A conc (%) | Chitosan conc (%) | Comments |
|---|---|---|
| 0.001 | 0.0008 | Distinct filamentous structures |
| | 0.004 | Aggregated structure |
| | 0.02 | Distinct nanostrucutres |
| | 0.1 | Distinct nanostructures (size - 20 nm ± 2 nm) |
| | 0.5 | Aggregated structure - thick sheets |

QAC-protein protocol—Quil-A stock solution of 0.2% was made in nuclease free water. Chitosan stock solution of 0.4% in 1% glacial acetic acid was prepared and diluted to 0.04% in 5 mM sodium acetate buffer, pH 5.5. Protein was diluted to 100 μg/ml in 50 mM sodium sulfate buffer and Quil-A was added to a final concentration of 0.002%. Equal volume of Quil-A-protein solution was added drop by drop to the chitosan solution and the mixture was vortexed for 30 s. The solution was vigorously mixed in shaking conditions (110 rpm) for 1 hour at 37 C to promote QAC-protein particle formation.

Vaccine safety study—In this study, the tolerability and biocompatibility of pQAC-N was evaluated in 1-day-old white leghorn SPF chicks and. ECEs. A total of 30 chicks was divided into 3 groups of 10 each, Chicks from the first group was inoculated with PBS (negative control). Chicks from the other groups were inoculated with either a single dose (100 ug) or 2× the dose (200 ug) of pQAC-N at day-1 via the intranasal route. Chicks were monitored for general or respiratory distress, depression or in appetence and weight gain over the course of 30 days post inoculation. In another experiment, 6 embryonated chicken eggs (ECEs) was divided into 2 groups of 3 each. At 18.5 days post incubation, ECEs were either inoculated with PBS (negative control) or with 100 ug of pQAC-N construct into the allantoic cavity. Embryo development and hatch rate of inoculated ECEs was monitored.

Vaccine efficacy studies—For all the vaccine experiments, birds were challenged with a dose of 6.5E9 genome copy no or $10^{6.5}$ $EID_{50}$/bird of virulent IBV Arkansas DPI strain via direct intranasal instillations. The challenge dose was determined in an independent infection experiment wherein the challenge dose resulted in discernable clinical signs as early as 3 dpc and peak viral load replication was observed at 6 dpc. The protective efficacy of pQAC-N construct was evaluated in 1-day-old white leghorn SPF chicks (Charles River Laboratories). A total of 50 chicks was divided equally into 5 groups (n=10 each) and used for the efficacy study, first 2 groups were inoculated with PBS (negative control) or commercial Arkansas MLV (Mildvac-Ark®, Merck Animal Health USA, positive control) via direct intranasal instillations (dose according to manufacturer's instructions). The other groups were either vaccinated with naked (no adjuvant), chitosan complexed or pQAC-N at day-1 and followed by a booster dose at day-14 via intranasal (IN) route. A vaccine dose (100 ng/bird) was administered at each vaccination time point. At 20 days post first vaccination time point (DPV), PBMCs were harvested from blood collected using previously described protocols for proliferation assay (see below). At 10, 20 DPV & 3 days post challenge (DPC) lachrymal fluid (tears) samples were harvested for ELISA and and at 6 DPC for viral load estimation (see below). Lachrymation was induced by placing sodium chloride (salt) crystals on the eyes and tears were collected using micropipettes (52). Clinical severity was noted everyday post challenge for 8 days. The severity scores of clinical signs of IBV were as follows; 0=normal, 1=Infrequent sneezing (single event during observation), 2=frequent sneezing (more than one event during observation), 1=mild rales, 2=severe rales, 2=presence of nasal exudate. The severity scores of IBV clinical signs, described in the figure legends were recorded once a day for each chicken for 8 days after challenge. The severity score represents as average score of clinical signs measured for each chicken over 8 days (53). Lachrymal fluid harvested at 6 dpc was analyzed for viral RNA using IBV N gene specific RT-qPCR.

In another experiment, pQAC-N was used to immunize 1-day-old commercial white leghorn chicks (Cackle Hatchery®, MO, USA). A total of 10 chicks was divided into 2 groups. Chicks from the first group (n=4) was inoculated with PBS (negative control) while the second group (n=6) was immunized with pQAC-N construct at day-1 and followed by a booster dose at day-14 via intranasal (IN) route. Blood was collected from birds in the negative control group at day-10, 20 and 24 in age to quantitate MDA IgY. All birds were sampled, challenged and followed for clinical scores and virus titers as described above for the SPF chicks.

In the final experiment, pQAC-N was used to immunize 3-day-old commercial white leghorn chicks (Welp Hatchery, IA, USA). A total of 35 chicks was divided into 3 groups. Chicks were either inoculated with PBS (negative control, n=11) or commercial Arkansas MLV (Mildvac-Ark®, Merck Animal Health USA, positive control, n=12) or with pQAC-N construct at day-3 and followed by a booster dose at day-17 (14 dpv) via intranasal (IN) route as described above. Blood was collected from all the birds at 0, 10, 20 and 24 dpv to quantitate MDA IgY and lachrymal fluid from all the birds at 10, 20 and 24 dpv to quantitate IBV specific IgA. All birds were sampled, challenged and followed for clinical scores as described above for the SPF chicks. Tracheal swabs were taken at 6 dpc and analyzed for viral RNA using IBV N gene specific RT-qPCR. One bird in MLV group died at 10 dpv, one bird from MLV and PBS control groups each were euthanized at 12 dpv for necropsy and diagnosis by the Wisconsin Veterinary Diagnostic Laboratory (WVDL), Madison, Wis., USA.

Recombinant protein purification—The pCAG constructs with S1 6×His and $N_6$×His were transfected into Expi293F cells as described above using TransIT PRO transfection reagent according to manufacturer's instructions (Minis Bio, WI, USA). For S 1 6×His purification, supernatant was harvested and for $N_6$×His purification, cells were harvested 3 days after transfection. The samples were purified using Thermo Scientific™ HisPur™ Ni-NTA Resin according to manufacturer's instructions (batch method). The protein was eluted with elution buffer (50 mM sodium phosphate, 0.3 M sodium chloride, 250 mM imidazole pH 8.0). The eluate was concentrated using PEG-20 solution (800 mg/ml) hygroscopically and dialyzed using Thermo Scientific™ SnakeSkin™ Dialysis Tubing (7K MWCO) against PEG free PBS. Protein concentration was determined by Thermo Scientific™ Pierce™ BCA Protein Assay Kit.

IBV specific ELISA—Sera and lachrymal fluid from different time-points were screened for humoral response against IBV Arkansas serotype. In order to measure IgY and IgA antibody levels in plasma and tears of chicken respectively, an IBV-specific enzyme-linked immunosorbent assay (ELISA) was developed as described previously with modifications(54). Briefly, ELISA plates were coated with inactivated IBV Arkansas (100 ng/well, IgY) or IBV Arkansas S1 and N6×His protein (50 ng total/well, IgA) diluted in carbonate/bicarbonate buffer, pH 9.6 and incubated overnight at 4 C followed by blocking with 5% Skim milk to reduce background. A 50 ul of diluted serum (1/200) or tears (1/50) harvested at different time-points from immunized chickens was added to the wells and incubated at 37 C for 1 hour. Post washing (PBS-TritonX 100, 0.1%), either HRP conjugated anti-chicken IgY (NBP1-74778, NOVUS Bio) or anti-chicken IgA (NB7284, NOVUS Bio) at dilutions of 1/1000 was added to the wells and incubated at 37° C. for 1 hr. Post washing, 50 ul of TMB substrate solution was added and incubated for 20 minutes or until color developed. The reaction was stopped by the addition of 1M sulphuric acid and plates are read at 450 nm. To generate standard curves, sera and tears from severely IBV infected chickens from previous experiments was used. Two-fold serial dilutions was assigned and arbitrary value and used for analysis.

Assessment of IBV specific lymphocyte proliferation assay—PBMCs were prepared from harvested blood as described previously (46). PBMCs were adjusted to $10^7$ cells/ml in RPMI 1640 (Invitrogen) supplemented with 10% inactivated fetal calf serum and 100 μl cells per well were transferred into flat-bottomed 96-well plates. Equal volumes of medium containing stimulant (IBV Ark DPI live virus, MOI=1) was added in triplicate and cultures were incubated for 2 days at 41° C., 5% $CO_2$. Negative controls received 100 μl RPMI 1640 medium only. After incubation, to each well, 15 μl of MTT reagent (CellTiter 96® Non-Radioactive Cell Proliferation Assay, Promega) and cells incubated for a further 4 hrs at 41° C., 5% $CO_2$ until development of MTT (3-(4,5-dimethylthiazole-2-yl)-2,5-diphenyl-tetrazolium bromide) formazan was observed. Post incubation, Dimethyl sulfoxide (DMSO) was added to dissolve the formazan crystals and incubated for an hour at 41° C., 5% $CO_2$. The absorbance of the purple color was taken at 570 nm in an ELISA plate reader. PBMCs from 4 chicks/group was used to assess proliferative capacity. The output stimulation index (SI) is the ratio of absorbance post stimulation to the absorbance in unstimulated conditions.

Viral load measurement—RNA was extracted from lachrymal fluid (10 μl) or Tracheal swabs (100 μl) collected from chickens using Zymo Direct-Zol™ RNA mini prep kit (Zymo Research, CA, USA) according to manufacturer's instructions. RT-qPCR was conducted in two steps: cDNA synthesis (Invitrogen™ SuperScript™ III First-Strand Synthesis System) and qPCR reactions. cDNA synthesis was performed with 0.5 μl (50 ng/μl) random hexamers, 0.5 μl of 10 mM dNTPs, and 4 μl RNA and heated at 65° C. for 5 min and chilled on ice followed by addition of 1 μl of 10×RT buffer, 1 μl of 0.1 M DTT, 1 μl of 25 mM $MgCl_2$, 0.5 μl of RNaseOUT and 0.5 μl of SuperScript III enzyme in final volume of 10 μl. The reaction conditions include 25° C. for 5 min, 50° C. for 60 min and 70° C. for 15 min. SYBR green RT-qPCR was performed using an IBV N gene specific primer pair set forward primer: 5' ATGCTCAACCTAGTCCCTAGCA 3' (SEQ ID NO: 17) and reverse primer: 5' TCAAACTGCGGATCATCACGT 3' (SEQ ID NO: 18) amplifying 128 nt of N gene of IBV Arkansas DPI. PCRs were performed using a StepOnePlus™ Real-Time PCR System (Applied Biosystems, Foster City, Calif., U.S.A) under the following conditions: one cycle 95 C for 2 min followed by 40 cycles of 95 C for 3 sec and 60 C for 30 sec. Each 20 μl reaction was carried out using 1 μl of diluted cDNA (1/10), 10 μl of GoTaq® qPCR mastermix (Promega), 2 μl of forward and reverse primers and 7 μl of nuclease free water. A serial 10-fold dilution of pCAG-IBV Ark N6×His plasmid was used to establish the standard curve. Temperature melt curve analysis was used to confirm the specificity of the product.

Flow cytometric assessment of IBV specific proliferation—A subgroup of additional chicks (N=4 each) from each vaccine group in the SPF chick vaccine efficacy study were used for flow cytometric assessment. All chicks were euthanized at 20 DPV and single cell suspensions from lungs were prepared using standard techniques and used for T-cell proliferation assay. Briefly, lungs were excised and placed in a gentleMACS dissociator M tube (Miltenyi 130-093-236) with 5 mL collagenase B (2 mg/ml, Roche). Lung tissue was processed using the gentleMACS dissociator followed by incubation for 30 min at 37° C. Single-cell suspensions lung were prepared by gently squeezing through a 70-mm cell strainer (Falcon) after lysing RBCs using 1× BD Biosciences BD Pharm Lyse™. Total of $10^7$ cells/mi were stained with CellTrace™ Violet Cell Proliferation dye (Thermo Scientific C34557) according to manufacturer's instructions and 100 ul of cells plated/well in RPMI 1640 with 10% chicken immune serum. After overnight incubation at 41° C., 5% $CO_2$, cells were stimulated with 130 ng of IBV Arkansas N6×His protein complexed with chitosan per well in 100 ul of RPMI 1640 with 10% chicken immune serum. Four days post stimulation, cells were stained for surface markers, CD4-AF647 (clone CT-4), CD8α-FITC (clone 3-298) together and TCRγδ-FITC (clone TCR-1) independently for flow cytometry analysis. All antibodies were purchased from SouthernBiotech (Birmingham, Ala., USA). All samples were acquired on an BD LSR Fortessa flow cytometer. Data were analyzed with FlowJo software (BD Biosciences). The strategy for gating on proliferating CD4+ and CD8a+ T cells was debris exclusion on the Forward Scatter (FSC)-Side Scatter (SSC) dot plot followed by exclusion of dead cells by fixable viability dye eFluor 780 (Invitrogen™, #65-0865-14) staining. Out of the live cells, total proliferated cells were gated positive using a histogram plot with ef450 on the x-axis (for CellTrace™ Violet). Finally, CD4 cells were gated positive at the AF647 axis and CD8a cells were gated positive at the FITC axis in a FITC-AF647 dot plot. A similar approach was used for identifying proliferating TCRγδ+ T-cells. The output, stimulation index (SI) is the ratio of % proliferating cells post stimulation to the % proliferating cells in unstimulated condition.

Statistical analysis—Statistical analyses were performed using GraphPad software (La Jolla, Calif.). Weight gain, cellular immune assays, clinical severity scoring, viral loads were compared using an ordinary one-way ANOVA test with multiple comparisons where *, P<0.05; , P<0.01; *, P<0.001; ****, P<0.0001 were considered significantly different among groups. Antibody titers and absolute weight of birds were compared using a two-way ANOVA test where *, P<0.05; , P<0.01; *, P<0.001; ****, P<0.0001 were considered significantly different among groups.

REFERENCES

1. Cook J K A, Jackwood M, Jones R C. 2012. The long view: 40 years of infectious bronchitis research, vol 41, p 239-250.
2. Britton P, Armesto M, Cavanagh D, Keep S. 2012. Modification of the avian coronavirus infectious bronchitis virus for vaccine development. Bioengineered Bugs 3:114-119.
3. Geilhausen H E, Ligon F B, Lukert P D. 1973. The pathogenesis of virulent and avirulent avian infectious bronchitis virus. Archiv f├╝r die gesamte Virusforschung 40:285-290.
4. Dolz R, Vergara-Alert J l, P¬⊢rez Mn, Pujols J, Maj⊢lNá. 2012. New insights on infectious bronchitis virus pathogenesis: Characterization of Italy 02 serotype in chicks and adult hens. Veterinary Microbiology 156:256-264.
5. Han Z, Sun C, Yan B, Zhang X, Wang Y, Li C, Zhang Q, Ma Y, Shao Y, Liu Q, Kong X, Liu S. 2011. A 15-year analysis of molecular epidemiology of avian infectious bronchitis coronavirus in China. Infection, Genetics and Evolution 11:190-200.
6. Fraga A P, Balestrin E, Ikuta N, Fonseca A S K, Spilki F R, Canal CíW, Lunge V R. 2013.
Emergence of a New Genotype of Avian Infectious Bronchitis Virus in Brazil. Avian Diseases 57:225-232.
7. Cook J K, Jackwood M, Jones R C. 2012. The long view: 40 years of infectious bronchitis research. Avian Pathol 41:239-50.
8. de Wit J J, Cook J K A, van der Heijden H M J F. 2010. Infectious bronchitis virus in Asia, Africa, Australia and Latin America—history, current situation and control measures. Brazilian Journal of Poultry Science 12:97-106.

9. Cavanagh D, Ellis M M, Cook J K A. 1997. Relationship between sequence variation in the S1 spike protein of infectious bronchitis virus and the extent of cross-protection in vivo. Avian Pathology 26:63-74.
10. Gelb J, Weisman Y, Ladman B S, Meir R. 2005. S1 gene characteristics and efficacy of vaccination against infectious bronchitis virus field isolates from the United States and Israel (1996 to 2000). Avian Pathology 34:194-203.
11. Jackwood M W, Hilt D A, McCall A W, Polizzi C N, McKinley E T, Williams S M. 2009. Infectious bronchitis virus field vaccination coverage and persistence of Arkansas-type viruses in commercial broilers. Avian Dis 53:175-83.
12. Hopkins S R Y H J. 1986. Reversion to virulence of chicken-passaged infectious bronchitis vaccine virus. Avian Diseases.
13. McKinley E T, Hilt D A, Jackwood M W. 2008. Avian coronavirus infectious bronchitis attenuated live vaccines undergo selection of subpopulations and mutations following vaccination. Vaccine 26:1274-84.
14. Lee C W, Jackwood M W. 2001. Origin and evolution of Georgia 98 (GA98), a new serotype of avian infectious bronchitis virus. Virus Research 80:33-39.
15. Wolff J A, Malone R W, Williams P, Chong W, Acsadi G, Jani A, Felgner P L. 1990. Direct gene transfer into mouse muscle in vivo. Science 247:1465-8.
16. Jazayeri S D, Poh C L. 2019. Recent advances in delivery of veterinary DNA vaccines against avian pathogens. Vet Res 50:78.
17. Liu M A. 2003. DNA vaccines: a review. J Intern Med 253:402-10.
18. Zhang P, Wang J, Wang W, Liu X, Liu H, Li X, Wu X. 2017. *Astragalus* polysaccharides enhance the immune response to avian infectious bronchitis virus vaccination in chickens. Microb Pathog 111:81-85.
19. Kapczynski D R, Hilt D A, Shapiro D, Sellers H S, Jackwood M W. 2003. Protection of chickens from infectious bronchitis by in ovo and intramuscular vaccination with a DNA vaccine expressing the 51 glycoprotein. Avian Dis 47:272-85.
20. Guo Z, Wang H, Yang T, Wang X, Lu D, Li Y, Zhang Y. 2010. Priming with a DNA vaccine and boosting with an inactivated vaccine enhance the immune response against infectious bronchitis virus. J Virol Methods 167:84-9.
21. Tan L, Zhang Y, Liu F, Yuan Y, Zhan Y, Sun Y, Qiu X, Meng C, Song C, Ding C. 2016. Infectious bronchitis virus poly-epitope-based vaccine protects chickens from acute infection. Vaccine 34:5209-5216.
22. Tian L, Wang H N, Lu D, Zhang Y F, Wang T, Kang R M. 2008. The immunoreactivity of a chimeric multi-epitope DNA vaccine against IBV in chickens. Biochem Biophys Res Commun 377:221-5.
23. Tang M, Wang H, Zhou S, Tian G. 2008. Enhancement of the immunogenicity of an infectious bronchitis virus DNA vaccine by a bicistronic plasmid encoding nucleocapsid protein and interleukin-2. J Virol Methods 149:42-8.
24. Tan B, Wang H, Shang L, Yang T. 2009. Coadministration of chicken G M-CSF with a DNA vaccine expressing infectious bronchitis virus (IBV) 51 glycoprotein enhances the specific immune response and protects against IBV infection. Arch Virol 154:1117-24.
25. Yan F, Zhao Y, Hu Y, Qiu J, Lei W, Ji W, Li X, Wu Q, Shi X, Li Z. 2013. Protection of chickens against infectious bronchitis virus with a multivalent DNA vaccine and boosting with an inactivated vaccine. J Vet Sci 14:53-60.
26. Yang T, Wang H N, Wang X, Tang J N, Gao R, Li J, Guo Z C, Li Y L. 2009. Multivalent DNA vaccine enhanced protection efficacy against infectious bronchitis virus in chickens. J Vet Med Sci 71:1585-90.
27. Oyewumi M O, Kumar A, Cui Z. 2010. Nano-microparticles as immune adjuvants: correlating particle sizes and the resultant immune responses. Expert Rev Vaccines 9:1095-107.
28. Borges O, Borchard G, Verhoef J C, de Sousa A, Junginger H E. 2005. Preparation of coated nanoparticles for a new mucosal vaccine delivery system. Int J Pharm 299:155-66.
29. Brock A. Kingstad-Bakke S S C, YashdeepPhanse, Kathleen A. Ross, MasatoHatta, M. Suresh, Yoshihiro Kawaoka, Jorge E. Osorio, Balaji Narasimhan, Adel M. Talaat. 2019. Effective mosaic-based nanovaccines against avian influenza in poultry. Vaccine.
30. Riteau N, Sher A. 2016. Chitosan: An Adjuvant with an Unanticipated STING. Immunity 44:522-524.
31. Sogias I A, Williams A C, Khutoryanskiy V V. 2008. Why is chitosan mucoadhesive? Biomacromolecules 9:1837-42.
32. Rajput Z I, Hu S H, Xiao C W, Arijo A G. 2007. Adjuvant effects of saponins on animal immune responses. J Zhejiang Univ Sci B 8:153-61.
33. Seo S H, Wang L, Smith R, Collisson E W. 1997. The carboxyl-terminal 120-residue polypeptide of infectious bronchitis virus nucleocapsid induces cytotoxic T lymphocytes and protects chickens from acute infection. J Virol 71:7889-94.
34. Chhabra R, Chantrey J, Ganapathy K. 2015. Immune Responses to Virulent and Vaccine Strains of Infectious Bronchitis Viruses in Chickens. Viral Immunol 28:478-88.
35. Collisson E W, Pei J, Dzielawa J, Seo S H. 2000. Cytotoxic T lymphocytes are critical in the control of infectious bronchitis virus in poultry. Dev Comp Immunol 24:187-200.
36. Seo S H, Pei J, Briles W E, Dzielawa J, Collisson E W. 2000. Adoptive transfer of infectious bronchitis virus primed alphabeta T cells bearing CD8 antigen protects chicks from acute infection. Virology 269:183-9.
37. Mockett A P, Cook J K, Huggins M B. 1987. Maternally-derived antibody to infectious bronchitis virus: Its detection in chick trachea and serum and its role in protection. Avian Pathol 16:407-16.
38. Mondal S P, Naqi S A. 2001. Maternal antibody to infectious bronchitis virus: its role in protection against infection and development of active immunity to vaccine. Vet Immunol Immunopathol 79:31-40.
39. de Wit J J, Cook J K. 2014. Factors influencing the outcome of infectious bronchitis vaccination and challenge experiments. Avian Pathol 43:485-97.
40. Roy K, Mao H Q, Huang S K, Leong K W. 1999. Oral gene delivery with chitosan—DNA nanoparticles generates immunologic protection in a murine model of peanut allergy. Nat Med 5:387-91.
41. Ho N I, Huis In't Veld L G M, Raaijmakers T K, Adema G J. 2018. Adjuvants Enhancing Cross-Presentation by Dendritic Cells: The Key to More Effective Vaccines? Front Immunol 9:2874.
42. Behzadi S, Serpooshan V, Tao W, Hamaly M A, Alkawareek M Y, Dreaden E C, Brown D, Alkilany A M, Farokhzad O C, Mahmoudi M. 2017. Cellular uptake of nanoparticles: journey inside the cell. Chem Soc Rev 46:4218-4244.
43. Harush-Frenkel O, Debotton N, Benita S, Altschuler Y. 2007. Targeting of nanoparticles to the clathrin-mediated endocytic pathway. Biochem Biophys Res Commun 353:26-32.

44. Mohammed M A, Syeda J T M, Wasan K M, Wasan E K. 2017. An Overview of Chitosan Nanoparticles and Its Application in Non-Parenteral Drug Delivery. Pharmaceutics 9.
45. Chhabra R, Forrester A, Lemiere S, Awad F, Chantrey J, Ganapathy K. 2015. Mucosal, Cellular, and Humoral Immune Responses Induced by Different Live Infectious Bronchitis Virus Vaccination Regimes and Protection Conferred against Infectious Bronchitis Virus Q1 Strain. Clin Vaccine Immunol 22:1050-9.
46. Norup L R, Dalgaard T S, Pedersen A R, Juul-Madsen H R. 2011. Assessment of Newcastle disease-specific T cell proliferation in different inbred MHC chicken lines. Scand J Immunol 74:23-30.
47. Hamers C, Juillard V, Fischer L. 2007. DNA vaccination against pseudorabies virus and bovine respiratory syncytial virus infections of young animals in the face of maternally derived immunity. J Comp Pathol 137 Suppl 1:S35-41.
48. Griot C, Moser C, Cherpillod P, Bruckner L, Wittek R, Zurbriggen A, Zurbriggen R. 2004. Early DNA vaccination of puppies against canine distemper in the presence of maternally derived immunity. Vaccine 22:650-4.
49. Zhang F, Peng B, Chang H, Zhang R, Lu F, Wang F, Fang F, Chen Z. 2016. Intranasal Immunization of Mice to Avoid Interference of Maternal Antibody against H5N1 Infection. PLoS One 11:e0157041.
50. Ignjatovi-ç J, Sapats S. 2000. Avian infectious bronchitis virus. Revue scientifique et technique (International Office of Epizootics) 19:493-508.
51. MUENCH LJRAH. 1938. A SIMPLE METHOD OF ESTIMATING FIFTY PERCENT ENDPOINTS THE AMERICAN JOURNAL OF HYGIENE 27.
52. Ganapathy K, Cargill P W, Jones R C. 2005. A comparison of methods of inducing lachrymation and tear collection in chickens for detection of virus-specific immuoglobulins after infection with infectious bronchitis virus. Avian Pathol 34:248-51.
53. Shirvani E, Paldurai A, Manoharan V K, Varghese B P, Samal S K. 2018. A Recombinant Newcastle Disease Virus (NDV) Expressing S Protein of Infectious Bronchitis Virus (IBV) Protects Chickens against IBV and NDV. Sci Rep 8:11951.
54. Orr-Burks N, Gulley S L, Toro H, van Ginkel F W. 2014. Immunoglobulin A as an early humoral responder after mucosal avian coronavirus vaccination. Avian Dis 58:279-86.

Example 2

This prophetic example outlines a QAC complex antigen in vivo cross presentation study. Antigen cross presentation is important for effective immune response to tumors and viral infections. Dendritic cells are antigen presenting cells and are unique in their ability to cross-present exogenous antigens on MHC class I molecules and activate antigen specific cytotoxic T cells. This study examines the function of the QAC complex to mediate antigen cross presentation by dendritic cells (DCs, specifically, bone marrow derived DCs and splenic DCs) in an in vivo assay system using soluble ovalbumin protein (OVA).

Figure 15:
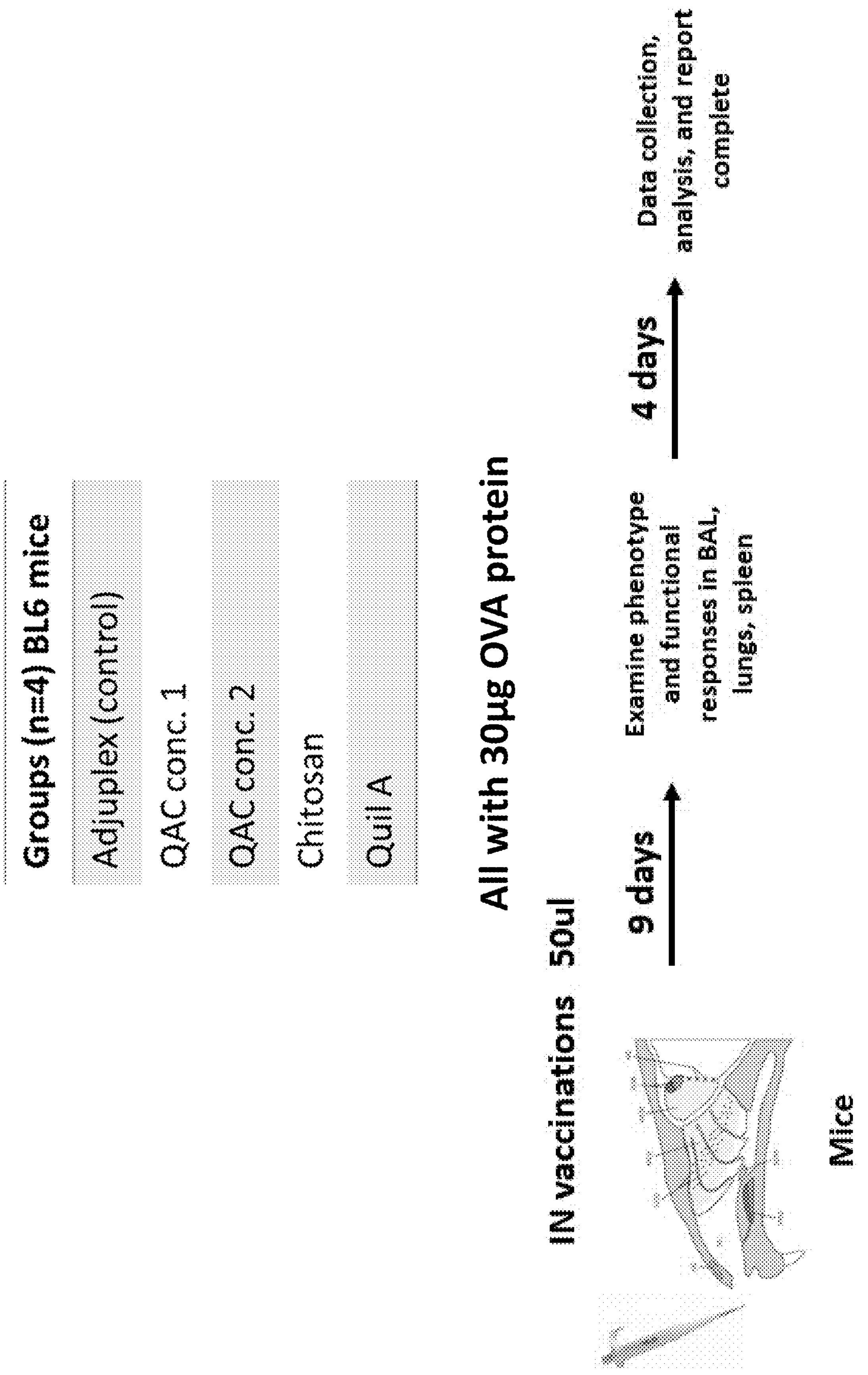
FIG. 15 shows an in vivo cross presentation study in mice using the QAC complex loaded with ovalbumin protein (OVA).

BL6 mice will be separated into groups (n=4) corresponding to treatment with Adjuplex control, a first concentration of QAC complex loaded with 30 µg OVA protein, a second concentration of QAC complex loaded with 30 µg OVA protein, chitosan loaded with 30 µg OVA protein, and Quail-A loaded with 30 µg OVA protein. Mice will receive a 50 µL intra nasal vaccination with the selected treatment. After 9 days, phenotype and functional responses in bronchoalveolar lavage (BAL), lungs, and spleen will be assessed. At 13 days post treatment, data collection and further analysis on the mice will be carried out. (FIG. 15) Phenotypic parameters measured include MHCI tetramers specific to ovalbumin peptide sequence SIINFEKL (SIINFEKL MHCI tetramers, SEQ ID NO: 19), CD103 and CD69 tissue residency, and KLRG1, CD127, CD44, and CD62L expression. Functional parameters measured include ovalbumin immunogenic peptide CD8 sequence SIINFEKL (OVA I CD8 SIINFEKL, SEQ ID NO: 19), ovalbumin immunogenic peptide CD4 sequence ISQAVHAAHAEINEAGR (OVA II CD4 ISQAVHAAHAEINEAGR, SEQ ID NO: 20), and expression of CD4, CD8, IL-2, IL-4, IL-6, IL-10, IL-13, IL-17, IFNg, and TNFa.

This study will confirm that the cross presentation measured in vitro in primary DC cells using the QAC complex is mirrored in vivo. Additionally, the mouse experiment will generate a model immunologic system for QAC mediated cross presentation in vivo for other antigens and immunogens.

Example 3

This prophetic example outlines an in vivo study to measure innate and adaptive immune responses to the loaded QAC complex. The QAC complex can strongly induce cross presentation with OVA in vitro in DC cells. The mouse study presented provides a model immunologic system for the study of in vivo QAC complex induced cross presentation. Measurements including antigen presenting cells will strongly augment the adjuvant mechanism. Chitosan has been demonstrated to work in vitro, but will not function in vivo for protein antigens. The present studies will confirm the function of the QAC complex in antigen presenting cell recruitment and activation.

Figure 16:
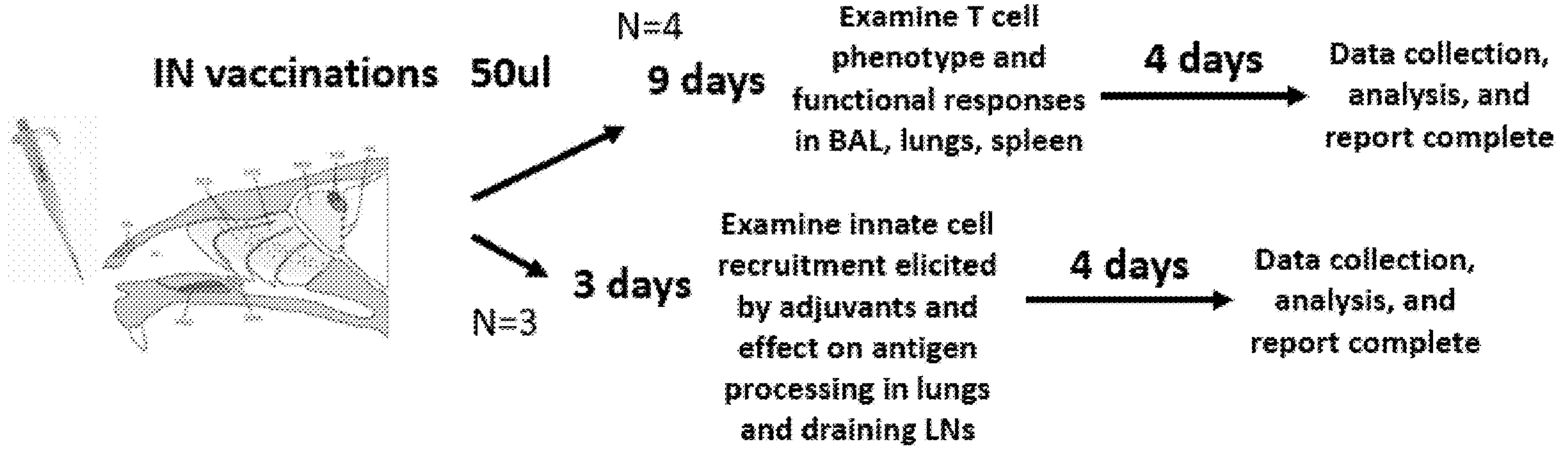
FIG. 16 shows an in vivo study to measure innate and adaptive immune responses following treatment with the QAC complex loaded with OVA.
Figure 17:
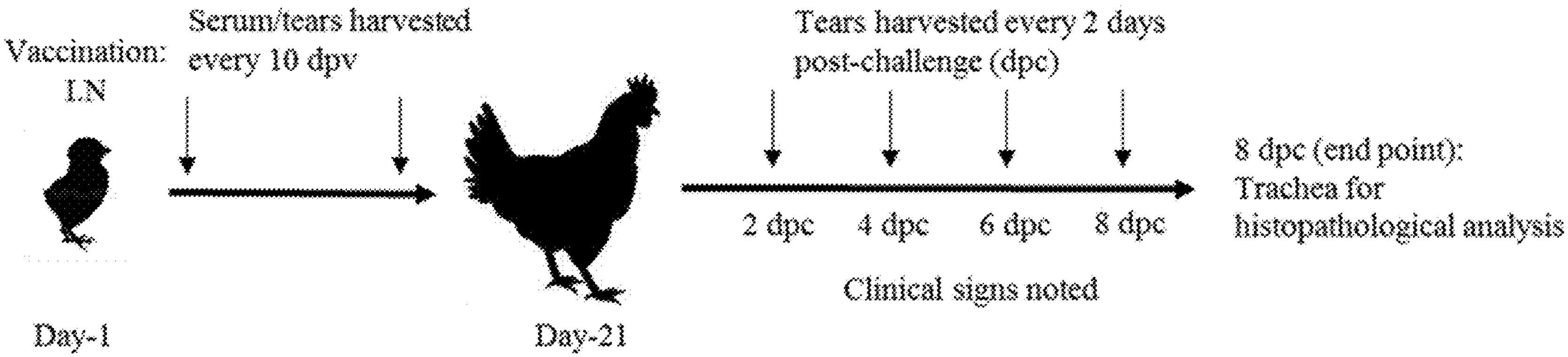
FIG. 17 shows an in vivo study measuring protein immunogen immune response in chickens treated with the QAC complex loaded with whole inactivated infectious bronchitis virus (IBV).

BL6 mice will be separated into groups (n=7) corresponding to treatment with Adjuplex control, a first concentration of QAC complex loaded with 30 µg OVA protein or DQ-OVA protein, a second concentration of QAC complex loaded with 30 µg OVA protein or DQ-OVA protein, chitosan loaded with 30 µg OVA protein or DQ-OVA, and Quail-A loaded with 30 µg OVA protein or DQ-OVA. Mice will receive a 50 µL intra nasal injection of the indicated treatment. After 3 days, mice treated with DQ-OVA will be examined for innate cell recruitment elicited by adjuvants and its effect on antigen processing in lungs and draining lymph nodes (LNs). At 7 days post treatment data collection and further analysis on the mice will be carried out. (FIG. 16). At 4 days after treatment, mice treated with OVA will be examined for T cell phenotype and functional responses in BAL, lungs, and spleen. At 13 days post treatment, data collection and further analysis on the mice will be carried out.

Phenotypic parameters measured in T cells will include SIINFEKL MHC I tetramers, and expression of CD103, CD69, KLRG1, CD127, CD44, and CD62L. Functional parameters measured include OVA I CD8 SIINFEKL, OVA II CD4 ISQAVHAAHAEINEAGR, and expression of CD4, CD8, IL-2, IL-4, IL-6, IL-10, IL-13, IL-17, IFNg, and TNFa. Parameters measured in innate immune cells include antigen uptake, such as uptake of unprocessed Texas Red or digested GFP, and analysis of antigen presenting cells including neutrophils, Alv macs, Eosinophils, CD103 cDCs, monocyte derived DCs, monocyte, Natural Killer cells, and new cell subsets. Antigen presenting cells (APCs) will be analyzed using flow cytometry to assay for antigen uptake which is essentially a flurophore encapsulated by QAC. If there is efficient antigen uptake, antigen presenting cells would have taken up the flurophore. Potent adjuvants are able to efficiently deliver payload to APCs and mediate antigen uptake.

We claim:

1. A composition comprising disaggregated spherical nanostructures comprising Quil-A and chitosan, wherein the Quil-A and chitosan are present at a ratio between 1:15 weight:weight, and 1:100 weight:weight.

2. The composition of claim 1, additionally comprising a payload molecule.

3. The composition of claim 2, wherein the payload molecule is selected from the group consisting of a DNA molecule, an RNA molecule, a polynucleotide.

4. The composition of claim 2, wherein the payload molecule is negatively charged.

5. The composition of claim 2, wherein the payload is functionalized.

6. The composition of claim 1, wherein the chitosan is functionalized by treatment with 5-formyl-2-furan sulfonic acid and sodium borohydride such that the chitosan surface is negatively charged.

7. The composition of claim 1, wherein the spherical nanostructures are between about 5 nm and about 100 nm in diameter in the absence of a payload molecule.

8. A vaccine formulation comprising an antigen, the composition of claim 1 as an adjuvant, and a pharmaceutically acceptable carrier.

9. A vaccine formulation comprising the composition of claim 1.

10. A method of immunizing a subject against an antigen comprising the step of administering to the subject a vaccine formulation comprising the composition of claim 1.

11. The method of claim 10, wherein the subject is selected from the group consisting of a human, a mouse, a rat, a cow, a horse, a pig, a goat, a sheep, a cat, a dog, or a bird.

* * * * *

UNITED STATES PATENT AND TRADEMARK OFFICE

CERTIFICATE OF CORRECTION

PATENT NO. : 11,771,761 B2
APPLICATION NO. : 16/900070
DATED : October 3, 2023
INVENTOR(S) : Adel M. Talaat et al.

It is certified that error appears in the above-identified patent and that said Letters Patent is hereby corrected as shown below:

In the Specification

Column 3, Line 4, "(51)" should be --(S1)--.

Column 4, Line 9, "OVA257-264" should be --$OVA_{257-264}$--.

Column 17, Line 66, "sub species" should be --subspecies--.

Column 18, Line 61, "D3" should be --IB--.

Column 19, Line 12, "51" should be --S1--.

Column 19, Line 28, "51" should be --S1--.

Column 21, Line 28, "51" should be --S1--.

Column 21, Line 23, "51" should be --S1--.

Column 22, Line 61, "51" should be --S1--.

Column 22, Line 63, "51" should be --S1--.

Column 28, Line 23, "Minis" should be --Mirus--.

Column 28, Line 24, "S 1" should be --S1--.

Column 29, Line 59, "cell/mi" should be --cell/ml--.

Signed and Sealed this
Thirtieth Day of April, 2024

Katherine Kelly Vidal

Katherine Kelly Vidal
*Director of the United States Patent and Trademark Office*

Column 31, Line 40, “51” should be --S1--.

Column 31, Line 61, “51” should be --S1--.

SEQUENCE LISTING

<160> NUMBER OF SEQ ID NOS: 20

<210> SEQ ID NO 1
<211> LENGTH: 6051
<212> TYPE: DNA
<213> ORGANISM: Artificial Sequence
<220> FEATURE:
<223> OTHER INFORMATION: synthetic

<400> SEQUENCE: 1

```
gtcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggact atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atgggtcgag gtgagcccca cgttctgctt cactctcccc    420

atctcccccc cctccccacc cccaattttg tatttattta tttttaatt attttgtgca     480

gcgatggggg cggggggggg gggggcgcgc gccaggcggg gcggggcggg gcgaggggcg    540

gggcggggcg aggcggagag gtgcggcggc agccaatcag agcggcgcgc tccgaaagtt    600

tccttttatg gcgaggcggc ggcggcggcg gccctataaa aagcgaagcg cgcggcgggc    660

gggagtcgct gcgttgcctt cgccccgtgc cccgctccgc gccgcctcgc gccgcccgcc    720

ccggctctga ctgaccgcgt tactcccaca ggtgagcggg cgggacggcc cttctcctcc    780

gggctgtaat tagcgcttgg tttaatgacg gctcgtttct tttctgtggc tgcgtgaaag    840

ccttaaaggg ctccgggagg gccctttgtg cggggggggag cggctcgggg ggtgcgtgcg    900

tgtgtgtgtg cgtggggagc gccgcgtgcg gcccgcgctg cccggcggct gtgagcgctg    960

cgggcgcggc gcggggcttt gtgcgctccg cgtgtgcgcg aggggagcgc ggccgggggc   1020

ggtgccccgc ggtgcggggg ggctgcgagg ggaacaaagg ctgcgtgcgg ggtgtgtgcg   1080

tgggggggtg agcagggggt gtgggcgcgg cggtcgggct gtaacccccc cctgcacccc   1140

cctccccgag ttgctgagca cggcccggct tcgggtgcgg ggctccgtgc ggggcgtggc   1200

gcggggctcg ccgtgccggg cgggggggtgg cggcaggtgg gggtgccggg cggggcgggg   1260

ccgcctcggg ccggggaggg ctcgggggag ggcgcggcg gcccccggag cgccggcggc    1320

tgtcgaggcg cggcgagccg cagccattgc cttttatggt aatcgtgcga gagggcgcag   1380

ggacttcctt tgtcccaaat ctgtgcggag ccgaaatctg ggaggcgccg ccgcaccccc   1440

tctagcgggc gcggggcgaa gcggtgcggc gccggcagga aggaaatggg cggggagggc   1500

cttcgtgcgt cgccgcgccg ccgtcccctt ctccctctcc agcctcgggg ctgtccgcgg   1560

ggggacggct gccttcgggg gggacggggc agggcggggt tcggcttctg gcgtgtgacc   1620

ggcggctcta gagcctctgc taaccatgtt catgccttct tctttttcct acagctcctg   1680

ggcaacgtgc tggttattgt gctgtctcat cattttggca aagaattcac catggcaagc   1740

ggtaaagcaa ctggaaagac agacgcccca gcgccagtca tcaaactagg aggaccaaag   1800

ccacctaaag ttggttcttc tggaaatgca tcttggtttc aagcaataaa agccaagaag   1860

ctaaattcac atccacctaa gtttgaaggt agcggtgttc ctgataatga aaatcttaaa   1920

acaagtcagc aacatggata ctggaggcgc caagccaggt ttaagccagt taaaggcgga   1980

agaaaaccag tcccagatgc ttggtacttc tattatactg gaacaggacc agccgctgac   2040
```

```
ctgaattggg gtgatagcca agatggtata gtgtgggttg ctgcaaaggg tgctgatgtt   2100
aaatctagat ctcaccaggg tacaagggac cctgacaagt ttgaccaata tccactacga   2160
ttctcggacg gaggacctga tggtaatttc cgttgggact tcattcctct gaatcgtggt   2220
aggagtggaa gatcaacagc agcttcatca gcagcatcta gtagagcacc gtcgcgtgac   2280
ggctcgcgtg gtcgtagaag tggttctgaa gatgatctta ttgctcgtgc agcaaagata   2340
atccaggatc agcagaagaa gggttctcgc attactaagg ttaaggctga tgaaatggct   2400
caccgccggt attgcaagcg cactattcca cctggttata aggttgatca agtctttggc   2460
ccccgtacta aaggtaagga gggaaatttt ggtgatgaca agatgaatga ggaaggtatt   2520
aaggatgggc gtgttacagc aatgctcaac ctagtcccta gcagccatgc ttgtcttttt   2580
ggaagtagag tgacgcccaa actacaacca gatgggctgc acttgaaatt tgaatttact   2640
actgtggtcc cacgtgatga tccgcagttt gataattatg ttaaaatttg tgatcagtgt   2700
gttgatggtg taggaacacg tccaaaagat gatgaaccga gaccaaagtc acgctcaagt   2760
tcaagacctg ctacaagaac aagttctccg gcgccaagac aacaacgccc aaagaaggag   2820
aaaaagccaa agaagcagga tgatgaagta gataaagcat tgacctcaaa tgaggagagg   2880
aacaatgcac agctggaatt tgatgaggaa cccaaggtga ttaactgggg ggatgcagct   2940
ctaggagaga atgaacttgg aggaggtcat catcaccatc accactaagc ggccgcactc   3000
ctcaggtgca ggctgcctat cagaaggtgg tggctggtgt ggccaatgcc ctggctcaca   3060
aataccactg agatcttttt ccctctgcca aaaattatgg ggacatcatg aagccccttg   3120
agcatctgac ttctggctaa taaaggaaat ttattttcat tgcaatagtg tgttggaatt   3180
ttttgtgtct ctcactcgga aggacatatg ggagggcaaa tcatttaaaa catcagaatg   3240
agtatttggt ttagagtttg gcaacatatg cccatatgct ggctgccatg aacaaaggtg   3300
gctataaaga ggtcatcagt atatgaaaca gccccctgct gtccattcct tattccatag   3360
aaaagccttg acttgaggtt agattttttt tatattttgt tttgtgttat tttttttcttt   3420
aacatcccta aaattttcct tacatgtttt actagccaga tttttcctcc tctcctgact   3480
actcccagtc atagctgtcc ctcttctctt atgaagatcc ctcgacctgc agcccaagct   3540
tggcgtaatc atggtcatag ctgtttcctg tgtgaaattg ttatccgctc acaattccac   3600
acaacatacg agccggaagc ataaagtgta aagcctgggg tgcctaatga gtgagctaac   3660
tcacattaat tgcgttgcgc tcactgcccg ctttccagtc gggaaacctg tcgtgccagc   3720
ggatccgcat ctcaattagt cagcaaccat agtcccgccc ctaactccgc ccatcccgcc   3780
cctaactccg cccagttccg cccattctcc gccccatggc tgactaattt tttttattta   3840
tgcagaggcc gaggccgcct cggcctctga gctattccag aagtagtgag gaggcttttt   3900
tggaggccta ggcttttgca aaaagctaac ttgtttattg cagcttataa tggttacaaa   3960
taaagcaata gcatcacaaa tttcacaaat aaagcatttt tttcactgca ttctagttgt   4020
ggtttgtcca aactcatcaa tgtatcttat catgtctgga tccgctgcat taatgaatcg   4080
gccaacgcgc ggggagaggc ggtttgcgta ttgggcgctc ttccgcttcc tcgctcactg   4140
actcgctgcg ctcggtcgtt cggctgcggc gagcggtatc agctcactca aaggcggtaa   4200
tacggttatc cacagaatca ggggataacg caggaaagaa catgtgagca aaaggccagc   4260
aaaaggccag gaaccgtaaa aaggccgcgt tgctggcgtt tttccatagg ctccgccccc   4320
ctgacgagca tcacaaaaat cgacgctcaa gtcagaggtg gcgaaacccg acaggactat   4380
```

-continued

```
aaagatacca ggcgtttccc cctggaagct ccctcgtgcg ctctcctgtt ccgaccctgc   4440
cgcttaccgg atacctgtcc gcctttctcc cttcgggaag cgtggcgctt tctcaatgct   4500
cacgctgtag gtatctcagt tcggtgtagg tcgttcgctc caagctgggc tgtgtgcacg   4560
aaccccccgt tcagcccgac cgctgcgcct tatccggtaa ctatcgtctt gagtccaacc   4620
cggtaagaca cgacttatcg ccactggcag cagccactgg taacaggatt agcagagcga   4680
ggtatgtagg cggtgctaca gagttcttga agtggtggcc taactacggc tacactagaa   4740
ggacagtatt tggtatctgc gctctgctga agccagttac cttcggaaaa agagttggta   4800
gctcttgatc cggcaaacaa accaccgctg gtagcggtgg tttttttgtt tgcaagcagc   4860
agattacgcg cagaaaaaaa ggatctcaag aagatccttt gatcttttct acggggtctg   4920
acgctcagtg gaacgaaaac tcacgttaag ggattttggt catgagatta tcaaaaagga   4980
tcttcaccta gatcctttta aattaaaaat gaagttttaa atcaatctaa agtatatatg   5040
agtaaacttg gtctgacagt taccaatgct taatcagtga ggcacctatc tcagcgatct   5100
gtctatttcg ttcatccata gttgcctgac tccccgtcgt gtagataact acgatacggg   5160
agggcttacc atctggcccc agtgctgcaa tgataccgcg agacccacgc tcaccggctc   5220
cagatttatc agcaataaac cagccagccg gaagggccga gcgcagaagt ggtcctgcaa   5280
ctttatccgc ctccatccag tctattaatt gttgccggga agctagagta agtagttcgc   5340
cagttaatag tttgcgcaac gttgttgcca ttgctacagg catcgtggtg tcacgctcgt   5400
cgtttggtat ggcttcattc agctccggtt cccaacgatc aaggcgagtt acatgatccc   5460
ccatgttgtg caaaaaagcg gttagctcct tcggtcctcc gatcgttgtc agaagtaagt   5520
tggccgcagt gttatcactc atggttatgg cagcactgca taattctctt actgtcatgc   5580
catccgtaag atgcttttct gtgactggtg agtactcaac caagtcattc tgagaatagt   5640
gtatgcggcg accgagttgc tcttgcccgg cgtcaatacg ggataatacc gcgccacata   5700
gcagaacttt aaaagtgctc atcattggaa aacgttcttc ggggcgaaaa ctctcaagga   5760
tcttaccgct gttgagatcc agttcgatgt aacccactcg tgcacccaac tgatcttcag   5820
catcttttac tttcaccagc gtttctgggt gagcaaaaac aggaaggcaa aatgccgcaa   5880
aaaagggaat aagggcgaca cggaaatgtt gaatactcat actcttcctt tttcaatatt   5940
attgaagcat ttatcagggt tattgtctca tgagcggata catatttgaa tgtatttaga   6000
aaaataaaca aataggggtt ccgcgcacat ttccccgaaa agtgccacct g            6051
```

<210> SEQ ID NO 2
<211> LENGTH: 8121
<212> TYPE: DNA
<213> ORGANISM: Artificial Sequence
<220> FEATURE:
<223> OTHER INFORMATION: synthetic

<400> SEQUENCE: 2

```
gtcgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420
```

-continued

```
atctcccccc cctccccacc cccaattttg tatttattta tttttttaatt attttgtgca    480
gcgatggggg cggggggggg gggggcgcgc gccaggcggg gcggggcggg gcgaggggcg    540
gggcggggcg aggcggagag gtgcggcggc agccaatcag agcggcgcgc tccgaaagtt    600
tccttttatg gcgaggcggc ggcggcggcg gccctataaa aagcgaagcg cgcggcgggc    660
gggagtcgct gcgttgcctt cgccccgtgc cccgctccgc gccgcctcgc gccgcccgcc    720
ccggctctga ctgaccgcgt tactcccaca ggtgagcggg cgggacggcc cttctcctcc    780
gggctgtaat tagcgcttgg tttaatgacg gctcgtttct tttctgtggc tgcgtgaaag    840
ccttaaaggg ctccgggagg gccctttgtg cggggggggag cggctcgggg ggtgcgtgcg    900
tgtgtgtgtg cgtggggagc gccgcgtgcg gcccgcgctg cccggcggct gtgagcgctg    960
cgggcgcggc gcggggcttt gtgcgctccg cgtgtgcgcg aggggagcgc ggccgggggc   1020
ggtgccccgc ggtgcggggg ggctgcgagg ggaacaaagg ctgcgtgcgg ggtgtgtgcg   1080
tgggggggtg agcagggggt gtgggcgcgg cggtcgggct gtaacccccc cctgcacccc   1140
cctccccgag ttgctgagca cggcccggct tcgggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcgggggag ggcgcggcgg gcccccggag cgccggcggc   1320
tgtcgaggcg cggcgagccg cagccattgc cttttatggt aatcgtgcga gagggcgcag   1380
ggacttcctt tgtcccaaat ctgtgcggag ccgaaatctg ggaggcgccg ccgcaccccc   1440
tctagcgggc gcggggcgaa gcggtgcggc gccggcagga aggaaatggg cggggagggc   1500
cttcgtgcgt cgccgcgccg ccgtcccctt ctccctctcc agcctcgggg ctgtccgcgg   1560
ggggacggct gccttcgggg gggacggggc agggcggggt tcggcttctg gcgtgtgacc   1620
ggcggctcta gagcctctgc taaccatgtt catgccttct tctttttcct acagctcctg   1680
ggcaacgtgc tggttattgt gctgtctcat cattttggca aagaattcac catgttggtg   1740
aagtcactgt ttctagtgac cattttgttt gcactatgta gtgctaattt atatgacaac   1800
gaatcttttg tgtattacta ccagagtgct tttaggccag gacatggttg gcatttacat   1860
ggaggtgctt atgcagtagt taatgtgtct agtgaaaata ataatgcagg tactgcccca   1920
agttgcactg ctggtgctat tggctacagt aagaatttca gtgcggcctc agtagccatg   1980
actgcaccac taagtggtat gtcatggtct gcctcatctt tttgtacagc tcactgtaat   2040
tttacttctt atatagtgtt tgttacacat tgttttaaga gcggatctaa tagttgtcct   2100
ttgacaggtc ttattccaag cggttatatt cgtattgctg ctatgaaaca tggaagtgct   2160
acgcctggtc acttatttta taacttaaca gtttctgtga ctaaatatcc taagtttaga   2220
tcgctacaat gtgttaataa tcatacttct gtatatttaa atggtgacct tgttttcaca   2280
tctaactata ctgaagatgt tgtagctgca ggtgtccatt ttaaaagtgg tggacctata   2340
acttataaag ttatgagaga ggttaaagcc ttggcttatt ttgtcaatgg tactgcacat   2400
gatgtcattc tatgtgatga cacacctaga ggtttgttag catgccaata taatactggc   2460
aatttttcag atggcttcta tccttttact aatactagta ttgttaagga taagtttatt   2520
gtttatcgtg aaagtagtgt caatactact ttgacattaa ctaatttcac gtttagtaat   2580
gaaagtggtg cccctcctaa tacaggtggt gttgacagtt ttattttata ccagacacaa   2640
acagctcaga gtggttatta taattttaat ttttcatttc tgagtagttt tgtttatagg   2700
gaaagtaatt atatgtatgg atcttaccat ccacgttgta gttttagacc tgaaaccctt   2760
```

```
aatggtttgt ggtttaattc cctttctgtt tcattaacat acggtcccat tcaaggtggt   2820
tgtaagcaat ctgtatttaa tggtaaagca acttgttgtt atgcttattc atacggagga   2880
cctcgtgctt gtaaaggtgt ctatagaggt gagctaacac agcattttga atgtggtttg   2940
ttagtttatg ttactaagag cgatggctcc cgtatacaaa ctgcaacaca accacctgta   3000
ttaacccaaa atttttataa taacatcact ttaggtaagt gtgttgatta taatgtttat   3060
ggtagaactg gacaaggttt tattactaat gtaactgatt tagctacttc tcataattac   3120
ttagcggatg gaggattagc tattttagat acatctggtg ccatagacat cttcgttgta   3180
caaggtgaat atggccctaa ctactataag gttaatctat gtgaagatgt taaccaacag   3240
tttgtagttt ctggtggtaa attagtaggt attctcactt cacgtaatga aactggttct   3300
cagcctcttg aaaaccagtt ttacattaag atcactaatg gaacacatcg ttctagacgt   3360
tctgttaatg aaaatgttac gaattgccct tatgttagtt atggcaagtt ttgtataaaa   3420
cctgatggtt cagtttctcc tatagtacca aaagaacttg aacagtttgt ggcaccttta   3480
cttaatgtta ctgaaaatgt gctcatacct aacagtttta acttaactgt tacagatgag   3540
tacatacaaa cgcatatgga taagatccaa attaattgtc tgcagtatgt ttgtggcaac   3600
tctttggctt gtagaaagct gtttcaacaa tatgggcctg tttgtgacaa catattgtct   3660
gtagtaaata gtgttggtca aaaagaagat atggaacttt taagcttcta ttcttctact   3720
aaaccatctg gttttaatac accagttttt agtaatctta gcactggtga gtttaatatc   3780
tctcttttgt taacaacccc tagtagtcct agagggcgtt cttttattga agatctttta   3840
tttacaagtg ttgaatctgt tggattacca acagatgaag cttataaaaa gtgcactgca   3900
ggacctttag gctttcttaa agaccttgca tgtgctcgtg aatataatgg tttgcttgtg   3960
ttgcctccta ttataacagc agaaatgcaa actttgtata ctagttctct agtagtttct   4020
atggcttttg gtggtattac ttcagctggt gctatacctt ttgccacaca actgcaggct   4080
agaattaatc acttgggtat tacccagtca cttttgttga agaatcaaga aaaaattgct   4140
gcttccttta ataaggccat tggtcatatg caggaaggtt ttaggagtac atctctagca   4200
ttacaacaaa ttcaagatgt tgttaataag cagagtgcta ttcttactga gactatgtta   4260
gcacttaata aaaattttgg tgctatttct tctgtgattc aagacattta ccagcaactt   4320
gatgacatac aagcagatgc tcaagtggat cgactcataa ctggtagatt gtcatcactt   4380
tctgtcttag catctgctaa gcagtcggag tacattagag tgtcacaaca gcgtgagtta   4440
gctactcaga aaattaatga gtgtgttaaa tcacagtcta ttaggtattc cttttgtggt   4500
aatggacgac atgttttaac cataccacaa aatgccccta atggtatagt gtttatacac   4560
tttacttata caccagagag ctttattaat gttactgcag tagtaggttt ttgtgtaagt   4620
cctgctaatg ctagtcagta tgcaatagtg cccgctaatg gtaggggtat ttttatacaa   4680
gttaatggta gttactacat cactgcacgt gatatgtata tgccaagaga tattactgca   4740
ggagatatag ttacgcttac ttcttgtcaa gcaaattatg taagtgtaaa caagaccgtc   4800
attactacat ttgtagacaa tgatgatttt gattttgatg acgagttatc aaaatggtgg   4860
aatgaaacta agcacgagtt gccagacttt gaccagttta attacaccat tcccgtttta   4920
aatataactt atgatattga caagattgag gaagttatta agggacttaa tgattccttg   4980
attgacctcg aaacattgtc aattctcaaa acttatatta agtggccggg aggaggtcat   5040
catcaccatc accactaagc ggccgcactc ctcaggtgca ggctgcctat cagaaggtgg   5100
tggctggtgt ggccaatgcc ctggctcaca aataccactg agatcttttt ccctctgcca   5160
```

-continued

```
aaaattatgg ggacatcatg aagccccttg agcatctgac ttctggctaa taaaggaaat   5220
ttattttcat tgcaatagtg tgttggaatt ttttgtgtct ctcactcgga aggacatatg   5280
ggagggcaaa tcatttaaaa catcagaatg agtatttggt ttagagtttg gcaacatatg   5340
cccatatgct ggctgccatg aacaaaggtg gctataaaga ggtcatcagt atatgaaaca   5400
gccccctgct gtccattcct tattccatag aaaagccttg acttgaggtt agattttttt   5460
tatattttgt tttgtgttat ttttttcttt aacatcccta aaattttcct tacatgtttt   5520
actagccaga tttttcctcc tctcctgact actcccagtc atagctgtcc ctcttctctt   5580
atgaagatcc ctcgacctgc agcccaagct tggcgtaatc atggtcatag ctgtttcctg   5640
tgtgaaattg ttatccgctc acaattccac acaacatacg agccggaagc ataaagtgta   5700
aagcctgggg tgcctaatga gtgagctaac tcacattaat tgcgttgcgc tcactgcccg   5760
ctttccagtc gggaaacctg tcgtgccagc ggatccgcat ctcaattagt cagcaaccat   5820
agtcccgccc ctaactccgc ccatcccgcc cctaactccg cccagttccg cccattctcc   5880
gccccatggc tgactaattt tttttattta tgcagaggcc gaggccgcct cggcctctga   5940
gctattccag aagtagtgag gaggcttttt tggaggccta ggcttttgca aaaagctaac   6000
ttgtttattg cagcttataa tggttacaaa taaagcaata gcatcacaaa tttcacaaat   6060
aaagcatttt tttcactgca ttctagttgt ggtttgtcca aactcatcaa tgtatcttat   6120
catgtctgga tccgctgcat taatgaatcg gccaacgcgc ggggagaggc ggtttgcgta   6180
ttgggcgctc ttccgcttcc tcgctcactg actcgctgcg ctcggtcgtt cggctgcggc   6240
gagcggtatc agctcactca aaggcggtaa tacggttatc cacagaatca ggggataacg   6300
caggaaagaa catgtgagca aaaggccagc aaaaggccag gaaccgtaaa aaggccgcgt   6360
tgctggcgtt tttccatagg ctccgccccc ctgacgagca tcacaaaaat cgacgctcaa   6420
gtcagaggtg gcgaaacccg acaggactat aaagatacca ggcgtttccc cctggaagct   6480
ccctcgtgcg ctctcctgtt ccgaccctgc cgcttaccgg atacctgtcc gcctttctcc   6540
cttcgggaag cgtggcgctt tctcaatgct cacgctgtag gtatctcagt tcggtgtagg   6600
tcgttcgctc caagctgggc tgtgtgcacg aaccccccgt tcagcccgac cgctgcgcct   6660
tatccggtaa ctatcgtctt gagtccaacc cggtaagaca cgacttatcg ccactggcag   6720
cagccactgg taacaggatt agcagagcga ggtatgtagg cggtgctaca gagttcttga   6780
agtggtggcc taactacggc tacactagaa ggacagtatt tggtatctgc gctctgctga   6840
agccagttac cttcggaaaa agagttggta gctcttgatc cggcaaacaa accaccgctg   6900
gtagcggtgg tttttttgtt tgcaagcagc agattacgcg cagaaaaaaa ggatctcaag   6960
aagatccttt gatcttttct acggggtctg acgctcagtg gaacgaaaac tcacgttaag   7020
ggattttggt catgagatta tcaaaaagga tcttcaccta gatcctttta aattaaaaat   7080
gaagttttaa atcaatctaa agtatatatg agtaaacttg gtctgacagt taccaatgct   7140
taatcagtga ggcacctatc tcagcgatct gtctatttcg ttcatccata gttgcctgac   7200
tccccgtcgt gtagataact acgatacggg agggcttacc atctggcccc agtgctgcaa   7260
tgataccgcg agacccacgc tcaccggctc cagatttatc agcaataaac cagccagccg   7320
gaagggccga gcgcagaagt ggtcctgcaa ctttatccgc ctccatccag tctattaatt   7380
gttgccggga agctagagta agtagttcgc cagttaatag tttgcgcaac gttgttgcca   7440
ttgctacagg catcgtggtg tcacgctcgt cgtttggtat ggcttcattc agctccggtt   7500
```

cccaacgatc aaggcgagtt acatgatccc ccatgttgtg caaaaaagcg gttagctcct 7560
tcggtcctcc gatcgttgtc agaagtaagt tggccgcagt gttatcactc atggttatgg 7620
cagcactgca taattctctt actgtcatgc catccgtaag atgcttttct gtgactggtg 7680
agtactcaac caagtcattc tgagaatagt gtatgcggcg accgagttgc tcttgcccgg 7740
cgtcaatacg ggataatacc gcgccacata gcagaacttt aaaagtgctc atcattggaa 7800
aacgttcttc ggggcgaaaa ctctcaagga tcttaccgct gttgagatcc agttcgatgt 7860
aacccactcg tgcacccaac tgatcttcag catcttttac tttcaccagc gtttctgggt 7920
gagcaaaaac aggaaggcaa aatgccgcaa aaaagggaat aagggcgaca cggaaatgtt 7980
gaatactcat actcttcctt tttcaatatt attgaagcat ttatcagggt tattgtctca 8040
tgagcggata catatttgaa tgtatttaga aaaataaaca aataggggtt ccgcgcacat 8100
ttccccgaaa agtgccacct g 8121

<210> SEQ ID NO 3
<211> LENGTH: 5471
<212> TYPE: DNA
<213> ORGANISM: Artificial Sequence
<220> FEATURE:
<223> OTHER INFORMATION: synthetic

<400> SEQUENCE: 3
accatgagcg ataacggacc ccagaaccaa cgtaacgccc ctcgcattac ttttggcggg 60
ccttccgact ctacaggttc taatcaaaac ggggagcgaa gcggggcacg cagcaagcaa 120
cgcaggcctc aaggtctgcc aaacaacact gcttcttggt tcactgctct cactcaacat 180
ggcaaagagg atctgaaatt cccccgagga caaggggtac cgatcaatac taactcctct 240
cccgatgatc aaattggata ctacaggcgc gccacccgga gaattcgcgg cggagacggg 300
aaaatgaagg accttagtcc aagatggtac ttttattact tggggaccgg accggaagct 360
ggcttgccct atggtgccaa taaggacgga attatttggg tggcgacaga gggcgctctg 420
aatactccca aggaccacat aggtactcgg aatcctgcta ataatgccgc catcgtgttg 480
cagctccccc aaggcaccac cctacccaag ggcttttatg ccgaggggtc ccgcggcggg 540
agccaggctt catccaggag ttctagtcgc tctcgcaact catcccgcaa ctccacccct 600
ggctctagta ggggtactag tcccgcccga atggccggca atggcggaga cgctgcccta 660
gcgctgttgt tgctggatag actcaatcag ctcgaaagta agatgtccgg caaaggacaa 720
cagcagcaag gacaaacggt taccaagaaa agcgcagcag aggcaagtaa gaaacccagg 780
caaaagcgca ctgccaccaa agcttacaac gtgacacagg cctttggtcg cagaggaccc 840
gaacaaacac aaggcaattt tggagatcag gaacttataa ggcaaggaac agactataag 900
cattggcccc aaattgcaca atttgcccca tccgcttctg cattcttcgg tatgagtagg 960
attggaatgg aagttacacc cagtggcacc tggctcacat atacaggcgc tatcaagctt 1020
gatgataagg atccgaattt taaggaccag gtgatcctgt tgaacaaaca tatagacgct 1080
tataaaacct ttcccccgac tgaacctaag aaagacaaga agaagaaagc tgatgaaact 1140
caagcgctgc cgcaaagaca aaagaaacaa caaaccgtta cgctcctgcc agcagctgac 1200
ctggacgatt ttagtaaaca actccaacaa agcatgtcta gcgccgatag tactcaggct 1260
ggcggcgggc accaccatca tcatcactga gctagcttga ctgactgaga tacagcgtac 1320
cttcagctca cagacatgat aagatacatt gatgagtttg gacaaaccac aactagaatg 1380
cagtgaaaaa aatgctttat ttgtgaaatt tgtgatgcta ttgctttatt tgtaaccatt 1440
ataagctgca ataaacaagt taacaacaac aattgcattc attttatgtt tcaggttcag 1500
ggggaggtgt gggaggtttt ttaaagcaag taaaacctct acaaatgtgg tattggccca 1560
tctctatcgg tatcgtagca taacccttg ggcctctaa acgggtcttg aggggttttt 1620
tgtgcccctc gggccggatt gctatctacc ggcattggcg cagaaaaaaa tgcctgatgc 1680
gacgctgcgc gtcttatact cccacatatg ccagattcag caacggatac ggcttcccca 1740
acttgcccac ttccatacgt gtcctcctta ccagaaattt atccttaagg tcgtcagcta 1800
tcctgcaggc gatctctcga tttcgatcaa gacattcctt taatggtctt ttctggacac 1860
cactaggggt cagaagtagt tcatcaaact ttcttccctc cctaatctca ttggttacct 1920
tgggctatcg aaacttaatt aaccagtcaa gtcagctact tggcgagatc gacttgtctg 1980
ggtttcgact acgctcagaa ttgcgtcagt caagttcgat ctggtccttg ctattgcacc 2040
cgttctccga ttacgagttt catttaaatc atgtgagcaa aaggccagca aaaggccagg 2100
aaccgtaaaa aggccgcgtt gctggcgttt ttccataggc tccgcccccc tgacgagcat 2160
cacaaaaatc gacgctcaag tcagaggtgg cgaaacccga caggactata aagataccag 2220
gcgtttcccc ctggaagctc cctcgtgcgc tctcctgttc cgaccctgcc gcttaccgga 2280
tacctgtccg cctttctccc ttcgggaagc gtggcgcttt ctcatagctc acgctgtagg 2340
tatctcagtt cggtgtaggt cgttcgctcc aagctgggct gtgtgcacga accccccgtt 2400
cagcccgacc gctgcgcctt atccggtaac tatcgtcttg agtccaaccc ggtaagacac 2460
gacttatcgc cactggcagc agccactggt aacaggatta gcagagcgag gtatgtaggc 2520
ggtgctacag agttcttgaa gtggtggcct aactacggct acactagaag aacagtattt 2580
ggtatctgcg ctctgctgaa gccagttacc ttcggaaaaa gagttggtag ctcttgatcc 2640
ggcaaacaaa ccaccgctgg tagcggtggt ttttttgttt gcaagcagca gattacgcgc 2700
agaaaaaaag gatctcaaga agatcctttg atcttttcta cggggtctga cgctcagtgg 2760
aacgaaaact cacgttaagg gattttggtc atgagattat caaaaaggat cttcacctag 2820
atccttttaa attaaaaatg aagttttaaa tcaatctaaa gtatatatga gtaaacttgg 2880
tctgacagtt accaatgctt aatcagtgag gcacctatct cagcgatctg tctatttcgt 2940
tcatccatag ttgcatttaa atttccgaac tctccaaggc cctcgtcgga aaatcttcaa 3000
acctttcgtc cgatccatct tgcaggctac ctctcgaacg aactatcgca agtctcttgg 3060
ccggccttgc gccttggcta ttgcttggca gcgcctatcg ccaggtatta ctccaatccc 3120
gaatatccga gatcgggatc acccgagaga agttcaacct acatcctcaa tcccgatcta 3180
tccgagatcc gaggaatatc gaaatcgggg cgcgcctggt gtaccgagaa cgatcctctc 3240
agtgcgagtc tcgacgatcc atatcgttgc ttggcagtca gccagtcgga atccagcttg 3300
ggacccagga agtccaatcg tcagatattg tactcaagcc tggtcacggc agcgtaccga 3360
tctgtttaaa cctagatatt gatagtctga tcggtcaacg tataatcgag tcctagcttt 3420
tgcaaacatc tatcaagaga caggatcagc aggaggcttt cgcatgagta ttcaacattt 3480
ccgtgtcgcc cttattccct tttttgcggc attttgcctt cctgtttttg ctcacccaga 3540
aacgctggtg aaagtaaaag atgctgaaga tcagttgggt gcgcgagtgg gttacatcga 3600
actggatctc aacagcggta agatccttga gagttttcgc cccgaagaac gctttccaat 3660
gatgagcact tttaaagttc tgctatgtgg cgcggtatta tcccgtattg acgccgggca 3720
agagcaactc ggtcgccgca tacactattc tcagaatgac ttggttgagt attcaccagt 3780
cacagaaaag catcttacgg atggcatgac agtaagagaa ttatgcagtg ctgccataac 3840
catgagtgat aacactgcgg ccaacttact tctgacaacg attggaggac cgaaggagct 3900
aaccgctttt ttgcacaaca tgggggatca tgtaactcgc cttgatcgtt gggaaccgga 3960
gctgaatgaa gccataccaa acgacgagcg tgacaccacg atgcctgtag caatggcaac 4020
aaccttgcgt aaactattaa ctggcgaact acttactcta gcttcccggc aacagttgat 4080
agactggatg gaggcggata aagttgcagg accacttctg cgctcggccc ttccggctgg 4140
ctggtttatt gctgataaat ctggagccgg tgagcgtggg tctcgcggta tcattgcagc 4200
actggggcca gatggtaagc cctcccgtat cgtagttatc tacacgacgg ggagtcaggc 4260
aactatggat gaacgaaata gacagatcgc tgagataggt gcctcactga ttaagcattg 4320
gtaaccgatt ctaggtgcat tggcgcagaa aaaaatgcct gatgcgacgc tgcgcgtctt 4380
atactcccac atatgccaga ttcagcaacg gatacggctt ccccaacttg cccacttcca 4440
tacgtgtcct ccttaccaga aatttatcct taagatcccg aatcgtttaa actcgactct 4500
ggctctatcg aatctccgtc gtttcgagct tacgcgaaca gccgtggcgc tcatttgctc 4560
gtcgggcatc gaatctcgtc agctatcgtc agcttacctt tttggcagcg atcgcggctc 4620
ccgacatctt ggaccattag ctccacaggt atcttcttcc ctctagtggt cataacagca 4680
gcttcagcta cctctcaatt caaaaaaccc ctcaagaccc gtttagaggc cccaaggggt 4740
tatgctatca atcgttgcgt tacacacaca aaaaaccaac acacatccat cttcgatgga 4800
tagcgatttt attatctaac tgctgatcga gtgtagccag atctagtaat caattacggg 4860
gtcattagtt catagcccat atatggagtt ccgcgttaca taacttacgg taaatggccc 4920
gcctggctga ccgcccaacg acccccgccc attgacgtca ataatgacgt atgttcccat 4980
agtaacgcca atagggactt tccattgacg tcaatgggtg gagtatttac ggtaaactgc 5040
ccacttggca gtacatcaag tgtatcatat gccaagtacg ccccctattg acgtcaatga 5100
cggtaaatgg cccgcctggc attatgccca gtacatgacc ttatgggact ttcctacttg 5160
gcagtacatc tacgtattag tcatcgctat taccatgctg atgcggtttt ggcagtacat 5220
caatgggcgt ggatagcggt ttgactcacg gggatttcca agtctccacc ccattgacgt 5280
caatgggagt ttgttttggc accaaaatca acgggacttt ccaaaatgtc gtaacaactc 5340
cgccccattg acgcaaatgg gcggtaggcg tgtacggtgg gaggtctata taagcagagc 5400
tggtttagtg aaccgtcaga tcagatcttt gtcgatccta ccatccactc gacacacccg 5460
ccagcggccg c 5471

<210> SEQ ID NO 4
<211> LENGTH: 7850
<212> TYPE: DNA
<213> ORGANISM: Artificial Sequence
<220> FEATURE:
<223> OTHER INFORMATION: synthetic

<400> SEQUENCE: 4
accatgtttg tgttcctggt actcctaccg ctggtgagct cccaatgcgt caatctcacg 60
actaggacac aactcccacc cgcctacacg aactctttta caaggggtgt atactaccct 120
gacaaggtgt tccgcagcag cgtgctacat agcactcaag atttgtttct gcccttcttc 180
tctaacgtaa catggttcca tgcgatacat gtatctggta ccaatggaac aaaacggttt 240
gataacccag ttctcccgtt taatgatgga gtttactttg catccactga aaagtctaat 300
ataatacgcg gatggatttt cggcacaaca ctggatagta agacccagag tctgcttatt 360

-continued

```
gtcaataacg ccactaacgt ggtgattaag gtgtgtgagt ttcaattctg taatgaccca    420
tttctcgggg tttactacca taagaacaat aagagctgga tggaatcaga atttagagtt    480
tatagcagcg caaacaattg cacatttgaa tacgtttctc aaccctttct gatggatctc    540
gaaggaaaac aagggaactt taagaacctc agggaatttg tcttcaagaa catagatggg    600
tacttcaaaa tttacagcaa gcatacacca attaacttgg ttagagacct gccccaggga    660
ttttctgcac ttgaaccctt ggttgacttg cctatcggca ttaatattac tcgatttcaa    720
actctgctcg ctttgcaccg cagctacctg acaccgggag actcctctag tggctggacc    780
gcaggagcag ctgcatatta tgtgggttat ctccaaccca gaacatttct gctaaagtac    840
aacgaaaatg ggacaatcac cgatgcggtc gactgcgcat tggatcccct atccgagact    900
aagtgtactt tgaagagctt taccgtggaa aaggggatct atcaaacttc caactttcgg    960
gtgcaaccga ccgaaagcat cgttagattt cccaatatca ccaacttgtg tccctttggc   1020
gaagttttca acgctactcg ctttgcaagt gtctatgctt ggaatagaaa gaggataagc   1080
aactgcgtcg ctgactattc tgttctgtat aactctgcga gcttttcaac tttcaaatgc   1140
tatggggtct ccccaaccaa gcttaatgac ttgtgcttca ctaacgttta tgcagatagc   1200
ttcgtcatac ggggcgatga agtgcggcaa atcgcgccag gacaaacagg taagatcgcc   1260
gactacaact ataaactgcc agacgatttt acaggctgcg tgatcgcttg gaactctaac   1320
aatcttgatt ctaaagttgg tgggaattat aactatctat atcgtctctt cagaaaatct   1380
aacctcaagc cctttgagcg ggatataagc acagaaatct atcaggctgg gtctactcct   1440
tgcaatggtg tcgaaggttt caattgctac tttccactgc aatcctacgg ctttcaacct   1500
acaaatggtg tcggttatca accgtataga gttgttgtgc tctcctttga gttgctacac   1560
gctcctgcca cggtttgtgg acccaagaag tcaacgaatc tggtgaagaa taaatgcgtc   1620
aattttaatt ttaacggact tacggggact ggcgttctca ccgaatccaa taagaagttc   1680
cttccattcc agcaatttgg ccgcgatatc gccgatacaa cagacgctgt cagagatcca   1740
caaaccttgg agatcttgga tattacacca tgctctttcg gcggggtatc agtaatcacg   1800
ccggggacaa atacatccaa tcaggttgcc gtattgtatc aggatgtgaa ctgcaccgag   1860
gtccctgttg ccatacatgc cgatcagttg actccgactt ggcgggtgta ttctacaggg   1920
tctaatgtat ttcaaaccag agcaggatgc ctcatcggtg ccgaacatgt taataattca   1980
tatgagtgtg atatccccat aggagcaggc atttgtgcat cctaccaaac tcagaccaac   2040
tcaccaagac gggcccggtc tgtggcgtcc cagtccataa ttgcctacac aatgagtctt   2100
ggagccgaaa actcagttgc ctattccaac aactccatcg ctatccccac gaattttaca   2160
atctcagtta ccactgaaat cctgcccgta tctatgacaa agacaagtgt tgattgcaca   2220
atgtatatct gcggggactc tactgagtgc tcaaatctgc tgctacagta cggtagcttt   2280
tgtactcagc taaatcgcgc actcaccggg attgctgtag aacaagacaa gaatacacaa   2340
gaggttttcg cccaagtgaa acaaatatac aaaacgcccc ctataaaaga cttcggtggt   2400
tttaacttta gccagatttt gccggatcca tccaaaccat ctaagcgctc tttcattgaa   2460
gatctcctgt tcaacaaagt tacattggcg gacgcaggtt tcattaagca atatggggat   2520
tgccttgggg atatcgcagc gcgggatctg atttgtgccc agaagttcaa tggtctgacg   2580
gttctgccac ccctactcac cgatgaaatg atcgcgcaat ataccagcgc tcttctggca   2640
ggtaccatca cttccggctg gaccttcgga gccggcgccg cacttcaaat ccctttcgcc   2700
```

-continued

```
atgcaaatgg catatagatt taatggcatc ggtgtcaccc aaaacgtatt gtatgagaac   2760
caaaagctga ttgccaatca atttaatagc gcaattggta aaatacaaga cagcctgagc   2820
agtacggcaa gcgcactcgg gaagcttcaa gatgtagtta atcagaatgc tcaggctttg   2880
aatactcttg tgaaacaact ctcttccaat tttggcgcca tctcatctgt gctcaacgac   2940
attctttccc gactcgataa ggtggaagct gaagttcaaa tcgatcggct cattacaggc   3000
agactgcagt ctctccaaac ctacgtcacc cagcaactga ttagggcggc agaaattcgc   3060
gcttctgcaa atcttgcagc cacaaagatg agcgagtgtg tcctgggcca atcaaagcgc   3120
gtcgactttt gcggaaaggg gtatcatctc atgagctttc cacaatcagc cccacatgga   3180
gttgtctttc tccatgtaac gtacgtccct gctcaggaaa agaatttcac cacagcccca   3240
gctatttgcc atgacggaaa ggctcacttc ccacgtgaag gcgtatttgt atcaaatggc   3300
acccactggt tcgtcaccca acgtaacttt tacgagcctc agattatcac cacggataac   3360
acgttcgtca gcgggaattg tgatgtagtc attggtattg tcaataatac cgtgtatgat   3420
ccccttcaac ccgaattgga ctcctttaaa gaagaactcg acaaatactt taagaaccat   3480
acgtcccctg acgtggacct cggtgacatt tcaggcataa atgcctcagt ggtgaacatt   3540
caaaaggaaa tcgataggct gaacgaagtg gccaagaatt tgaacgaaag tttgattgat   3600
ctccaagaac tggggaaata cgaacaatat ataaaatggg gtggcggaca ccatcatcat   3660
caccattaag ctagcttgac tgactgagat acagcgtacc ttcagctcac agacatgata   3720
agatacattg atgagtttgg acaaaccaca actagaatgc agtgaaaaaa atgctttatt   3780
tgtgaaattt gtgatgctat tgctttattt gtaaccatta taagctgcaa taaacaagtt   3840
aacaacaaca attgcattca ttttatgttt caggttcagg gggaggtgtg ggaggttttt   3900
taaagcaagt aaaacctcta caaatgtggt attggcccat ctctatcggt atcgtagcat   3960
aaccccttgg ggcctctaaa cgggtcttga ggggtttttt gtgcccctcg ggccggattg   4020
ctatctaccg gcattggcgc agaaaaaaat gcctgatgcg acgctgcgcg tcttatactc   4080
ccacatatgc cagattcagc aacggatacg gcttccccaa cttgcccact tccatacgtg   4140
tcctccttac cagaaattta tccttaaggt cgtcagctat cctgcaggcg atctctcgat   4200
ttcgatcaag acattccttt aatggtcttt tctggacacc actaggggtc agaagtagtt   4260
catcaaactt tcttccctcc ctaatctcat tggttacctt gggctatcga aacttaatta   4320
accagtcaag tcagctactt ggcgagatcg acttgtctgg gtttcgacta cgctcagaat   4380
tgcgtcagtc aagttcgatc tggtccttgc tattgcaccc gttctccgat tacgagtttc   4440
atttaaatca tgtgagcaaa aggccagcaa aaggccagga accgtaaaaa ggccgcgttg   4500
ctggcgtttt tccataggct ccgcccccct gacgagcatc acaaaaatcg acgctcaagt   4560
cagaggtggc gaaacccgac aggactataa agataccagg cgtttccccc tggaagctcc   4620
ctcgtgcgct ctcctgttcc gaccctgccg cttaccggat acctgtccgc ctttctccct   4680
tcgggaagcg tggcgctttc tcatagctca cgctgtaggt atctcagttc ggtgtaggtc   4740
gttcgctcca agctgggctg tgtgcacgaa ccccccgttc agcccgaccg ctgcgcctta   4800
tccggtaact atcgtcttga gtccaacccg gtaagacacg acttatcgcc actggcagca   4860
gccactggta acaggattag cagagcgagg tatgtaggcg gtgctacaga gttcttgaag   4920
tggtggccta actacggcta cactagaaga acagtatttg gtatctgcgc tctgctgaag   4980
ccagttacct tcggaaaaag agttggtagc tcttgatccg gcaaacaaac caccgctggt   5040
agcggtggtt tttttgtttg caagcagcag attacgcgca gaaaaaaagg atctcaagaa   5100
```

-continued

```
gatcctttga tcttttctac ggggtctgac gctcagtgga acgaaaactc acgttaaggg   5160
attttggtca tgagattatc aaaaaggatc ttcacctaga tccttttaaa ttaaaaatga   5220
agttttaaat caatctaaag tatatatgag taaacttggt ctgacagtta ccaatgctta   5280
atcagtgagg cacctatctc agcgatctgt ctatttcgtt catccatagt tgcatttaaa   5340
tttccgaact ctccaaggcc ctcgtcggaa aatcttcaaa cctttcgtcc gatccatctt   5400
gcaggctacc tctcgaacga actatcgcaa gtctcttggc cggccttgcg ccttggctat   5460
tgcttggcag cgcctatcgc caggtattac tccaatcccg aatatccgag atcgggatca   5520
cccgagagaa gttcaaccta catcctcaat cccgatctat ccgagatccg aggaatatcg   5580
aaatcggggc gcgcctggtg taccgagaac gatcctctca gtgcgagtct cgacgatcca   5640
tatcgttgct tggcagtcag ccagtcggaa tccagcttgg gacccaggaa gtccaatcgt   5700
cagatattgt actcaagcct ggtcacggca gcgtaccgat ctgtttaaac ctagatattg   5760
atagtctgat cggtcaacgt ataatcgagt cctagctttt gcaaacatct atcaagagac   5820
aggatcagca ggaggctttc gcatgagtat tcaacatttc cgtgtcgccc ttattccctt   5880
ttttgcggca ttttgccttc ctgtttttgc tcacccagaa acgctggtga aagtaaaaga   5940
tgctgaagat cagttgggtg cgcgagtggg ttacatcgaa ctggatctca acagcggtaa   6000
gatccttgag agttttcgcc ccgaagaacg ttttccaatg atgagcactt ttaaagttct   6060
gctatgtggc gcggtattat cccgtattga cgccgggcaa gagcaactcg gtcgccgcat   6120
acactattct cagaatgact tggttgagta ttcaccagtc acagaaaagc atcttacgga   6180
tggcatgaca gtaagagaat tatgcagtgc tgccataacc atgagtgata acactgcggc   6240
caacttactt ctgacaacga ttggaggacc gaaggagcta accgcttttt tgcacaacat   6300
gggggatcat gtaactcgcc ttgatcgttg ggaaccggag ctgaatgaag ccataccaaa   6360
cgacgagcgt gacaccacga tgcctgtagc aatggcaaca accttgcgta aactattaac   6420
tggcgaacta cttactctag cttcccggca acagttgata gactggatgg aggcggataa   6480
agttgcagga ccacttctgc gctcggccct tccggctggc tggtttattg ctgataaatc   6540
tggagccggt gagcgtgggt ctcgcggtat cattgcagca ctggggccag atggtaagcc   6600
ctcccgtatc gtagttatct acacgacggg gagtcaggca actatggatg aacgaaatag   6660
acagatcgct gagataggtg cctcactgat taagcattgg taaccgattc taggtgcatt   6720
ggcgcagaaa aaaatgcctg atgcgacgct gcgcgtctta tactcccaca tatgccagat   6780
tcagcaacgg atacggcttc cccaacttgc ccacttccat acgtgtcctc cttaccagaa   6840
atttatcctt aagatcccga atcgtttaaa ctcgactctg gctctatcga atctccgtcg   6900
tttcgagctt acgcgaacag ccgtggcgct catttgctcg tcgggcatcg aatctcgtca   6960
gctatcgtca gcttaccttt ttggcagcga tcgcggctcc cgacatcttg gaccattagc   7020
tccacaggta tcttcttccc tctagtggtc ataacagcag cttcagctac ctctcaattc   7080
aaaaaacccc tcaagacccg tttagaggcc ccaaggggtt atgctatcaa tcgttgcgtt   7140
acacacacaa aaaaccaaca cacatccatc ttcgatggat agcgatttta ttatctaact   7200
gctgatcgag tgtagccaga tctagtaatc aattacgggg tcattagttc atagcccata   7260
tatggagttc cgcgttacat aacttacggt aaatggcccg cctggctgac cgcccaacga   7320
cccccgccca ttgacgtcaa taatgacgta tgttcccata gtaacgccaa tagggacttt   7380
ccattgacgt caatgggtgg agtatttacg gtaaactgcc cacttggcag tacatcaagt   7440
```

-continued

```
gtatcatatg ccaagtacgc cccctattga cgtcaatgac ggtaaatggc ccgcctggca   7500

ttatgcccag tacatgacct tatgggactt tcctacttgg cagtacatct acgtattagt   7560

catcgctatt accatgctga tgcggttttg gcagtacatc aatgggcgtg gatagcggtt   7620

tgactcacgg ggatttccaa gtctccaccc cattgacgtc aatgggagtt tgttttggca   7680

ccaaaatcaa cgggactttc caaaatgtcg taacaactcc gccccattga cgcaaatggg   7740

cggtaggcgt gtacggtggg aggtctatat aagcagagct ggtttagtga accgtcagat   7800

cagatctttg tcgatcctac catccactcg acacacccgc cagcggccgc              7850


<210> SEQ ID NO 5
<211> LENGTH: 412
<212> TYPE: PRT
<213> ORGANISM: Infectious Bronchitis Virus

<400> SEQUENCE: 5

Met Ala Ser Gly Lys Ala Thr Gly Lys Thr Asp Ala Pro Ala Pro Val
1               5                   10                  15

Ile Lys Leu Gly Gly Pro Lys Pro Pro Lys Val Gly Ser Ser Gly Asn
            20                  25                  30

Ala Ser Trp Phe Gln Ala Ile Lys Ala Lys Lys Leu Asn Ser His Pro
        35                  40                  45

Pro Lys Phe Glu Gly Ser Gly Val Pro Asp Asn Glu Asn Leu Lys Thr
    50                  55                  60

Ser Gln Gln His Gly Tyr Trp Arg Arg Gln Ala Arg Phe Lys Pro Val
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Ser Gln Asp Gly
            100                 105                 110

Ile Val Trp Val Ala Ala Lys Gly Ala Asp Val Lys Ser Arg Ser His
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Leu
145                 150                 155                 160

Asn Arg Gly Arg Ser Gly Arg Ser Thr Ala Ala Ser Ser Ala Ala Ser
                165                 170                 175

Ser Arg Ala Pro Ser Arg Asp Gly Ser Arg Gly Arg Arg Ser Gly Ser
            180                 185                 190

Glu Asp Asp Leu Ile Ala Arg Ala Ala Lys Ile Ile Gln Asp Gln Gln
        195                 200                 205

Lys Lys Gly Ser Arg Ile Thr Lys Val Lys Ala Asp Glu Met Ala His
    210                 215                 220

Arg Arg Tyr Cys Lys Arg Thr Ile Pro Pro Gly Tyr Lys Val Asp Gln
225                 230                 235                 240

Val Phe Gly Pro Arg Thr Lys Gly Lys Glu Gly Asn Phe Gly Asp Asp
                245                 250                 255

Lys Met Asn Glu Glu Gly Ile Lys Asp Gly Arg Val Thr Ala Met Leu
            260                 265                 270

Asn Leu Val Pro Ser Ser His Ala Cys Leu Phe Gly Ser Arg Val Thr
        275                 280                 285

Pro Lys Leu Gln Pro Asp Gly Leu His Leu Lys Phe Glu Phe Thr Thr
    290                 295                 300
```

-continued

Val Val Pro Arg Asp Asp Pro Gln Phe Asp Asn Tyr Val Lys Ile Cys
305 310 315 320

Asp Gln Cys Val Asp Gly Val Gly Thr Arg Pro Lys Asp Asp Glu Pro
325 330 335

Arg Pro Lys Ser Arg Ser Ser Ser Arg Pro Ala Thr Arg Thr Ser Ser
340 345 350

Pro Ala Pro Arg Gln Gln Arg Pro Lys Lys Glu Lys Lys Pro Lys Lys
355 360 365

Gln Asp Asp Glu Val Asp Lys Ala Leu Thr Ser Asn Glu Glu Arg Asn
370 375 380

Asn Ala Gln Leu Glu Phe Asp Glu Glu Pro Lys Val Ile Asn Trp Gly
385 390 395 400

Asp Ala Ala Leu Gly Glu Asn Glu Leu Gly Gly Gly
405 410

<210> SEQ ID NO 6
<211> LENGTH: 1257
<212> TYPE: DNA
<213> ORGANISM: Artificial Sequence
<220> FEATURE:
<223> OTHER INFORMATION: synthetic

<400> SEQUENCE: 6
atggcaagcg gtaaagcaac tggaaagaca gacgccccag cgccagtcat caaactagga 60
ggaccaaagc cacctaaagt tggttcttct ggaaatgcat cttggtttca agcaataaaa 120
gccaagaagc taaattcaca tccacctaag tttgaaggta gcggtgttcc tgataatgaa 180
aatcttaaaa caagtcagca acatggatac tggaggcgcc aagccaggtt taagccagtt 240
aaaggcggaa gaaaaccagt cccagatgct tggtacttct attatactgg aacaggacca 300
gccgctgacc tgaattgggg tgatagccaa gatggtatag tgtgggttgc tgcaaagggt 360
gctgatgtta aatctagatc tcaccagggt acaagggacc ctgacaagtt tgaccaatat 420
ccactacgat tctcggacgg aggacctgat ggtaatttcc gttgggactt cattcctctg 480
aatcgtggta ggagtggaag atcaacagca gcttcatcag cagcatctag tagagcaccg 540
tcgcgtgacg gctcgcgtgg tcgtagaagt ggttctgaag atgatcttat tgctcgtgca 600
gcaaagataa tccaggatca gcagaagaag ggttctcgca ttactaaggt taaggctgat 660
gaaatggctc accgccggta ttgcaagcgc actattccac ctggttataa ggttgatcaa 720
gtctttggcc cccgtactaa aggtaaggag ggaaattttg gtgatgacaa gatgaatgag 780
gaaggtatta aggatgggcg tgttacagca atgctcaacc tagtccctag cagccatgct 840
tgtctttttg gaagtagagt gacgcccaaa ctacaaccag atgggctgca cttgaaattt 900
gaatttacta ctgtggtccc acgtgatgat ccgcagtttg ataattatgt taaaatttgt 960
gatcagtgtg ttgatggtgt aggaacacgt ccaaaagatg atgaaccgag accaaagtca 1020
cgctcaagtt caagacctgc tacaagaaca agttctccgg cgccaagaca acaacgccca 1080
aagaaggaga aaaagccaaa gaagcaggat gatgaagtag ataaagcatt gacctcaaat 1140
gaggagagga acaatgcaca gctggaattt gatgaggaac ccaaggtgat taactggggg 1200
gatgcagctc taggagagaa tgaacttgga ggaggtcatc atcaccatca ccactaa 1257

<210> SEQ ID NO 7
<211> LENGTH: 1098
<212> TYPE: PRT
<213> ORGANISM: Infectious Bronchitis Virus

<400> SEQUENCE: 7

```
Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Phe Ser Ala Ala Ser
65                  70                  75                  80

Val Ala Met Thr Ala Pro Leu Ser Gly Met Ser Trp Ser Ala Ser Ser
                85                  90                  95

Phe Cys Thr Ala His Cys Asn Phe Thr Ser Tyr Ile Val Phe Val Thr
            100                 105                 110

His Cys Phe Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Thr
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
            340                 345                 350

Val Ser Leu Thr Tyr Gly Pro Ile Gln Gly Gly Cys Lys Gln Ser Val
        355                 360                 365

Phe Asn Gly Lys Ala Thr Cys Cys Tyr Ala Tyr Ser Tyr Gly Gly Pro
    370                 375                 380

Arg Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415
```

-continued

```
Thr Ala Thr Gln Pro Pro Val Leu Thr Gln Asn Phe Tyr Asn Asn Ile
            420                 425                 430

Thr Leu Gly Lys Cys Val Asp Tyr Asn Val Tyr Gly Arg Thr Gly Gln
        435                 440                 445

Gly Phe Ile Thr Asn Val Thr Asp Leu Ala Thr Ser His Asn Tyr Leu
    450                 455                 460

Ala Asp Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
                485                 490                 495

Cys Glu Asp Val Asn Gln Gln Phe Val Val Ser Gly Gly Lys Leu Val
            500                 505                 510

Gly Ile Leu Thr Ser Arg Asn Glu Thr Gly Ser Gln Pro Leu Glu Asn
        515                 520                 525

Gln Phe Tyr Ile Lys Ile Thr Asn Gly Thr His Arg Ser Arg Arg Ser
    530                 535                 540

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
                565                 570                 575

Glu Gln Phe Val Ala Pro Leu Leu Asn Val Thr Glu Asn Val Leu Ile
            580                 585                 590

Pro Asn Ser Phe Asn Leu Thr Val Thr Asp Glu Tyr Ile Gln Thr His
        595                 600                 605

Met Asp Lys Ile Gln Ile Asn Cys Leu Gln Tyr Val Cys Gly Asn Ser
    610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Ser Phe Tyr Ser Ser Thr Lys Pro Ser Gly Phe Asn Thr Pro Val
            660                 665                 670

Phe Ser Asn Leu Ser Thr Gly Glu Phe Asn Ile Ser Leu Leu Leu Thr
        675                 680                 685

Thr Pro Ser Ser Pro Arg Gly Arg Ser Phe Ile Glu Asp Leu Leu Phe
    690                 695                 700

Thr Ser Val Glu Ser Val Gly Leu Pro Thr Asp Glu Ala Tyr Lys Lys
705                 710                 715                 720

Cys Thr Ala Gly Pro Leu Gly Phe Leu Lys Asp Leu Ala Cys Ala Arg
                725                 730                 735

Glu Tyr Asn Gly Leu Leu Val Leu Pro Pro Ile Ile Thr Ala Glu Met
            740                 745                 750

Gln Thr Leu Tyr Thr Ser Ser Leu Val Val Ser Met Ala Phe Gly Gly
        755                 760                 765

Ile Thr Ser Ala Gly Ala Ile Pro Phe Ala Thr Gln Leu Gln Ala Arg
    770                 775                 780

Ile Asn His Leu Gly Ile Thr Gln Ser Leu Leu Leu Lys Asn Gln Glu
785                 790                 795                 800

Lys Ile Ala Ala Ser Phe Asn Lys Ala Ile Gly His Met Gln Glu Gly
                805                 810                 815

Phe Arg Ser Thr Ser Leu Ala Leu Gln Gln Ile Gln Asp Val Val Asn
            820                 825                 830
```

-continued

Lys Gln Ser Ala Ile Leu Thr Glu Thr Met Leu Ala Leu Asn Lys Asn
835 840 845

Phe Gly Ala Ile Ser Ser Val Ile Gln Asp Ile Tyr Gln Gln Leu Asp
850 855 860

Asp Ile Gln Ala Asp Ala Gln Val Asp Arg Leu Ile Thr Gly Arg Leu
865 870 875 880

Ser Ser Leu Ser Val Leu Ala Ser Ala Lys Gln Ser Glu Tyr Ile Arg
885 890 895

Val Ser Gln Gln Arg Glu Leu Ala Thr Gln Lys Ile Asn Glu Cys Val
900 905 910

Lys Ser Gln Ser Ile Arg Tyr Ser Phe Cys Gly Asn Gly Arg His Val
915 920 925

Leu Thr Ile Pro Gln Asn Ala Pro Asn Gly Ile Val Phe Ile His Phe
930 935 940

Thr Tyr Thr Pro Glu Ser Phe Ile Asn Val Thr Ala Val Val Gly Phe
945 950 955 960

Cys Val Ser Pro Ala Asn Ala Ser Gln Tyr Ala Ile Val Pro Ala Asn
965 970 975

Gly Arg Gly Ile Phe Ile Gln Val Asn Gly Ser Tyr Tyr Ile Thr Ala
980 985 990

Arg Asp Met Tyr Met Pro Arg Asp Ile Thr Ala Gly Asp Ile Val Thr
995 1000 1005

Leu Thr Ser Cys Gln Ala Asn Tyr Val Ser Val Asn Lys Thr Val
1010 1015 1020

Ile Thr Thr Phe Val Asp Asn Asp Asp Phe Asp Phe Asp Asp Glu
1025 1030 1035

Leu Ser Lys Trp Trp Asn Glu Thr Lys His Glu Leu Pro Asp Phe
1040 1045 1050

Asp Gln Phe Asn Tyr Thr Ile Pro Val Leu Asn Ile Thr Tyr Asp
1055 1060 1065

Ile Asp Lys Ile Glu Glu Val Ile Lys Gly Leu Asn Asp Ser Leu
1070 1075 1080

Ile Asp Leu Glu Thr Leu Ser Ile Leu Lys Thr Tyr Ile Lys Trp
1085 1090 1095

<210> SEQ ID NO 8
<211> LENGTH: 3296
<212> TYPE: DNA
<213> ORGANISM: Artificial Sequence
<220> FEATURE:
<223> OTHER INFORMATION: synthetic

<400> SEQUENCE: 8
atgttggtga agtcactgtt tctagtgacc attttgtttg cactatgtag tgctaattta 60
tatgacaacg aatcttttgt gtattactac cagagtgctt ttaggccagg acatggttgg 120
catttacatg gaggtgctta tgcagtagtt aatgtgtcta gtgaaaataa taatgcaggt 180
actgccccaa gttgcactgc tggtgctatt ggctacagta agaatttcag tgcggcctca 240
gtagccatga ctgcaccact aagtggtatg tcatggtctg cctcatcttt ttgtacagct 300
cactgtaatt ttacttctta tatagtgttt gttacacatt gttttaagag cggatctaat 360
agttgtcctt tgacaggtct tattccaagc ggttatattc gtattgctgc tatgaaacat 420
ggaagtgcta cgcctggtca cttattttat aacttaacag tttctgtgac taaatatcct 480
aagtttagat cgctacaatg tgttaataat catacttctg tatatttaaa tggtgacctt 540

-continued

```
gttttcacat ctaactatac tgaagatgtt gtagctgcag gtgtccattt taaaagtggt    600
ggacctataa cttataaagt tatgagagag gttaaagcct tggcttattt tgtcaatggt    660
actgcacatg atgtcattct atgtgatgac acacctagag gtttgttagc atgccaatat    720
aatactggca atttttcaga tggcttctat ccttttacta atactagtat tgttaaggat    780
aagtttattg tttatcgtga aagtagtgtc aatactactt tgacattaac taatttcacg    840
tttagtaatg aaagtggtgc ccctcctaat acaggtggtg ttgacagttt tattttatac    900
cagacacaaa cagctcagag tggttattat aattttaatt tttcatttct gagtagtttt    960
gtttataggg aaagtaatta tatgtatgga tcttaccatc cacgttgtag ttttagacct   1020
gaaaccctta atggtttgtg gtttaattcc ctttctgttt cattaacata cggtcccatt   1080
caaggtggtt gtaagcaatc tgtatttaat ggtaaagcaa cttgttgtta tgcttattca   1140
tacggaggac ctcgtgcttg taaaggtgtc tatagaggtg agctaacaca gcattttgaa   1200
tgtggtttgt tagtttatgt tactaagagc gatggctccc gtatacaaac tgcaacacaa   1260
ccacctgtat taacccaaaa tttttataat aacatcactt taggtaagtg tgttgattat   1320
aatgtttatg gtagaactgg acaaggtttt attactaatg taactgattt agctacttct   1380
cataattact tagcggatgg aggattagct attttagata catctggtgc catagacatc   1440
ttcgttgtac aaggtgaata tggccctaac tactataagg ttaatctatg tgaagatgtt   1500
aaccaacagt ttgtagtttc tggtggtaaa ttagtaggta ttctcacttc acgtaatgaa   1560
actggttctc agcctcttga aaaccagttt tacattaaga tcactaatgg aacacatcgt   1620
tctagacgtt ctgttaatga aaatgttacg aattgccctt atgttagtta tggcaagttt   1680
tgtataaaac ctgatggttc agtttctcct atagtaccaa aagaacttga acagtttgtg   1740
gcacctttac ttaatgttac tgaaaatgtg ctcataccta acagttttaa cttaactgtt   1800
acagatgagt acatacaaac gcatatggat aagatccaaa ttaattgtct gcagtatgtt   1860
tgtggcaact ctttggcttg tagaaagctg tttcaacaat atgggcctgt ttgtgacaac   1920
atattgtctg tagtaaatag tgttggtcaa aaagaagata tggaactttt aagcttctat   1980
tcttctacta aaccatctgg ttttaataca ccagttttta gtaatcttag cactggtgag   2040
tttaatatct ctcttttgtt aacaacccct agtagtccta gagggcgttc ttttattgaa   2100
gatcttttat ttacaagtgt tgaatctgtt ggattaccaa cagatgaagc ttataaaaag   2160
tgcactgcag gacctttagg ctttcttaaa gaccttgcat gtgctcgtga atataatggt   2220
ttgcttgtgt tgcctcctat tataacagca gaaatgcaaa ctttgtatac tagttctcta   2280
gtagtttcta tggcttttgg tggtattact tcagctggtg ctataccttt tgccacacaa   2340
ctgcaggcta gaattaatca cttgggtatt acccagtcac ttttgttgaa gaatcaagaa   2400
aaaattgctg cttcctttaa taaggccatt ggtcatatgc aggaaggttt taggagtaca   2460
tctctagcat tacaacaaat tcaagatgtt gttaataagc agagtgctat tcttactgag   2520
actatgttag cacttaataa aaattttggt gctatttctt ctgtgattca agacatttac   2580
cagcaacttg atgacataca agcagatgct caagtggatc gactcataac tggtagattg   2640
tcatcacttt ctgtcttagc atctgctaag cagtcggagt acattagagt gtcacaacag   2700
cgtgagttag ctactcagaa aattaatgag tgtgttaaat cacagtctat taggtattcc   2760
ttttgtggta atggacgaca tgttttaacc ataccacaaa atgcccctaa tggtatagtg   2820
tttatacact ttacttatac accagagagc tttattaatg ttactgcagt agtaggtttt   2880
tgtgtaagtc ctgctaatgc tagtcagtat gcaatagtgc ccgctaatgg taggggtatt   2940
```

```
tttatacaag ttaatggtag ttactacatc actgcacgtg atatgtatat gccaagagat   3000

attactgcag gagatatagt tacgcttact tcttgtcaag caaattatgt aagtgtaaac   3060

aagaccgtca ttactacatt tgtagacaat gatgattttg attttgatga cgagttatca   3120

aaatggtgga atgaaactaa gcacgagttg ccagactttg accagtttaa ttacaccatt   3180

cccgttttaa atataactta tgatattgac aagattgagg aagttattaa gggacttaat   3240

gattccttga ttgacctcga aacattgtca attctcaaaa cttatattaa gtggcc       3296


<210> SEQ ID NO 9
<211> LENGTH: 422
<212> TYPE: PRT
<213> ORGANISM: SARS-CoV-2

<400> SEQUENCE: 9

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
```

```
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala Gly Gly Gly
            420
```

<210> SEQ ID NO 10
<211> LENGTH: 1287
<212> TYPE: DNA
<213> ORGANISM: Artificial Sequence
<220> FEATURE:
<223> OTHER INFORMATION: synthetic

<400> SEQUENCE: 10

```
atgagcgata acggacccca gaaccaacgt aacgcccctc gcattacttt tggcgggcct      60

tccgactcta caggttctaa tcaaaacggg gagcgaagcg gggcacgcag caagcaacgc     120

aggcctcaag gtctgccaaa caacactgct tcttggttca ctgctctcac tcaacatggc     180

aaagaggatc tgaaattccc ccgaggacaa ggggtaccga tcaatactaa ctcctctccc     240

gatgatcaaa ttggatacta caggcgcgcc acccggagaa ttcgcggcgg agacgggaaa     300

atgaaggacc ttagtccaag atggtacttt tattacttgg ggaccggacc ggaagctggc     360

ttgccctatg gtgccaataa ggacggaatt atttgggtgg cgacagaggg cgctctgaat     420

actcccaagg accacatagg tactcggaat cctgctaata atgccgccat cgtgttgcag     480

ctcccccaag gcaccaccct acccaagggc ttttatgccg aggggtcccg cggcgggagc     540

caggcttcat ccaggagttc tagtcgctct cgcaactcat cccgcaactc cacccctggc     600

tctagtaggg gtactagtcc cgcccgaatg gccggcaatg gcggagacgc tgccctagcg     660

ctgttgttgc tggatagact caatcagctc gaaagtaaga tgtccggcaa aggacaacag     720

cagcaaggac aaacggttac caagaaaagc gcagcagagg caagtaagaa acccaggcaa     780

aagcgcactg ccaccaaagc ttacaacgtg acacaggcct ttggtcgcag aggacccgaa     840

caaacacaag gcaattttgg agatcaggaa cttataaggc aaggaacaga ctataagcat     900

tggccccaaa ttgcacaatt tgccccatcc gcttctgcat tcttcggtat gagtaggatt     960

ggaatggaag ttacacccag tggcacctgg ctcacatata caggcgctat caagcttgat    1020

gataaggatc cgaattttaa ggaccaggtg atcctgttga acaaacatat agacgcttat    1080

aaaacctttc cccgactga acctaagaaa gacaagaaga agaaagctga tgaaactcaa    1140

gcgctgccgc aaagacaaaa gaaacaacaa accgttacgc tcctgccagc agctgacctg    1200

gacgatttta gtaaacaact ccaacaaagc atgtctagcg ccgatagtac tcaggctggc    1260

ggcgggcacc accatcatca tcactga                                        1287
```

<210> SEQ ID NO 11

-continued

<211> LENGTH: 1215
<212> TYPE: PRT
<213> ORGANISM: SARS-CoV-2

<400> SEQUENCE: 11

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

Pro Phe Gly Glu Val Phe Asn Ala Thr Arg Phe Ala Ser Val Tyr Ala
340 345 350

Trp Asn Arg Lys Arg Ile Ser Asn Cys Val Ala Asp Tyr Ser Val Leu
355 360 365

Tyr Asn Ser Ala Ser Phe Ser Thr Phe Lys Cys Tyr Gly Val Ser Pro
370 375 380

Thr Lys Leu Asn Asp Leu Cys Phe Thr Asn Val Tyr Ala Asp Ser Phe

-continued

```
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815
```

```
Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Gly Gly Gly
    1205                1210                1215
```

<210> SEQ ID NO 12
<211> LENGTH: 3666
<212> TYPE: DNA
<213> ORGANISM: Artificial Sequence
<220> FEATURE:
<223> OTHER INFORMATION: synthetic

<400> SEQUENCE: 12
atgtttgtgt tcctggtact cctaccgctg gtgagctccc aatgcgtcaa tctcacgact 60
aggacacaac tcccacccgc ctacacgaac tcttttacaa ggggtgtata ctaccctgac 120
aaggtgttcc gcagcagcgt gctacatagc actcaagatt tgtttctgcc cttcttctct 180
aacgtaacat ggttccatgc gatacatgta tctggtacca atggaacaaa acggtttgat 240
aacccagttc tcccgtttaa tgatggagtt tactttgcat ccactgaaaa gtctaatata 300
atacgcggat ggattttcgg cacaacactg gatagtaaga cccagagtct gcttattgtc 360
aataacgcca ctaacgtggt gattaaggtg tgtgagtttc aattctgtaa tgacccattt 420
ctcggggttt actaccataa gaacaataag agctggatgg aatcagaatt tagagtttat 480
agcagcgcaa acaattgcac atttgaatac gtttctcaac cctttctgat ggatctcgaa 540
ggaaaacaag ggaactttaa gaacctcagg gaatttgtct tcaagaacat agatgggtac 600
ttcaaaattt acagcaagca tacaccaatt aacttggtta gagacctgcc ccagggattt 660
tctgcacttg aacccttggt tgacttgcct atcggcatta atattactcg atttcaaact 720
ctgctcgctt tgcaccgcag ctacctgaca ccgggagact cctctagtgg ctggaccgca 780
ggagcagctg catattatgt gggttatctc caacccagaa catttctgct aaagtacaac 840
gaaaatggga caatcaccga tgcggtcgac tgcgcattgg atcccctatc cgagactaag 900
tgtactttga agagctttac cgtggaaaag gggatctatc aaacttccaa ctttcgggtg 960
caaccgaccg aaagcatcgt tagatttccc aatatcacca acttgtgtcc ctttggcgaa 1020
gttttcaacg ctactcgctt tgcaagtgtc tatgcttgga atagaaagag gataagcaac 1080
tgcgtcgctg actattctgt tctgtataac tctgcgagct tttcaacttt caaatgctat 1140
ggggtctccc caaccaagct taatgacttg tgcttcacta acgtttatgc agatagcttc 1200
gtcatacggg gcgatgaagt gcggcaaatc gcgccaggac aaacaggtaa gatcgccgac 1260
tacaactata aactgccaga cgattttaca ggctgcgtga tcgcttggaa ctctaacaat 1320
cttgattcta aagttggtgg gaattataac tatctatatc gtctcttcag aaaatctaac 1380
ctcaagccct ttgagcggga tataagcaca gaaatctatc aggctgggtc tactccttgc 1440
aatggtgtcg aaggtttcaa ttgctacttt ccactgcaat cctacggctt tcaacctaca 1500
aatggtgtcg gttatcaacc gtatagagtt gttgtgctct cctttgagtt gctacacgct 1560
cctgccacgg tttgtggacc caagaagtca acgaatctgg tgaagaataa atgcgtcaat 1620
tttaatttta acggacttac ggggactggc gttctcaccg aatccaataa gaagttcctt 1680
ccattccagc aatttggccg cgatatcgcc gatacaacag acgctgtcag agatccacaa 1740
accttggaga tcttggatat tacaccatgc tctttcggcg gggtatcagt aatcacgccg 1800
gggacaaata catccaatca ggttgccgta ttgtatcagg atgtgaactg caccgaggtc 1860
cctgttgcca tacatgccga tcagttgact ccgacttggc gggtgtattc tacagggtct 1920
aatgtatttc aaaccagagc aggatgcctc atcggtgccg aacatgttaa taattcatat 1980
gagtgtgata tccccatagg agcaggcatt tgtgcatcct accaaactca gaccaactca 2040
ccaagacggg cccggtctgt ggcgtcccag tccataattg cctacacaat gagtcttgga 2100

```
gccgaaaact cagttgccta ttccaacaac tccatcgcta tccccacgaa ttttacaatc   2160

tcagttacca ctgaaatcct gcccgtatct atgacaaaga caagtgttga ttgcacaatg   2220

tatatctgcg gggactctac tgagtgctca aatctgctgc tacagtacgg tagcttttgt   2280

actcagctaa atcgcgcact caccgggatt gctgtagaac aagacaagaa tacacaagag   2340

gttttcgccc aagtgaaaca aatatacaaa acgcccccta taaaagactt cggtggtttt   2400

aactttagcc agattttgcc ggatccatcc aaaccatcta agcgctcttt cattgaagat   2460

ctcctgttca acaaagttac attggcggac gcaggtttca ttaagcaata tggggattgc   2520

cttggggata tcgcagcgcg ggatctgatt tgtgcccaga agttcaatgg tctgacggtt   2580

ctgccacccc tactcaccga tgaaatgatc gcgcaatata ccagcgctct tctggcaggt   2640

accatcactt ccggctggac cttcggagcc ggcgccgcac ttcaaatccc tttcgccatg   2700

caaatggcat atagatttaa tggcatcggt gtcacccaaa acgtattgta tgagaaccaa   2760

aagctgattg ccaatcaatt taatagcgca attggtaaaa tacaagacag cctgagcagt   2820

acggcaagcg cactcgggaa gcttcaagat gtagttaatc agaatgctca ggctttgaat   2880

actcttgtga aacaactctc ttccaatttt ggcgccatct catctgtgct caacgacatt   2940

ctttcccgac tcgataaggt ggaagctgaa gttcaaatcg atcggctcat tacaggcaga   3000

ctgcagtctc tccaaaccta cgtcacccag caactgatta gggcggcaga aattcgcgct   3060

tctgcaaatc ttgcagccac aaagatgagc gagtgtgtcc tgggccaatc aaagcgcgtc   3120

gacttttgcg gaaaggggta tcatctcatg agctttccac aatcagcccc acatggagtt   3180

gtctttctcc atgtaacgta cgtccctgct caggaaaaga atttcaccac agccccagct   3240

atttgccatg acggaaaggc tcacttccca cgtgaaggcg tatttgtatc aaatggcacc   3300

cactggttcg tcacccaacg taacttttac gagcctcaga ttatcaccac ggataacacg   3360

ttcgtcagcg ggaattgtga tgtagtcatt ggtattgtca ataataccgt gtatgatccc   3420

cttcaacccg aattggactc ctttaaagaa gaactcgaca aatactttaa gaaccatacg   3480

tcccctgacg tggacctcgg tgacatttca ggcataaatg cctcagtggt gaacattcaa   3540

aaggaaatcg ataggctgaa cgaagtggcc aagaatttga acgaaagttt gattgatctc   3600

caagaactgg ggaaatacga acaatatata aaatggggtg gcggacacca tcatcatcac   3660

cattaa                                                              3666
```

<210> SEQ ID NO 13
<211> LENGTH: 34
<212> TYPE: DNA
<213> ORGANISM: Artificial Sequence
<220> FEATURE:
<223> OTHER INFORMATION: Synthetic - forward primer N6xHis

<400> SEQUENCE: 13

```
atcactgaat tcaccatggc aagcggtaaa gcag                                 34
```

<210> SEQ ID NO 14
<211> LENGTH: 68
<212> TYPE: DNA
<213> ORGANISM: Artificial Sequence
<220> FEATURE:
<223> OTHER INFORMATION: Synthetic- reverse primer N6xHis

<400> SEQUENCE: 14

```
atcactgcgg ccgcttagtg gtgatggtga tgatgacctc ctccaagttc attctctcct     60
```

agagctgc 68

<210> SEQ ID NO 15
<211> LENGTH: 42
<212> TYPE: DNA
<213> ORGANISM: Artificial Sequence
<220> FEATURE:
<223> OTHER INFORMATION: Synthetic- forward primer S1 6xHis

<400> SEQUENCE: 15
atcactgaat tcaccatgtt ggtgaagtca ctgtttctag tg 42

<210> SEQ ID NO 16
<211> LENGTH: 89
<212> TYPE: DNA
<213> ORGANISM: Artificial Sequence
<220> FEATURE:
<223> OTHER INFORMATION: Synthetic -reverse primer S1 6xHis

<400> SEQUENCE: 16
atcactgcgg ccgctcagtg gtgatggtga tgatgccctc cgccggagga tccagttcca 60
ttagtgatct taatgtaaaa ctggttttc 89

<210> SEQ ID NO 17
<211> LENGTH: 22
<212> TYPE: DNA
<213> ORGANISM: Artificial Sequence
<220> FEATURE:
<223> OTHER INFORMATION: Synthetic-  forward primer IBV N gene

<400> SEQUENCE: 17
atgctcaacc tagtccctag ca 22

<210> SEQ ID NO 18
<211> LENGTH: 21
<212> TYPE: DNA
<213> ORGANISM: Artificial Sequence
<220> FEATURE:
<223> OTHER INFORMATION: Synthetic- reverse primer IBV N gene

<400> SEQUENCE: 18
tcaaactgcg gatcatcacg t 21

<210> SEQ ID NO 19
<211> LENGTH: 8
<212> TYPE: PRT
<213> ORGANISM: Artificial Sequence
<220> FEATURE:
<223> OTHER INFORMATION: Synthetic- OVA I

<400> SEQUENCE: 19

Ser Ile Ile Asn Phe Glu Lys Leu
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic- OVA II -continued

```
<400> SEQUENCE: 20

Ile Ser Gln Ala Val His Ala Ala His Ala Glu Ile Asn Glu Ala Gly
1               5                   10                  15

Arg
```